US008419784B2

(12) United States Patent
Matsuoka et al.

(10) Patent No.: US 8,419,784 B2
(45) Date of Patent: Apr. 16, 2013

(54) STENT DELIVERY DEVICE

(75) Inventors: Emi Matsuoka, Fujinomiya (JP);
Keitaro Morishita, Fujinomiya (JP);
Yousuke Moriuchi, Fujinomiya (JP)

(73) Assignee: Terumo Kabushiki Kaisha,
Shibuya-Ku, Tokyo (JP)

( * ) Notice: Subject to any disclaimer, the term of this patent is extended or adjusted under 35 U.S.C. 154(b) by 146 days.

(21) Appl. No.: 12/879,828

(22) Filed: Sep. 10, 2010

(65) Prior Publication Data

US 2010/0331953 A1 Dec. 30, 2010

Related U.S. Application Data

(63) Continuation of application No. 11/390,273, filed on Mar. 28, 2006, now Pat. No. 7,815,669.

(30) Foreign Application Priority Data

Mar. 28, 2005 (JP) ................................. 2005-093254
Mar. 29, 2005 (JP) ................................. 2005-094725
Sep. 30, 2005 (JP) ................................. 2005-287689

(51) Int. Cl.
*A61F 2/06* (2006.01)
*A61M 29/00* (2006.01)

(52) U.S. Cl.
USPC .......... 623/1.11; 606/191; 606/192; 606/194; 606/195

(58) Field of Classification Search .................. 606/108, 606/191, 194, 195, 198, 192; 623/1.11, 1.23
See application file for complete search history.

(56) References Cited

U.S. PATENT DOCUMENTS 5,534,007 A * 7/1996 St. Germain et al. ........ 623/1.11
5,904,667 A    5/1999 Falwell
(Continued)

FOREIGN PATENT DOCUMENTS

JP    8-038613 A    2/1996
JP    8-252321 A    10/1996
(Continued)

OTHER PUBLICATIONS

Official Action dated Nov. 30, 2010, issued by the Japanese Patent Office in corresponding Japanese Patent Application No. 2005-093254, and partial English language translation of the Office Action.

(Continued)

*Primary Examiner* — Vy Q Bui
(74) *Attorney, Agent, or Firm* — Buchanan Ingersoll & Rooney PC

(57) ABSTRACT

A stent delivery device includes a distal-side tube having a guide wire lumen; a proximal-side tube whose distal portion is fixed to a proximal portion of the distal-side tube; a cylindrical member which encloses a distal side of the distal-side tube and is slidable toward a proximal end of the distal-side tube; a stent accommodated in the cylindrical member; and a pulling member 6 for moving the cylindrical member toward a proximal side of the stent delivery device. The distal-side tube has a proximal-side opening which is open at the proximal side of the distal-side tube; and a stent-locking portion for preventing the stent from moving to the proximal side of the stent delivery device. The outer diameter of the proximal-side tube is set smaller than that of a portion, having a maximum diameter, which is disposed in a region of the stent delivery device which is distal from the proximal-side tube.

12 Claims, 57 Drawing Sheets

U.S. PATENT DOCUMENTS

| | | | |
|---|---|---|---|
| 8,025,692 B2 * | 9/2011 | Feeser | 623/1.12 |
| 2004/0148009 A1 | 7/2004 | Buzzard et al. | |
| 2004/0181239 A1 | 9/2004 | Dorn et al. | |
| 2005/0038493 A1 | 2/2005 | Feeser | |
| 2007/0191925 A1 | 8/2007 | Dorn | |

FOREIGN PATENT DOCUMENTS

| | | |
|---|---|---|
| JP | 11-505162 A | 5/1999 |
| JP | 2001-506875 A | 5/2001 |
| JP | 2001-516256 A | 9/2001 |
| JP | 2001-522694 A | 11/2001 |
| JP | 2002-045426 A | 2/2002 |
| JP | 2004-527316 A | 9/2004 |
| JP | 2005-504603 A | 2/2005 |
| WO | WO 96/31174 | 10/1996 |
| WO | WO 98/23241 A2 | 6/1998 |
| WO | WO 99/25280 A1 | 5/1999 |
| WO | WO 01/54614 A2 | 8/2001 |
| WO | WO 02/087470 A1 | 11/2002 |
| WO | WO 03/030783 A1 | 4/2003 |
| WO | WO 2004/004597 A2 | 1/2004 |
| WO | WO 2004/062458 A2 | 7/2004 |

OTHER PUBLICATIONS

English Translation of International Search Report dated Oct. 11, 2007 issued in corresponding International Patent Application No. PCT/JP2006/306286 (Form PCT/ISA/210).

Notification of Transmittal of Translation of the International Preliminary Report on Patentability (Form PCT/IB/338) dated Oct. 11, 2007, with attached English translation of International Preliminary Report on Patentability issued in corresponding International Patent Application No. PCT/JP2006/306286 (Form PCT/IB/373), and English translation of Written Opinion of the International Search Authority (Form PCT/ISA/237).

Official Action issued on May 24, 2011 by the Japanese Patent Office in corresponding Japanese Patent Application No. 2005-287689, and partial English language translation of the Official Action.

Official Action issued on Jun. 7, 2011 by the Japanese Patent Office in corresponding Japanese Patent Application No. 2006-088715, and partial English language translation of the Official Action.

Chinese Office Action issued Jun. 12, 2012 by the Chinese Patent Office in corresponding Chinese Patent Application No. 200680010036.1, and partial English translation thereof.

* cited by examiner

STENT DELIVERY DEVICE

CROSS REFERENCE TO RELATED APPLICATION

This application is a continuation of application Ser. No. 11/390,273, filed Mar. 28, 2006, which in turn claims priority to Japanese Patent Application No. 2005-93254 filed Mar. 28, 2005, Japanese Patent Application No. 2005-94725 filed Mar. 29, 2005, and Japanese Patent Application No. 2005-287689 filed Sep. 30, 2005. The entire content of all four applications is incorporated herein by reference.

FIELD OF THE INVENTION

The present invention relates to a stent delivery device for implanting a stent at a stenosed portion or a closed portion generated in internal organs such as a blood vessel, the bile duct, the trachea, the esophagus, the ureter, a digestive tract, and the like.

BACKGROUND DISCUSSION

Stent delivery devices proposed heretofore are used to secure a lumen or a space in a body cavity by implanting the stent at the lumen, the stenosed portion or the closed portion of the body cavity in an internal organ such as the blood vessel, the bile duct, the trachea, the esophagus, the ureter, the digestive tract, and the like.

The stent is classified into a self-expandable stent and a balloon expandable stent in dependence on the function thereof and an implantation method.

The balloon expandable stent which itself has no expanding function. To implant the stent at a desired portion, after the stent is inserted into the desired portion, a balloon disposed in the stent is inflated to expand (thermoplastically deform) the stent by an expansive force of the balloon so that the stent is fixed, with the stent in close contact with the inner surface of the desired portion.

It is necessary to perform the above-described operation of expanding the stent of this type in implanting it in the desired portion. The stent can be implanted in the desired portion by directly mounting on the contracted balloon. Thus the balloon expandable stent does not have a problem in this respect. But the stent does not have an expansive force by itself. Therefore there is a possibility that the diameter of the stent becomes smaller due to the pressure of the blood vessel with an elapse of time and that a constriction occurs again.

On the other hand, the self-expandable stent itself has contracting and expanding functions. To implant the stent at a desired portion, after it is inserted into the desired portion in a contracted state, an applied stress is released to maintain the contracted state. For example, the stent is accommodated in a sheath having a smaller diameter than the inner diameter of the desired portion by contracting the stent. After the distal end of the sheath reaches the desired portion, the stent is pressed out of the sheath. Because the stent is released from the sheath, the applied stress is removed. Thereby the stent returns to the original configuration. Thereby the stent adheres to the inner surface of the desired portion.

Unlike the balloon expandable stent, it is unnecessary to perform the operation of expanding the stent of this type in implanting it in the desired portion. Further there is no possibility that the diameter of the stent becomes smaller due to the pressure of the blood vessel and that a constriction occurs again.

As compared with the balloon expandable stent, it is difficult to implant the self-expandable stent correctly at the desired portion for the reason described below. After the stent is disposed at a desired stenosed portion, a liquid is injected into a balloon. Thus the stent does not move longitudinally when the stent is expanded. The delivery system of the self-expandable stent has a construction in which the stent is restrictedly accommodated between an inner tube and an outer tube, and a locking portion for restricting the movement of the stent is provided in the inner tube at a position located at the proximal side of the stent. By pulling the outer tube toward the proximal side of a system, the stent is released from the restricted state and expands itself. The stent is liable to move forward when it expands owing to loosening of the outer tube inside a body cavity and friction between the stent and the body cavity, between the stent and a catheter or between the stent and a valve of a device called an introducer for introducing the delivery system into a patient's body.

In the system constructed of three tubular members described in WO96/31174, the outermost tube is provided in addition to the inner tube and the outer tube. The stent is restrictedly accommodated between the inner tube and the outer tube, with the outermost tube and the inner tube fixed outside the patient's body. Thereby stent does not move. In this construction, there may be friction between the outermost tube and the body cavity as well as the valve. But the outer tube is merely pulled to expand the stent. Therefore the stent hardly moves.

In the delivery system of the self-expandable stent proposed by the present applicant and described in JPA1996-252321, the stent little moves when the stent expands (discharged from system).

As the delivery system of the self-expandable stent, as described in the above-described WO96/31174 and JPA1996-252321, an "over the wire type" in which the guide wire lumen extends from the proximal end of a system to the distal end thereof. As the reason for the adoption of the "over the wire type", the construction of discharging the stent from the appliance necessitates the outer sheath to be moved to the proximal side of the appliance.

When a plurality of stent delivery systems is prepared to implant the stent in the desired portion in the patient's body, systems having different outer diameters are used owing to a change of the outer diameter of the stent caused by the expansion thereof. Thus after a first stent delivery system is inserted into a blood vessel, it is exchanged with another system. In the "over the wire type", the guide wire lumen is in penetration through the system from its distal end to its proximal end. To introduce the system into the patient's body, the guide wire is required to be not less than twice as long as the entire length of the system. Thus a long period of time is required to exchange the systems.

Recently the stent is demanded to be implanted in peripheral portions in the patient's body. Thus the development of a stent delivery system having a small diameter is strongly demanded.

The system of WO96/31174 is difficult to have a small diameter because it uses three tubular members.

Therefore it is a first object of the present invention to provide a stent delivery device, using a self-expandable stent, which facilitates an operation of exchanging the stent delivery device with a different stent delivery device in implanting a stent at a desired portion and has a small diameter.

As described above, the delivery system of the self-expandable stent has the construction in which the stent is restrictedly accommodated between an inner tube and an outer tube, and a locking portion for restricting the movement of the stent is provided in the inner tube at the position located at the proximal side of the stent. By pulling the outer tube toward the proximal side of a stent delivery device, the stent is released from the restricted state and expands itself. At this time, it is necessary for an operator to fix the inner tube to a certain position with one hand to prevent a stent-implanted position from moving forward and perform an operation of pulling the outer tube with the other hand. In implanting the stent in a bile duct through an endoscope, the inner tube cannot be fixed to a certain position. Therefore the operator performs an operation of adjusting the stent-implanting position by expanding the stent little by little and pulling the outer tube, with the operator holding the endoscope with one hand. To solve such a disadvantage in operability, a system having a housing assembly has been developed.

In US2004148009, the housing having the slider which can be moved in parallel is proposed. In this housing, the shaft is mounted inside the housing, and the proximal end of the outer tube is connected with the slider longitudinally movable inside the housing. The stent is released by sliding the slider toward the proximal side of the system. According to the description made in WO01/54614, the system can be operated with one hand. But actually in this system, it is necessary to use the housing by fixing it to a hard surface fixed to an operating table or a patient's leg. Thus the system has a low operability and has a possibility that the implanting position of medical appliances are set at an unintended position. In addition, this system necessitates the housing to be not less than twice as long as the entire length of the slider. Therefore the housing assembly is relatively large.

The housing assembly described in WO96/31174 has a construction similar to the above housing assembly and not less than two different operation modes different in the operation speed thereof. This system also necessitates the housing to be not less than twice as long as the entire length of the slider and thus the housing assembly to be relatively large. Therefore it is difficult to operate the system with one hand.

In the housing assembly disclosed in WO2002/087470, the proximal end of the outer tube is connected with the track inside the housing, and the track is gradually moved rearward by the ratchet means to thereby release the stent. The system can be operated with one hand. This system also necessitates the housing to be not less than twice as long as the entire length of the slider and thus the housing assembly to be relatively large.

Therefore it is a second object of the present invention to provide a stent delivery device, using a self-expandable stent, which facilitates an operation of exchanging the stent delivery device with a different stent delivery device in implanting a stent at a desired portion and does not move from an implanted position.

SUMMARY

The first object described above is attained by the following a stent delivery device.

A stent delivery device comprises a distal-side tube having a guide wire lumen; a proximal-side tube whose distal portion is fixed to a proximal portion of said distal-side tube; a cylindrical member which encloses a distal side of said distal-side tube and is slidable toward a proximal end of said distal-side tube; a stent housed in said cylindrical member; and a pulling wire which extends inside said proximal-side tube, with one end portion thereof fixed to said cylindrical member, wherein said distal-side tube has a proximal-side opening which is open at said proximal side of said distal-side tube and communicates with said guide wire lumen; and a stent-locking portion which is disposed at said distal side of said distal-side tube and contacts a proximal end of said stent, thus preventing said stent from moving to said proximal side of said stent delivery device; and said stent is formed approximately cylindrically, housed in said cylindrical member, with said stent being compressed in an axial direction thereof, and expands outward and returns to a configuration before said stent is compressed, when said stent is implanted in an organism; said stent delivery device further comprising an operation portion, disposed at a proximal portion of said proximal-side tube, which has a pulling wire winding mechanism for winding said pulling wire and moving said cylindrical member toward a proximal side of said stent delivery device.

The second object described above is attained by the following a stent delivery device.

A stent delivery device comprises a distal-side tube having a guide wire lumen; a proximal-side tube whose distal portion is fixed to a proximal portion of said distal-side tube; a cylindrical member which encloses a distal side of said distal-side tube and is slidable toward a proximal end of said distal-side tube; a stent housed in said cylindrical member; and a pulling member which extends inside said proximal-side tube, with one end portion thereof fixed to said cylindrical member and is pulled toward said proximal side of said proximal-side tube to move said cylindrical member toward a proximal side of said stent delivery device, wherein said distal-side tube has a proximal-side opening which is open at said proximal side of said distal-side tube and communicates with said guide wire lumen; and a stent-locking portion which is disposed at said distal side of said distal-side tube and contacts a proximal end of said stent accommodated inside said cylindrical member, thus preventing said stent from moving to said proximal side of said stent delivery device; and said stent is formed approximately cylindrically, accommodated in said cylindrical member, with said stent being compressed in an axial direction thereof, and expands outward and returns to a configuration before said stent is compressed, when said stent is implanted in an organism; and

DETAILED DESCRIPTION OF THE PREFERRED EMBODIMENTS

Figure 1:
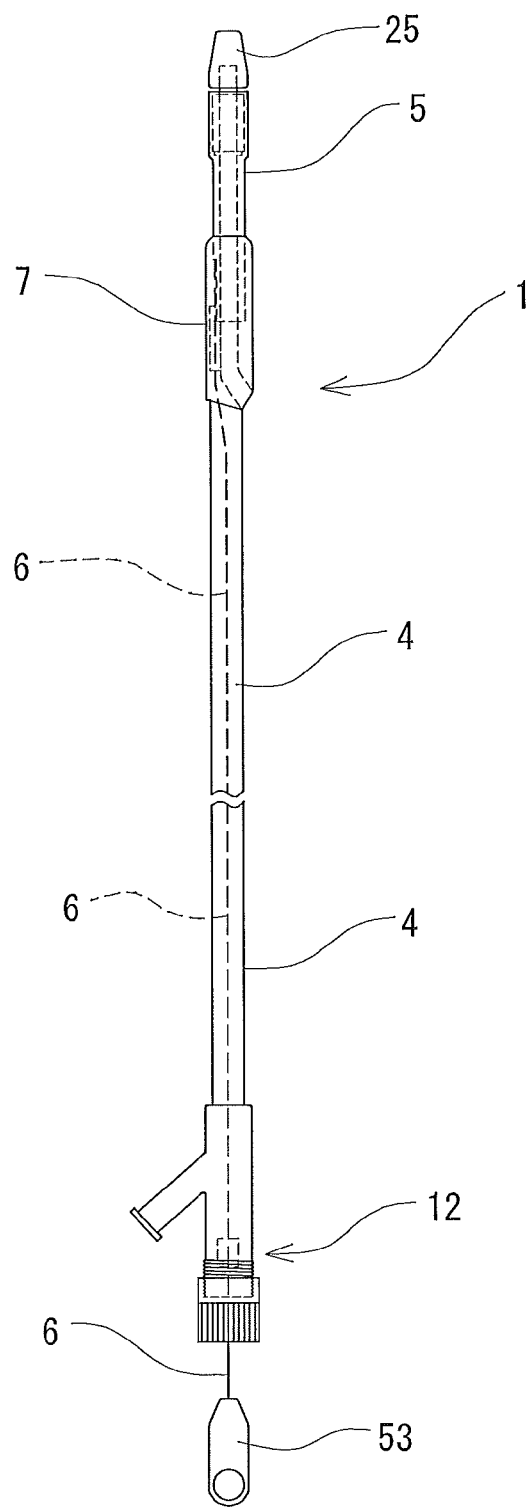
FIG. 1 is a partially schematic front view showing a stent delivery device of an embodiment of the present invention.

The embodiments of the stent delivery device of the present invention will be described below with reference to the drawings.

A stent delivery device 1 of the present invention includes a distal-side tube 2 having a guide wire lumen 21; a proximal-side tube 4 whose distal portion is fixed to a proximal portion of the distal-side tube 2; a cylindrical member (in other words, stent accommodation cylindrical member) 5 which encloses a distal side of the distal-side tube 2 and is slidable toward a proximal end of the distal-side tube 2; a stent 3 housed (in other words, accommodated) in the stent accommodation cylindrical member 5; and a pulling member 6 which extends inside the proximal-side tube 4, with one end portion thereof fixed to the stent accommodation cylindrical member 5 and is pulled toward the proximal side of the proximal-side tube 4 to move the stent accommodation cylindrical member 5 toward a proximal side of the stent delivery device 1.

The distal-side tube 2 has a proximal-side opening 23 which is open at the proximal side of the distal-side tube 2 and communicates with the guide wire lumen 21; and a stent-locking portion 22 which is disposed at the distal side of the distal-side tube 2 and contacts a proximal end of the stent 3 accommodated inside the stent accommodation cylindrical member 5, thus preventing the stent 3 from moving to the proximal side of the stent delivery device. The stent 3 is formed approximately cylindrically and accommodated in the stent accommodation cylindrical member 5, with the stent 3 being compressed in an axial direction thereof. The stent 3 expands outward and returns to a configuration before the stent is compressed, when the stent is implanted in an organism. The outer diameter of the proximal-side tube 4 is set smaller than that of a portion, having a maximum diameter, which is disposed in a region of the stent delivery device 1 distal from the proximal-side tube 4.

According to the stent delivery device of the present invention using a self-expandable stent, the opening at the proximal side thereof is disposed not at the proximal end thereof, but at the proximal side of the distal-side tube. Therefore in a stent-implanting operation, it is easy to perform an operation of exchanging the stent delivery device with a stent delivery device of other types. The outer diameter of the proximal-side tube is set smaller than that of the portion, having the maximum diameter, which is disposed in the region of the stent delivery device 1 distal from the proximal-side tube 4. Therefore even in a state in which the guide wire is extended along the side surface of the proximal-side tube from the opening at the proximal side of the stent delivery device to the proximal side of the stent delivery device, the outer diameter of the proximal-side tube is set almost equally to that of the portion, having the maximum diameter, which is disposed in the region of the stent delivery device distal from the proximal-side tube. Thereby the stent can be inserted into a narrow blood vessel.

The stent delivery device of this embodiment has the distal-side tube 2; the proximal-side tube 4; the stent accommodation cylindrical member 5; the stent 3; and the pulling member 6.

The stent delivery device 1 of this embodiment has an intermediate tube 7 which encloses the proximal side of the distal-side tube 2 and the proximal side of the stent accommodation cylindrical member 5 and is fixed at the proximal portion thereof to the proximal portion of the distal-side tube 2 and the distal portion of the proximal-side tube 4. In the stent delivery device 1 of this embodiment, the intermediate tube 7 encloses the proximal side of the distal-side tube 2 and the proximal side of the stent accommodation cylindrical member 5 without preventing the stent accommodation cylindrical member 5 from moving toward the proximal side of the stent delivery device 1. One end portion of the pulling member 6 is fixed to the stent accommodation cylindrical member 5 inside the intermediate tube 7. The pulling member 6 passes a space between the intermediate tube 7 and the distal-side tube 2 and extends into the proximal-side tube 4. Thereby the pulling wire is not exposed.

As shown in FIGS. 1, 2, 3, and 5, the stent accommodation cylindrical member 5 is tubular having a predetermined length. The stent accommodation cylindrical member 5 is open at its distal end and proximal end. When the stent 3 is implanted in a stenosed portion of a lumen, the opening of the stent accommodation cylindrical member 5 at its distal end functions as a discharge opening. By being pressed out of the opening of the stent accommodation cylindrical member 5 at its distal end, a stress applied to the stent 3 is released and expands, thus returning to a configuration before it is compressed.

The length of the stent accommodation cylindrical member 5 is favorably in the range of 20 mm to 400 mm and more favorably in the range of 30 mm to 250 mm. The outer diameter of the stent accommodation cylindrical member 5 is favorably in the range of 1.0 mm to 4.0 mm and more favorably in the range of 1.5 mm to 3.0 mm. The inner diameter of the stent accommodation cylindrical member 5 is favorably in the range of 1.0 to 2.5 mm. In the stent accommodation cylindrical member 5 of this embodiment, the stent accommodation portion disposed at the distal side thereof is set as a large-diameter portion 51, whereas the proximal side thereof is set as a small-diameter portion. The outer diameter of the large-diameter portion is favorably in the range of 1.0 to 4.0 mm and more favorably in the range of 1.5 to 3.0 mm. The outer diameter of the small-diameter portion is favorably in the range of 1.0 to 4.0 mm and more favorably in the range of 1.2 to 2.8 mm. The stent accommodation cylindrical member 5 may have the same outer diameter over the whole length thereof.

As shown in FIGS. 2, 3, 5, and 6, the stent accommodation cylindrical member 5 has a slit 52 extending from the proximal end thereof to the distal side thereof. A projected portion (in this embodiment, tubular member 8 through which pulling member penetrates) formed on the outer surface of the distal-side tube 2 is capable of moving into the slit 52. The projected portion will be described later. In this embodiment, until the distal end of the slit 52 contacts the tubular member 8, the stent accommodation cylindrical member 5 is movable toward the proximal side of the stent delivery device. Thus the length of the slit 52 is set equally to or a little longer than a length in the range from the proximal end of the stent 3 accommodated in the stent accommodation cylindrical member 5 to the distal end of the stent accommodation cylindrical member 5.

Materials for forming the stent accommodation cylindrical member 5, the following materials are preferable in consideration of the property (flexibility, strength, sliding property, kink resistance, and stretching property) demanded for the stent accommodation cylindrical member are selected appropriately from the following substances: polyethylene, polypropylene, nylon, polyethylene terephthalate; and fluorine-containing polymer such as PTFE, ETFE; and thermoplastic elastomer. The thermoplastic elastomer is selected from among nylon family (for example, polyamide elastomer), urethane family (for example, polyurethane elastomer), polyester family (for example, polyethylene terephthalate elastomer), olefin family (for example, polyethylene elastomer, polypropylene elastomer).

It is preferable to treat the outer surface of the stent accommodation cylindrical member 5 so that the outer surface thereof displays lubricity. For example, hydrophilic polymers are applied to the outer surface thereof or fixed thereto: As the hydrophilic polymers, it is possible to use poly(2-hydroxyethyl methacrylate), polyhydroxyethyl acrylate, hydroxypropyl cellulose, copolymer of methyl vinyl ether and maleic anhydride, polyethylene glycol, polyacrylamide, polyvinyl pyrrolidone. The above-described substances may be applied or fixed to the inner surface of the stent accommodation cylindrical member 5 to enhance slidability.

The stent 3 is accommodated in the stent accommodation cylindrical member 5 at the distal portion thereof. The stent 3 is a so-called self-expandable stent. More specifically, the stent 3 is formed approximately cylindrical. When the stent 3 is inserted into an organism, the stent 3 is compressed in the axial direction thereof. When the stent 3 is implanted in the organism, the stent 3 expands outward and returns to a configuration before it is compressed. The stent 3 is held inside the stent accommodation cylindrical member 5, with the stent 3 being compressed in the axial direction thereof. Thus the stent 3 is held inside the stent accommodation cylindrical member 5, with the stent 3 pressing the inner surface of the stent accommodation cylindrical member 5 by a restoring force thereof. As described later, the stent-locking portion 22 provided inside the distal-side tube 2 prevents the stent 3 from moving toward the proximal side of the stent delivery device.

As the stent 3, it is possible to use the self-expandable stent of any types. For example, it is possible to preferably use the stent 3 having a configuration shown in FIG. 23 (showing a state in which by its self-expansion, stent returns to a configuration before it is compressed). The stent 3 of this example has a cylindrical frame body 3a, openings 34 partitioned (surrounded) from one another with frames 36a, 36b constructing the cylindrical frame body 3a, and cut-out portions 35 partitioned from one another with the frames 36a. The frame body 3a has both ends 33a, 33b.

As the material for forming the stent, synthetic resin or metal is used. Synthetic resin having a proper degree of hardness and elasticity is used. Synthetic resin compatible with organisms is preferable. For example, polyolefins (for example, polyethylene, polypropylene), polyester (for example, polyethylene terephthalate), fluororesin (for example, PTFE, ETFE), polylactic acid, polyglicolic acid, and copolymer of polylactic acid and polyglicolic acid which is absorbed into organisms. Metal compatible with organisms is preferable. For example, stainless steel, tantalum, nickel-titanium alloy. Super-elastic metal is especially preferable. It is preferable that the stent 3 is formed integrally without change points at which property changes rapidly being formed therein. The stent is formed by preparing a metal pipe having an outer diameter suitable for a desired portion in an organ at which the stent is implanted, removing a part of the side surface of the metal pipe by means of cutting work (for example, mechanical cutting, laser machining), chemical etching or the like, and forming a plurality of cut-out portions or openings on the side surface thereof.

Because the stent 3 has the cut-out portions 35 at the ends of the frame body 3a, the ends 33a, 33b of the stent 3 deform easily. The ends 33a, 33b are capable of partly deforming. Thereby the stent 3 has a favorable response to deformation of a blood vessel in which the stent 3 is implanted. Because the ends 33 are formed of the ends of a plurality of the frames 36a, the stent 3 is not broken easily and thus has a sufficient strength. The openings 34 surrounded with the frames 36a, 36b are formed between both ends 33a, 33b and deform easily by the deformation of the frame 36a. Thus the stent 3 deforms easily at its central portion (central portion of the frame body 3a). Neither the number of the cut-out portions and that of the openings are not limited to those shown in FIG. 23 nor the configuration of the cut-out portions and that of the openings is limited to those shown in FIG. 23. The number of the cut-out portions is set to preferably 3 to 10. The number of the openings is set to preferably 3 to 10.

The outer diameter of the frame body 3a is favorably in the range of 2.0 mm to 30 mm and more favorably in the range of 2.5 mm to 20 mm. The inner diameter of the frame body 3a is favorably in the range of 1.4 mm to 29 mm and more favorably in the range of 1.6 mm to 28 mm. The length of the frame body 3a is favorably in the range of 10 to 150 mm and more favorably in the range of 15 to 100 mm.

Figure 23:
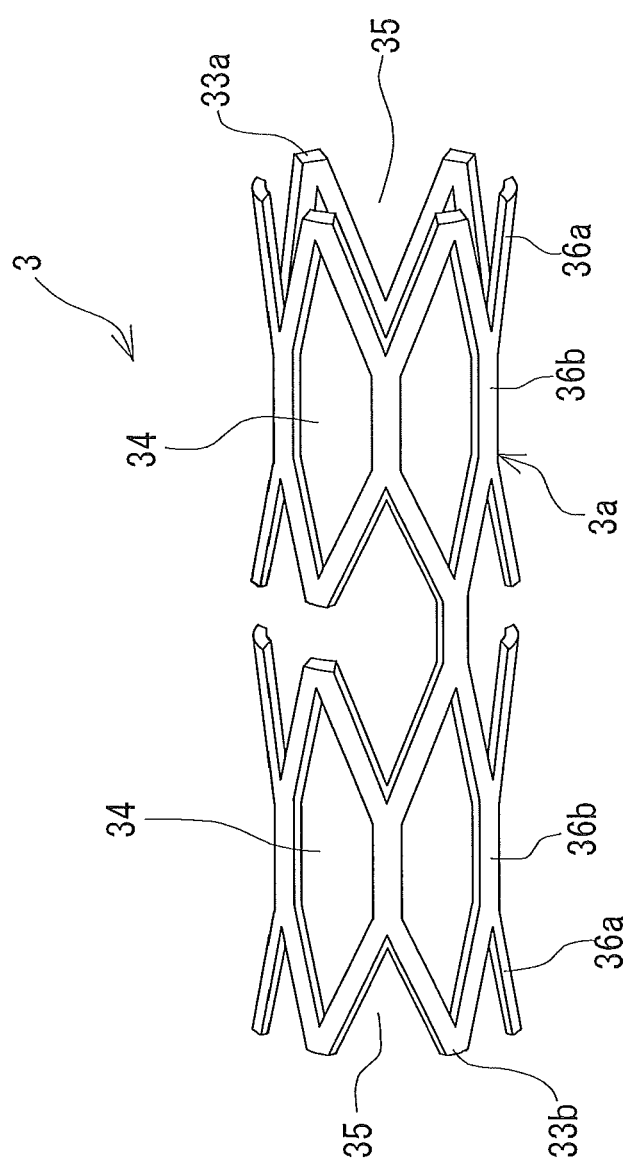
FIG. 23 is a perspective view showing a stent, to be implanted in a lumen, for use in the stent delivery device of the present invention.

The configuration of the stent is not limited to the one shown in FIG. 23. For example, the stent may have trapezoidal cut-out portions formed at both ends thereof and a plurality of hexagonal openings formed at the central portion thereof. As another example, the stent may have rectangular cut-out portions at both ends thereof and a plurality of rectangular (twice as long as length of cut-out portion) openings formed at the central portion thereof. As still another example, it is possible to use the stent of configurations other than the above-described one so long as it can be decreased in its diameter when it is inserted into a desired portion of an organ and restored to its original state when it reaches the desired portion thereof. For example, it is possible to use the stent coiled, cylindrical, roll-shaped, odd-shaped tubular, higher-order coil-shaped, leaf spring-like, basket-shaped, and mesh-shaped.

Super-elastic alloys can be preferably used as the super-elastic metal forming the stent. Herein the super-elastic alloy means a so-called shape memory alloy that shows super-elasticity essentially at the temperature (in the vicinity of 37° C.) of the organism. The following super-elastic metals can be favorably used: A Ti—Ni alloy of 49-53 atomic percent of Ni, a Cu—Zn alloy of 38.5-41.5 wt % of Zn, a Cu—Zn—X alloy of 1-10 wt % of X (X=Be, Si, Sn, Al, Ga), and a Ni—Al alloy of 36-38 atomic percent of Al. The Ti—Ni alloy is most favorable. The mechanical characteristic of the Ti—Ni alloy can be appropriately changed by replacing a part of the Ti—Ni alloy with 0.01-10.0% of X to obtain a Ti—Ni—X alloy (X=Co, Fe, Mn, Cr, V, Al, Nb, W, B and the like) or by replacing a part of the Ti—Ni alloy with 0.01-30.0 atomic percent of X to obtain a Ti—Ni—X alloy (X=Cu, Pb, Zr). Further the mechanical characteristic of the super-elastic alloy can be appropriately changed by selectively adopting a cold working ratio or/and the condition of final heat treatment. Furthermore the mechanical characteristic of the super-elastic alloy can be appropriately changed by using the Ti—Ni—X alloy and selectively adopting a cold working ratio or/and the condition of final heat treatment.

The buckling strength (yield stress when load is applied to stent) of the super-elastic alloy to be used is favorably in the range of 5-200 kg/mm$^2$ (22° C.) and more favorably in the range of 8-150 kg/mm$^2$. The restoring stress (yield stress when load is eliminated from stent) of the super-elastic alloy is favorably in the range of 3-180 kg/mm² (22° C.) and more favorably in the range of 5-130 kg/mm². The super-elasticity means that when a metal is deformed (bent, stretched, compressed) to a region in which it deforms plastically at a service temperature, it returns to its original configuration substantially without heating it after an applied load is eliminated.

The stent to be used in the stent delivery device of the present invention may have a diameter-reducible body formed approximately cylindrically and a cylindrical cover (not shown) sealing the side surface of the body.

Figure 2:
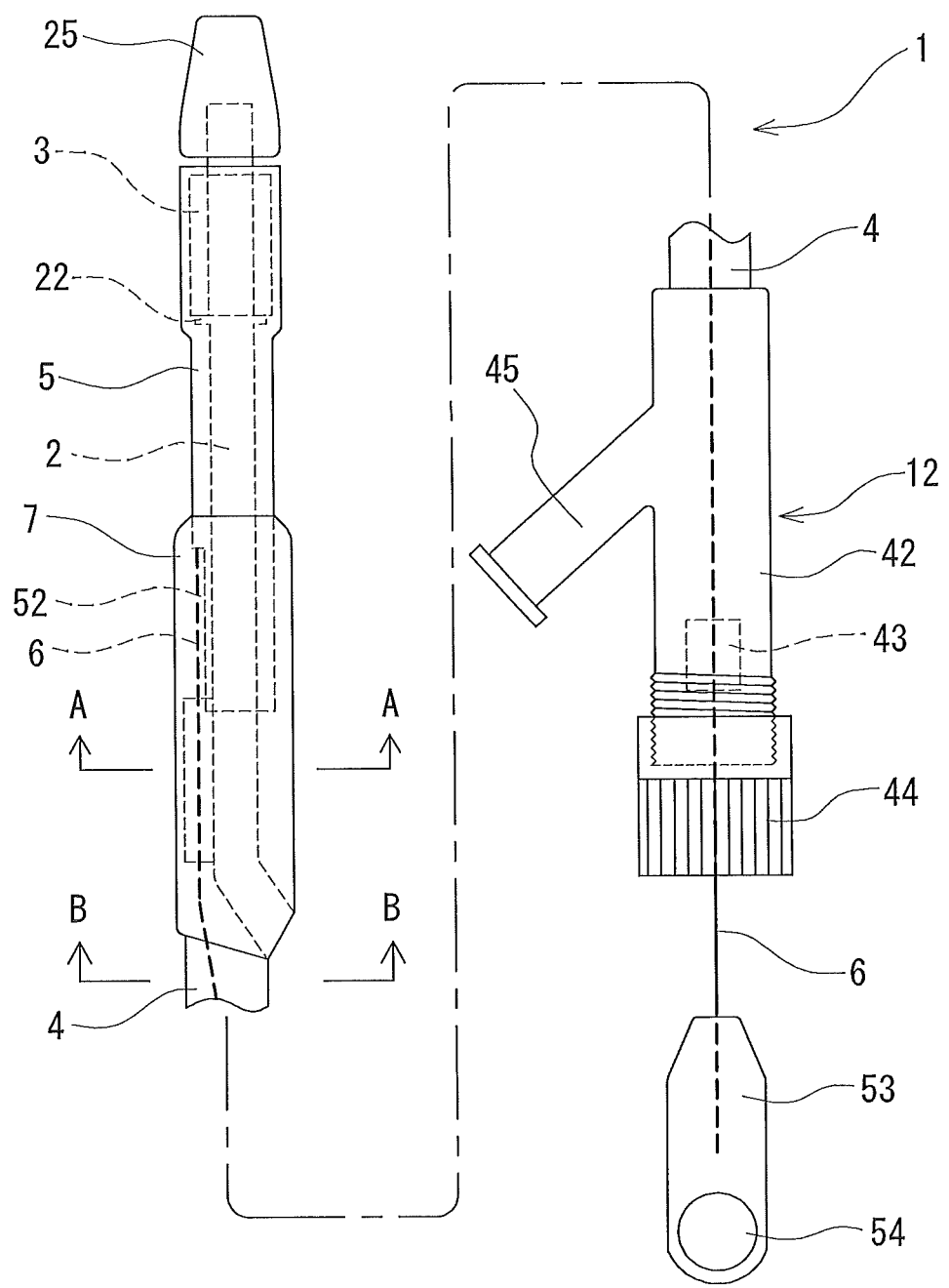
FIG. 2 is a partially schematic enlarged outlook view showing the stent delivery device shown in FIG. 1.
Figure 3:
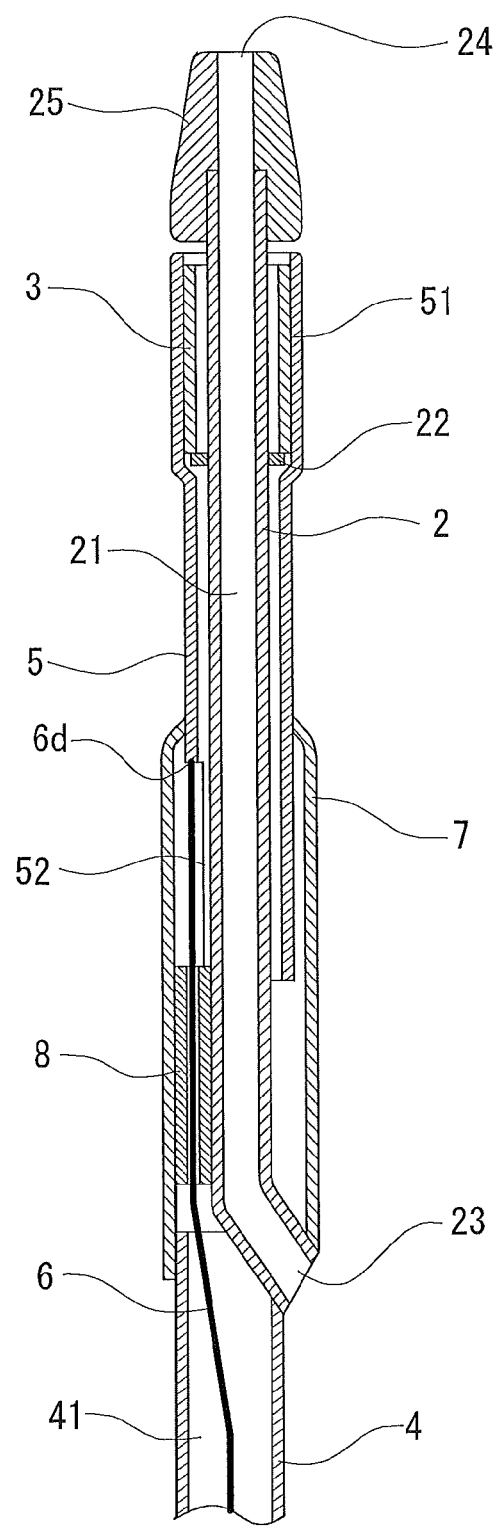
FIG. 3 is an enlarged sectional view showing the neighborhood of a distal portion of the stent delivery device shown in FIG. 1.
Figure 7:
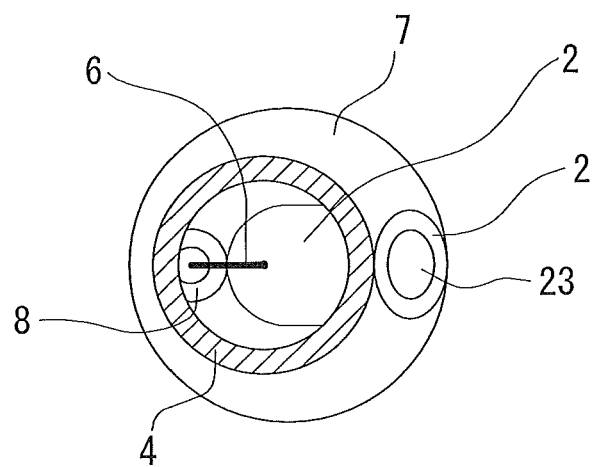
FIG. 7 is an enlarged sectional view taken along a line B-B of FIG. 2.

As shown in FIGS. 1 through 3, the distal-side tube 2 is a tubular body having the guide wire lumen 21 penetrating through the distal-side tube 2 from its distal end to its proximal end. The distal-side tube 2 has a distal portion formed by a distal-end member 25 fixed to the distal end thereof and has a distal-end opening 24. The distal portion formed by the distal-end member 25 may be formed integrally with the distal-side tube 2. The proximal end of the distal-side tube 2 is fixed to the distal end of the proximal-side tube. The stent delivery device has the proximal-side opening 23 at the proximal portion (proximal end in this embodiment) of the distal-side tube 2. As shown in FIG. 3, the proximal portion of the distal-side tube 2 is curved. As shown in FIGS. 3 and 7, the proximal-side opening 23 is formed obliquely so that it inclines toward the proximal side of the stent delivery device. Thereby it is easy to guide the guide wire.

As shown in the drawings, the distal-side tube 2 is a tubular body having the guide wire lumen 21 penetrating the distal-side tube 2 from its distal end to proximal end. The outer diameter of the distal-side tube 2 is favorably in the range of 0.3 to 2.0 mm and more favorably in the range of 0.5 to 1.5 mm. The inner diameter of the distal-side tube 2 is favorably in the range of 0.2 to 1.5 mm and more favorably in the range of 0.3 to 1.2 mm. The length of the distal-side tube 2 is favorably in the range of 20 to 600 mm and more favorably in the range of 30 to 350 mm.

It is preferable that the distal-end member 25 is disposed at the side distal from the distal end of the stent accommodation cylindrical member 5 and tapered toward its distal end to gradually decrease its diameter, as shown in FIG. 3. This configuration facilitates insertion of the stent delivery device into the stenosed portion. It is preferable that the distal-side tube 2 is provided with a stopper, disposed at the side distal from the stent 3, for preventing a movement of the stent accommodation cylindrical member 5 toward the distal end of the stent delivery device. In this embodiment, the proximal end of the distal-end member 25 is capable of contacting the distal end of the stent accommodation cylindrical member 5 and functions as the above-described stopper.

The outer diameter of the distal end of the distal-end member 25 is preferably in the range of 0.5 to 1.8 mm. The outer diameter of the distal-end member 25 at a portion thereof having the maximum diameter is preferably in the range of 0.8 to 4.0 mm. The length of the tapered distal-end member 25 is preferably in the range of 2.0 to 20.0 mm.

As shown in FIG. 3, the distal-side tube 2 has the stent-locking portion 22 for preventing the stent 3 to be implanted in an organism from moving to the proximal side thereof. It is preferable that the stent-locking portion 22 is formed as an annular projected portion. The portion of the distal-side tube 2 distal from the stent-locking portion is formed as a stent accommodation portion. The outer diameter of the stent-locking portion 22 is so set that the stent-locking portion 22 is capable of contacting the proximal end of the compressed stent 3. When the stent accommodation cylindrical member 5 moves to the proximal side of the stent delivery device, the stent-locking portion 22 keeps the position of the stent 3. Thereby the stent 3 is discharged from the stent accommodation cylindrical member 5.

It is preferable that the outer diameter of the stent-locking portion 22 is in the range of 0.8 to 4.0 mm. It is preferable that the stent-locking portion 22 is formed as an annularly projected portion, as shown in the drawing. Provided that the stent-locking portion restricts the movement of the stent 3 and is capable of pressing the stent 3 out of the stent delivery device, the stent-locking portion may be formed integrally with the distal-side tube 2 or as one or a plurality of projections separate from the distal-side tube. In addition, the stent-locking portion 22 may be made of an x-ray contrast material separate from the distal-side tube. Thereby the position of the stent can be accurately grasped, and maneuver can be accomplished easily. As the x-ray contrast material, gold, platinum, platinum-iridium alloy, silver, stainless steel, and alloys of these metals are used. To form the projected portion as the stent-locking portion, a wire made of the x-ray contrast material is wound around the outer surface of the inner tube or a pipe made of the x-ray contrast material is caulked or bonded to the outer surface of the inner tube.

As the material for forming the distal-side tube, materials having a proper degree of hardness and flexibility can be preferably used. Thus the following substances are used: polyolefins such as polyethylene, polypropylene; polyamide; polyester such as polyethylene terephthalate; fluorine-containing polymer such as ETFE; PEEK (polyether ether ketone), and polyimide. Of the above-described resin, thermoplastic resin is preferable. Resin compatible with organisms and especially thrombosis-resistant may be applied to the outer surface of the distal-side tube exposed to the outside. The following thrombosis-resistant substances can be preferably used: polyhydroxyethyl methacrylate, hydroxyethyl methacrylate-styrene copolymers (for example, HEMA-St-HEMA block copolymer).

When the distal-end member is composed of a material separate from that of the tube, it is preferable to use the following flexible materials: synthetic resin elastomers such as olefin elastomers (for example, polyethylene elastomer, polypropylene elastomer), polyamide elastomer, styrene elastomers, (for example, styrene-butadiene-styrene copolymer, styrene-isoprene-styrene copolymer, styrene-ethylene-butylene-styrene copolymer), polyurethane, urethane elastomers, fluororesin elastomers; rubbers including synthetic rubber such as urethane rubber, silicone rubber, butadiene rubber, and natural rubber such as Latex rubber.

Figure 4:
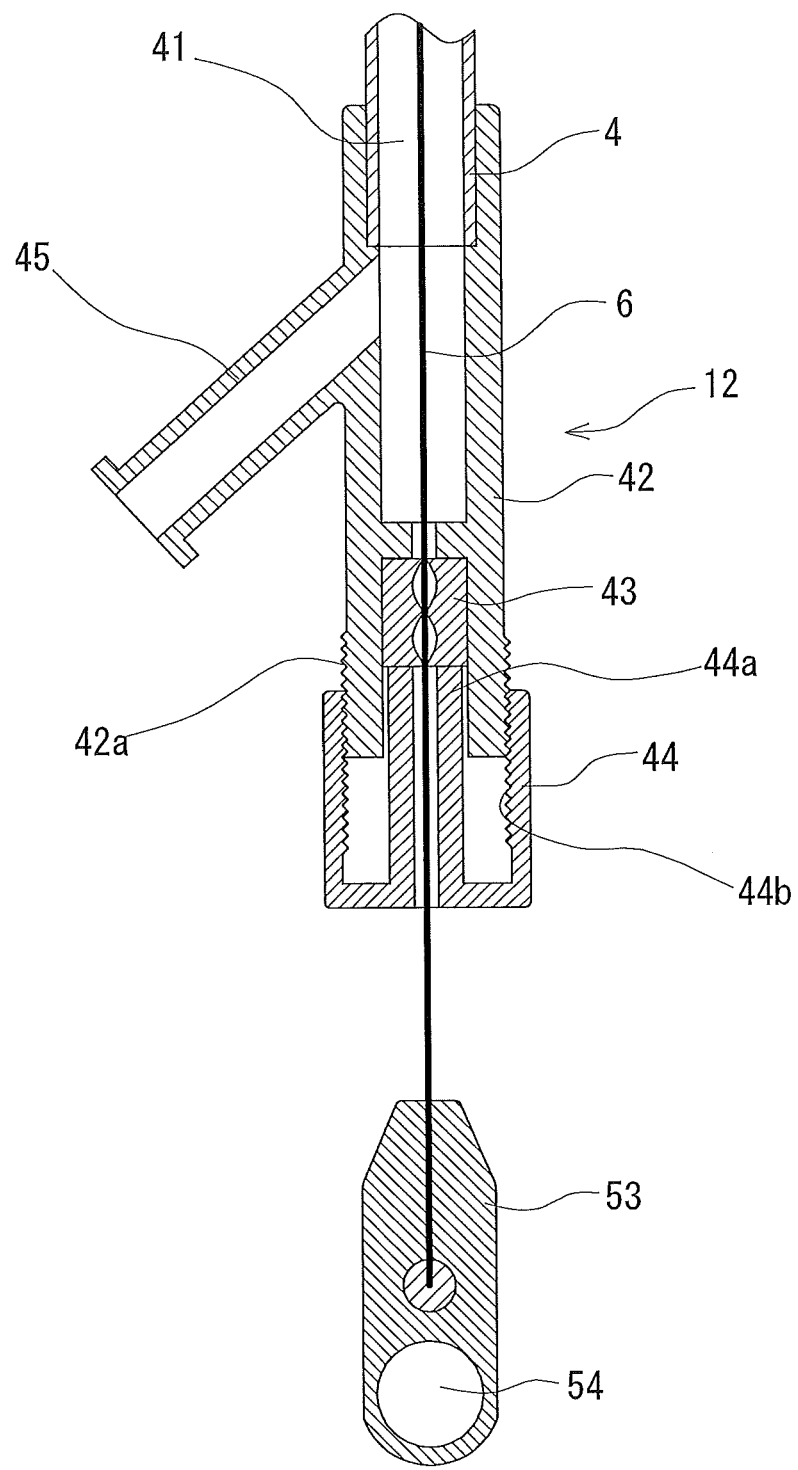
FIG. 4 is an enlarged sectional view showing the neighborhood of a proximal portion of the stent delivery device shown in FIG. 1.

As shown in FIGS. 2, 4, and 7, the proximal-side tube 4 is a tubular body extending from its distal end to proximal end. The proximal-side tube 4 has a hub 12 fixed to its proximal end. The distal portion of the proximal-side tube 4 is joined with the proximal portion of the distal-side tube 2. The proximal-side tube 4 has therein a lumen 41 into which the pulling member 6 can be inserted.

The length of the proximal-side tube 4 is favorably in the range of 300 to 1500 mm and more favorably in the range of 1000 to 1300 mm. The outer diameter of the proximal-side tube 4 is favorably in the range of 0.5 to 1.5 mm and more favorably in the range of 0.6 to 1.3 mm. The inner diameter of the proximal-side tube 4 is favorably in the range of 0.3 to 1.4 mm and more favorably in the range of 0.5 to 1.2 mm.

The outer diameter of the proximal-side tube 4 is set shorter than that of the intermediate tube which is described later by favorably 0.1 to 2.5 mm and more favorably 0.3 to 1.5 mm.

The outer diameter of the proximal-side tube 4 is set smaller than that of the portion, having a maximum diameter, which is disposed in the region of the stent delivery device 1 distal from the proximal-side tube 4. More specifically, in this embodiment, the outer diameter of the proximal-side tube 4 is set smaller than the maximum outer diameter of the portion where the distal-side tube 2 and the proximal-side tube 4 are fixed to each other. It is preferable that the outer diameter of the proximal-side tube is smaller than that of the stent accommodation cylindrical member 5. As shown in FIGS. 2, 3, and 7, in this embodiment, the distal portion of the proximal-side tube 4 is fixed to the proximal portion of the distal-side tube 2 by shifting the axis of the proximal-side tube 4 in a direction away from the proximal-side opening 23 with respect to the axis of the distal-side tube 2. Therefore by disposing the guide wire extended from the proximal-side opening 23 along the outer surface of the proximal-side tube 4 which is the extension of the proximal-side opening 23, it is possible to decrease the outer diameter of the stent delivery device 1 at its distal side including the guide wire. Thus it is possible to make the operability of the guiding wire favorable inside a guide catheter which is used in an operation and use the guiding catheter having a small diameter.

The interval between the axis of the proximal-side tube 4 and that of the distal-side tube 2 is in the range of favorably 0.1 to 2.0 mm and more favorably 0.5 to 1.5 mm.

As the material for forming the proximal-side tube, it is preferable to use materials having a proper degree of hardness and flexibility. The following substances can be preferably used: polyolefins such as polyethylene, polypropylene; nylon, polyethylene terephthalate; fluorine-containing polymer such as ETFE; PEEK (polyether ether ketone), and polyimide. Resin compatible with organisms and especially thrombosis-resistant may be applied to the outer surface of the distal-side tube. The following thrombosis-resistant substances can be preferably used: polyhydroxyethyl methacrylate, hydroxyethyl methacrylate-styrene copolymers (for example, HEMA-St-HEMA block copolymer). As the material for forming the proximal-side tube, it is preferable to use materials having a comparatively high rigidity. It is possible to use metal such as Ni—Ti, brass, stainless steel, aluminum, and the like; and resin having a comparatively high rigidity such as polyimide, vinyl chloride, polycarbonate, and the like.

The stent delivery device 1 of this embodiment has the intermediate tube 7 which encloses the proximal side of the distal-side tube 2 and the proximal side of the stent accommodation cylindrical member 5 and is fixed at the proximal portion thereof to the proximal portion of the distal-side tube 2 and the distal portion of the proximal-side tube 4. In the stent delivery device 1 of this embodiment, the intermediate tube 7 encloses the proximal side of the distal-side tube 2 and the proximal side of the stent accommodation cylindrical member 5 without preventing the stent accommodation cylindrical member 5 from moving toward the proximal side of the stent delivery device 1. One end portion of the pulling member 6 is fixed to the stent accommodation cylindrical member 5 inside the intermediate tube 7. The pulling member 6 passes the gap between the intermediate tube 7 and the distal-side tube 2 and extends into the proximal-side tube 4. Thereby the pulling wire is not exposed.

The proximal portion of the distal-side tube 2 extends inside the intermediate tube 7 and is exposed from the proximal end of the intermediate tube 7. The distal portion of the proximal-side tube 4 penetrates into the proximal portion of the intermediate tube 7. The distal-side tube 2, the proximal-side tube 4, and the intermediate tube 7 are liquid-tightly fixed to the proximal portion of the intermediate tube 7. The lumen 41 inside the proximal-side tube 4 communicates with the inside of the intermediate tube 7. As shown in FIGS. 2 and 3, the distal portion of the intermediate tube 7 is decreased in its diameter or curved. It is preferable that the distal end of the intermediate tube 7 liquid-tightly contacts the outer surface of the stent accommodation cylindrical member 5 without preventing the movement of the stent accommodation cylindrical member 5. But the distal end of the intermediate tube 7 does not necessarily have to contact the outer surface of the stent accommodation cylindrical member 5.

As the material for forming the intermediate tube, it is preferable to use materials having a proper degree of hardness and flexibility. The following substances can be preferably used: polyolefins such as polyethylene, polypropylene; nylon, polyethylene terephthalate; fluorine-containing polymer such as ETFE; PEEK (polyether ether ketone), and polyimide. Of the above-described resin, thermoplastic resin is preferable. Resin compatible with organisms and especially thrombosis-resistant may be applied to the outer surface of the intermediate tube. The following thrombosis-resistant substances can be preferably used: polyhydroxyethyl methacrylate, hydroxyethyl methacrylate-styrene copolymers (for example, HEMA-St-HEMA block copolymer).

The stent delivery device 1 has the pulling member 6 extending inside the proximal-side tube 4, with one end portion thereof fixed to the stent accommodation cylindrical member 5. The pulling member 6 is pulled toward the proximal side of the proximal-side tube 4 to move the stent accommodation cylindrical member 5 toward the proximal side of the stent delivery device 1.

In the stent delivery device 1 of this embodiment, the pulling member 6 is composed of a pulling wire. As shown in FIGS. 1, 2, and 4, the pulling member 6 penetrates through the proximal-side tube 4 and extends to the outside from the proximal end of the proximal-side tube 4.

A twisted wire material or a plurality of twisted wire materials can be preferably used as the material for composing the pulling wire. The diameter of the pulling wire is in the range of favorably 0.01 to 0.55 mm and more favorably 0.1 to 0.3 mm.

As the material for forming the pulling member 6, the following substances can be used: stainless steel wire (preferably, high tensile stainless wire for spring); music wire (preferably, nickel-plated or chromium-plated music wire); super-elastic alloy wire; wires made of metal such as Ni—Ti alloy, Cu—Zn alloy, Ni—Al alloy, tungsten, tungsten alloy, titanium, titanium alloy, cobalt alloy; tantalum, comparatively high rigidity polymeric materials such as polyamide, polyimide, ultra-high-molecular-weight polyethylene, polypropylene, and fluororesin; and combinations of these substances.

Resin having low frictional property which increases lubricity may be applied to the side surface of the pulling member. As the resin having low frictional property, it is possible to use fluororesin, nylon 66, polyether ether ketone, high-density polyethylene, and the like. Above all, the fluororesin is particularly favorable. As the fluororesin, polytetrafluoroethylene, polyvinylidene fluoride, ethylenetetrafluoroethylene, perfluoroalkoxy resin, and the like are preferable. The side surface of the pulling member may be coated with silicone or hydrophilic resin.

An operating member 53 fixed to the proximal portion of the pulling member 6 is so formed as to enclose the proximal portion of the pulling member 6 and a bulged portion formed at the proximal end thereof. The operating member 53 of this embodiment has a through-hole 54 into which a finger or the like can be inserted.

The stent delivery device 1 of this embodiment has the projected portion (in this embodiment, tubular member though which wire penetrates) 8 provided on the outer surface of the distal-side tube 2 at its proximal side. The projected portion 8 is capable of moving inside the slit 52 of the stent accommodation cylindrical member 5. The distal end of the projected portion 8 is disposed inside the proximal portion of the slit 52. The projected portion 8 prevents the stent accommodation cylindrical member 5 from rotating on the axis thereof when the stent delivery device 1 is operated. Because the slit 52 extends toward the distal side of the stent delivery device, the slit 52 guides a linear movement for the stent accommodation cylindrical member 5 without preventing the movement of the stent accommodation cylindrical member 5 toward the proximal side of the stent delivery device. The projected portion (in this embodiment, tubular member though which wire penetrates) 8 is fixed to the outer surface of the distal-side tube 2, but may be fixed to the inner surface of the intermediate tube 7. The projected portion 8 may be extended from the distal end of the proximal-side tube to the distal side thereof. The stent delivery device 1 of this embodiment has a movement distance restriction portion for restricting a movement distance of the stent accommodation cylindrical member 5 toward the proximal side of the stent delivery device. More specifically, owing to the movement of the stent accommodation cylindrical member 5 toward the proximal side of the stent delivery device, the projected portion (in this embodiment, tubular member though which wire penetrates) 8 contacts the distal end of the slit 52, thus preventing a further movement of the stent accommodation cylindrical member 5 toward the proximal side of the stent delivery device.

The stent delivery device 1 of this embodiment has a member for holding the position of the pulling member. This member is disposed on the outer surface of the distal-side tube 2 and has a passage through which the pulling member 6 is capable of penetrating. The stent delivery device of this embodiment has a tubular member 8 displaying the function of the member for holding the position of the pulling member and the function of the above-described projected portion. The pulling member 6 can be pulled favorably by the member for holding the position of the pulling member. It is preferable that the member for holding the position of the pulling member is disposed on an extension of a fixing portion 6d, at the proximal side thereof, where the pulling member 6 and the stent accommodation cylindrical member 5 are fixed to each other. As the member for holding the position of the pulling member, it is possible to use members having the passage through which the pulling member 6 is capable of penetrating. For example, it is possible to use a ring-shaped member, a ring-shaped member having a cut-out, and a trough-shaped member. It is preferable to use a plurality of the ring-shaped members.

As the tubular member 8, a tube having a lumen whose outer diameter is larger than that of the pulling member therein is used. The length of the tubular member 8 is favorably in the range of 10 to 180 mm and more favorably in the range of 15 to 120 mm. The outer diameter of the tubular member is favorably in the range of 0.15 to 0.8 mm and more favorably in the range of 0.2 to 0.5 mm. It is favorable that the inner diameter of the tubular member is larger than the outer diameter of the pulling member by 0.05 to 0.2 mm.

It is preferable that the member for holding the position of the pulling member is fixed to the outer surface of the distal-side tube 2. But the member for holding the position of the pulling member may be fixed to the inner surface of the distal-side tube 2. Further the member for holding the position of the pulling member may be extended to the side distal from the distal end of the proximal-side tube 4. Furthermore resin having low frictional property increasing lubricity may be applied to the inner surface of the member for holding the position of the pulling member.

As shown in FIGS. 1, 2, and 4, the hub 12 is fixed to the proximal portion of the proximal-side tube 4. The hub 12 has a body 42 and a valve 43 accommodated inside the body 42 to hold the pulling member 6 slidably and liquid-tightly. The hub 12 has a side port 45 branching obliquely and rearward from a portion of the body 42 in the vicinity of the center thereof. The hub 12 has an inner tube locking mechanism for preventing the movement of the pulling member 6. In this embodiment, the inner tube locking mechanism has the valve 43 liquid-tightly sandwiching the proximal portion of the pulling member 6 by compression, an operation member 44 for compressing the valve 43, and the body 42. The locking mechanism prevents the pulling member 6 from being pulled inadvertently. The valve 43 is mounted in a valve accommodation concave portion provided at the proximal portion of the body 42. A pulling member insertion passage is formed inside the valve 43. Even though the valve 43 is not compressed, it holds the gap between it and the pulling member liquid-tightly and prevents flow-out of blood. The valve of this embodiment has an inner configuration (in other words, configuration of inner tube insertion passage) formed by a partial overlapping of two approximately spheres in the axial direction of the hub 12. The diameters of both ends of the valve 43 and the central portion thereof are reduced.

The operation member 44 has a cylindrical pressing portion 44a projected at the central portion of the hub 12 toward the distal side of the stent delivery device, a screwing portion 42a formed on the outer surface of the rear end of the body 42, and a screwing portion 44b capable of screwing the screwing portion 42a. The pulling member insertion passage is formed inside the pressing portion 44a. As shown in FIG. 4, the distal-side portion of the pressing portion 44a penetrates into the valve accommodation concave portion, thus compressing the valve 43 owing to the movement of the operation member toward the distal end of the hub 12.

In the locking mechanism, when screwing is progressed to move the operation member 44 toward the distal side of the hub 12 by rotating the operation member 44, the distal end of the valve-pressing portion 44a presses the rear end of the valve 43. When the screwing is further progressed by rotating the operation member 44, the valve 43 is compressed axially. As the valve 43 is compressed, the valve contacts the pulling member 6 closely, thus holding the pulling member 6 and fixing it thereto. The locking mechanism is released by rotating the operation member 44 in an opposite direction.

Figure 8:
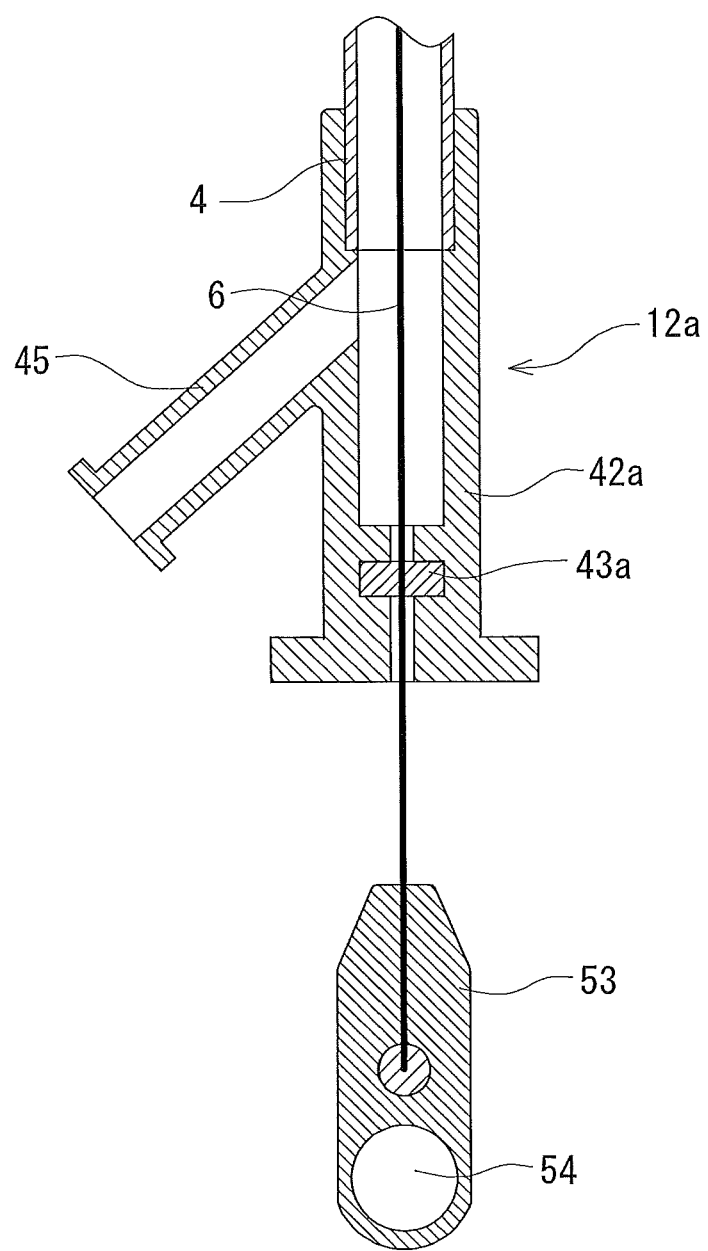
FIG. 8 is an enlarged sectional view showing the neighborhood of a proximal portion of a stent delivery device of another embodiment of the present invention.

It is preferable that the stent delivery device has the hub provided with the above-described locking mechanism. But a hub 12a may not have a locking mechanism as shown in FIG. 8. A hub body 42a accommodates a sealing member 43a which allows the pulling member 6 to slidably move in a liquid-tight state. The sealing member 43a is unmovable.

As materials for forming the hub body 42, 42a and the operation member 44, it is possible to use the following rigid or semi-rigid materials: synthetic resin including polycarbonate, polyolefins (for example, polyethylene, polypropylene, ethylene-propylene copolymer), styrene resin, for example, polystyrene, MS resin such as methacrylate-styrene copolymer, MBS resin such as methacrylate-butylene-styrene copolymer, polyester; and metal such as stainless steel, aluminum, and aluminum alloy.

As the material for forming the valve 43 and the sealing member 43a, the following elastic materials are used: rubbers including synthetic rubber such as urethane rubber, silicone rubber, butadiene rubber, and natural rubber such as Latex rubber; synthetic resin elastomers such as olefin elastomers (for example polyethylene elastomer, polypropylene elastomer), polyamide elastomer, styrene elastomers, (for example, styrene-butadiene-styrene copolymer, styrene-isoprene-styrene copolymer, styrene-ethylenebutylene-styrene copolymer), polyurethane, urethane elastomers, fluororesin elastomers.

The method of using the stent delivery device 1 of the present invention is described below with reference to the drawings.

In most cases, initially as shown in FIGS. 1 and 2, one end of the guide wire implanted in a human body is inserted into the opening 24 of the distal-end member 25 to expose the guide wire (not shown) from the proximal-side opening 23. Thereafter the guide wire is inserted into a guide catheter (not shown) disposed in the human body. Thereafter the stent delivery device 1 is moved forward along the guide wire to dispose a stent accommodation portion of the stent accommodation cylindrical member 5 in a desired stenosed portion.

Figure 9:
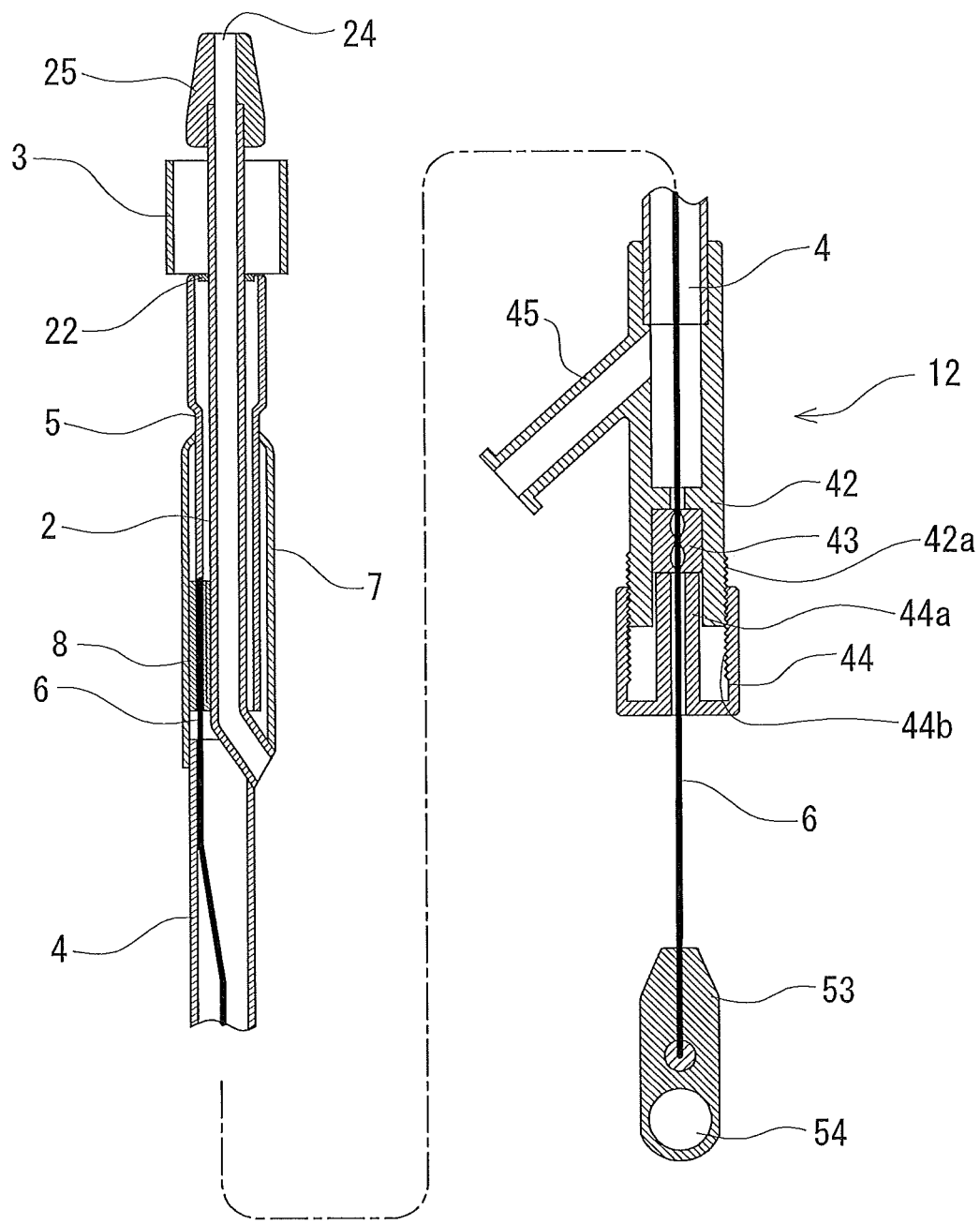
FIG. 9 is an explanatory view for explaining the operation of the stent delivery device of the present invention.

After the operation member 44 of the hub 12 of the proximal-side tube 4 is operated to release the fixed state of the pulling member 6, the operation member 44 of the pulling member 6 is pulled toward the proximal end of the stent delivery device. Thereby the stent accommodation cylindrical member 5 axially moves to the proximal side of the stent delivery device. At this time, the rear end surface of the stent 3 contacts the distal end surface of the stent-locking portion 22 of the distal-side tube 2 and is locked thereto. Thereby as the stent accommodation cylindrical member 5 moves, the stent 3 is discharged from the opening at the distal end of the stent accommodation cylindrical member 5. As shown in FIG. 9, owing to the discharge, the stent 3 self-expands, expands the stenosed portion, and is implanted therein.

A stent delivery device 10 of another embodiment of the present invention is described below.

The stent delivery device 10 is the same as the stent delivery device 1 except that the stent delivery device 10 does not have the intermediate tube and that the mode of the distal-side tube the former is different from the mode of the distal-side tube of the latter. Other construction of the former is the same as that of the latter. Thus the same parts of the former as those of the latter are denoted by the same reference numerals as those of the latter, and description thereof is omitted herein.

The stent delivery device 10 of this embodiment has a distal-side tube 2a, the proximal-side tube 4, a stent accommodation cylindrical member 5a, the stent 3, and the pulling member 6.

Figure 10:
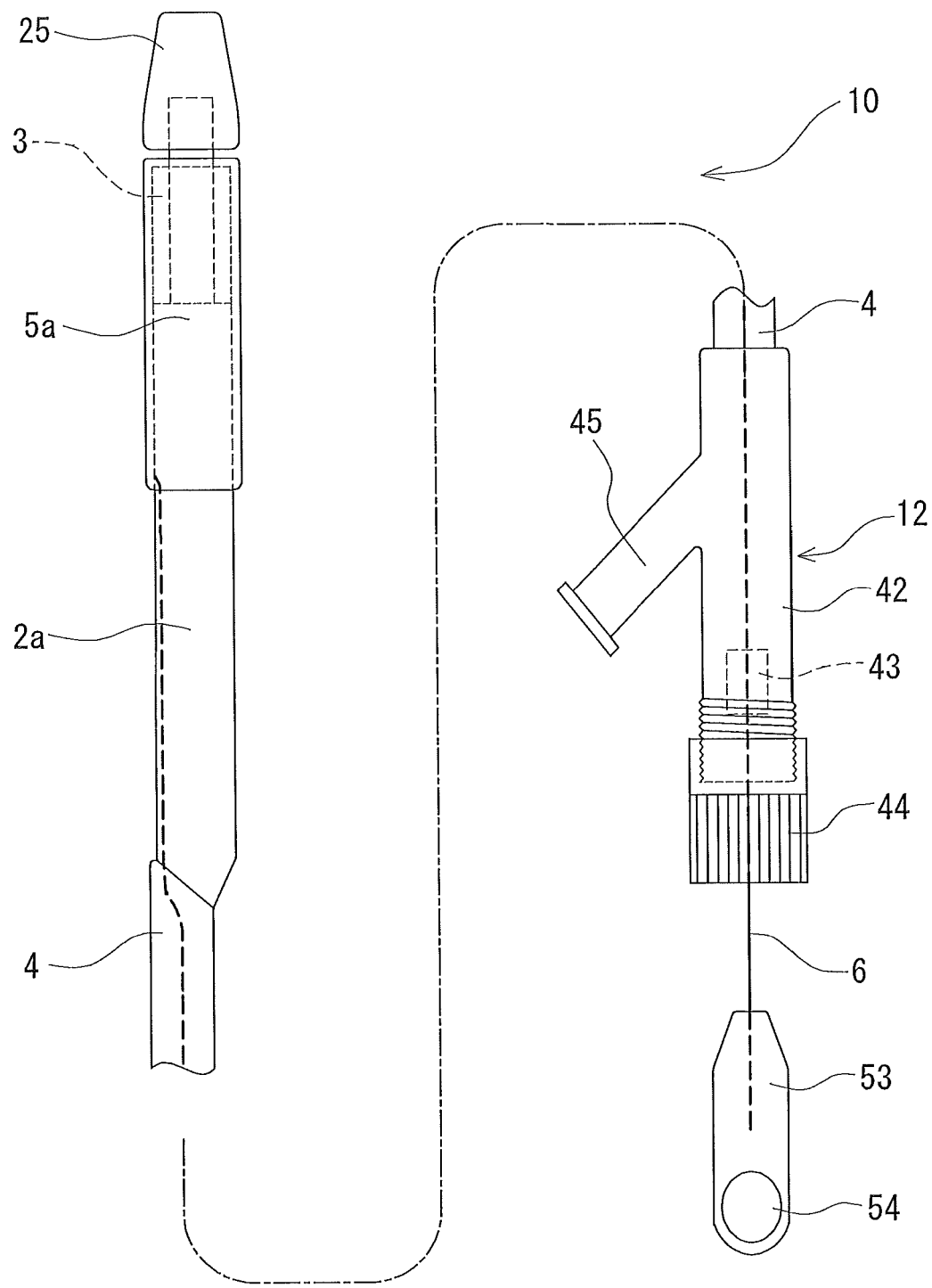
FIG. 10 is a partially schematic enlarged outlook view showing a stent delivery device of another embodiment of the present invention.
Figure 11:
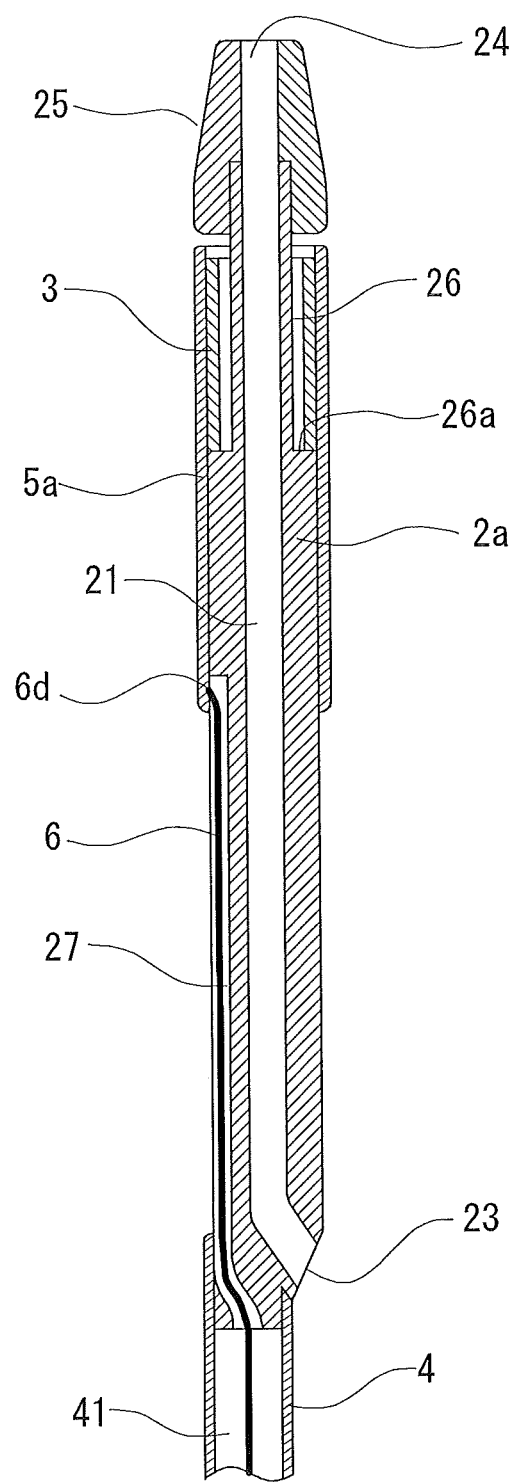
FIG. 11 is an enlarged sectional view showing the neighborhood of a distal portion of the stent delivery device shown in FIG. 10.
Figure 16:
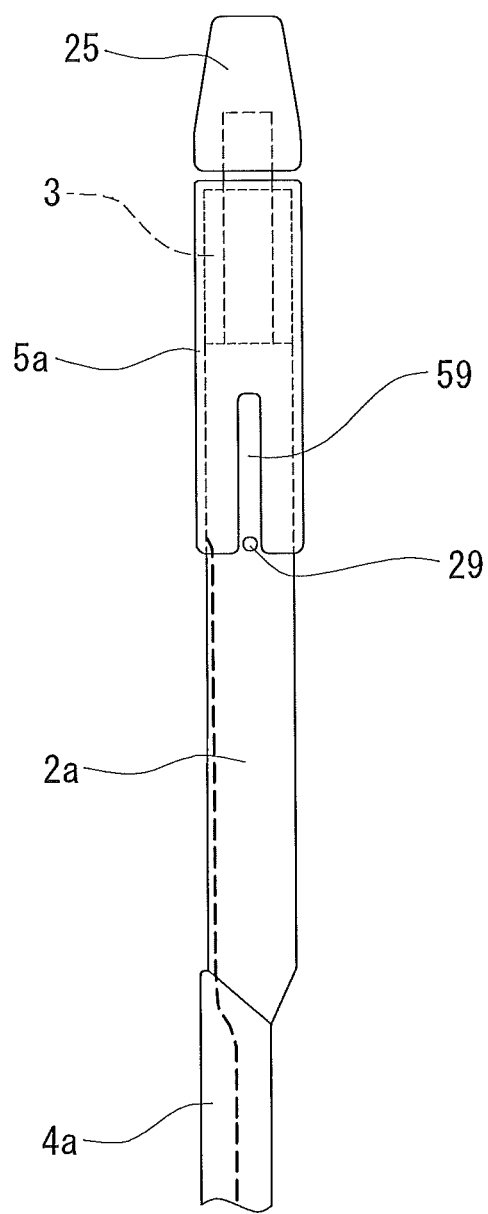
FIG. 16 is an enlarged outlook view showing a distal portion of a stent delivery device of another embodiment of the present invention.

As shown in FIGS. 10 and 11, as the stent accommodation cylindrical member 5a, a cylindrical member having almost the same diameter is used. A slit 59 as shown in FIG. 16 may be formed in the stent accommodation cylindrical member 5a. As shown in FIG. 16, a projected portion 29 formed on the outer surface of the distal-side tube is capable of advancing into the slit 59. In this embodiment, until the distal end of the slit 59 contacts the projected portion 29, the stent accommodation cylindrical member 5a is movable toward the proximal side of the stent delivery device. Thus the length of the slit 59 is set equally to or a little longer than the length in the range from the proximal end of the stent 3 accommodated in the stent accommodation cylindrical member 5a to the distal end of the stent accommodation cylindrical member 5a.

Materials similar to those for the stent accommodation cylindrical member 5 are used to form the stent accommodation cylindrical member 5a. It is preferable to treat the outer surface of the stent accommodation cylindrical member 5a so that the outer surface thereof is lubricant. The treatment is made in the above-described manner. To make the lubricity of the stent 3 preferable, the above-described material may be applied or fixed to the inner surface of the stent accommodation cylindrical member 5a.

The stent 3 is accommodated at the distal portion of the stent accommodation cylindrical member 5a. The stent 3 is the same as that described above.

As shown in FIGS. 10 and 11, the distal-side tube 2a is a tubular body having the guide wire lumen 21 penetrating through the distal-side tube 2a from its distal end to its proximal end. The distal-side tube 2a has a distal portion formed by a distal-end member 25 fixed to the distal end thereof and has a distal-end opening 24. The distal portion formed by the distal-end member 25 may be formed integrally with the distal-side tube 2a. The proximal end of the distal-side tube 2a is fixed to the distal end of the proximal-side tube. The guide wire lumen 21 bends at the proximal portion thereof. The stent delivery device has the proximal-side opening 23 at the proximal portion (proximal end in this embodiment) of the distal-side tube 2a. As shown in FIG. 11, the proximal portion of the distal-side tube 2a is curved. As shown in FIGS. 3 and 7, the proximal-side opening 23 is formed obliquely so that it inclines toward the proximal side of the stent delivery device. Thereby it is easy to guide the guide wire.

The outer diameter of the distal-side tube 2a is favorably in the range of 0.5 to 3.0 mm and more favorably in the range of 1.0 to 2.5 mm. The inner diameter of the distal-side tube 2a is favorably in the range of 0.2 to 1.5 mm and more favorably in the range of 0.3 to 1.2 mm. The length of the distal-side tube 2a is favorably in the range of 20 to 600 mm and more favorably in the range of 30 to 350 mm.

As shown in FIG. 11, the distal-side tube 2a has a stent-disposing small-diameter portion 26. The stent-locking portion for preventing the stent 3 to be implanted in the organism from moving to the proximal side thereof is constructed of a proximal end 26a of the stent-disposing small-diameter portion 26. The outer diameter of the proximal end 26a of the stent-disposing small-diameter portion 26 is so set that the stent-locking portion 22 is capable of contacting the proximal end of the compressed stent 3. When the stent accommodation cylindrical member 5a moves to the proximal side of the stent delivery device, the proximal end 26a keeps the position of the stent 3. Thereby the stent 3 is discharged from the stent accommodation cylindrical member 5a.

In this embodiment, the outer diameter of the proximal-side tube 4 is also set smaller than that of the portion, having the maximum diameter, which is disposed in the region of the stent delivery device 10 distal from the proximal-side tube 4. More specifically, in this embodiment, the stent accommodation cylindrical member 5a has the maximum outer diameter. The outer diameter of the proximal-side tube 4 is set smaller than the outer diameter of the stent accommodation cylindrical member 5a. As shown in FIGS. 10 and 11, in this embodiment, the distal portion of the proximal-side tube 4 is fixed to the proximal portion of the distal-side tube 2a by shifting the axis of the proximal-side tube 4 in a direction away from the proximal-side opening 23 with respect to the axis of the distal-side tube 2a.

The distal-side tube 2a extends from the vicinity of the fixing point 6d at which the pulling member 6 and the stent accommodation cylindrical member 5a are fixed to each other to the proximal side of the stent delivery device. The distal-side tube 2a has a passage 27 for the pulling member. In this embodiment, the passage 27 for pulling member is formed of a concave portion extended axially on the outer surface of the distal-side tube 2a. The passage 27 for the pulling member may be a lumen extended in penetration through the wall of the distal-side tube 2a.

Figure 12:
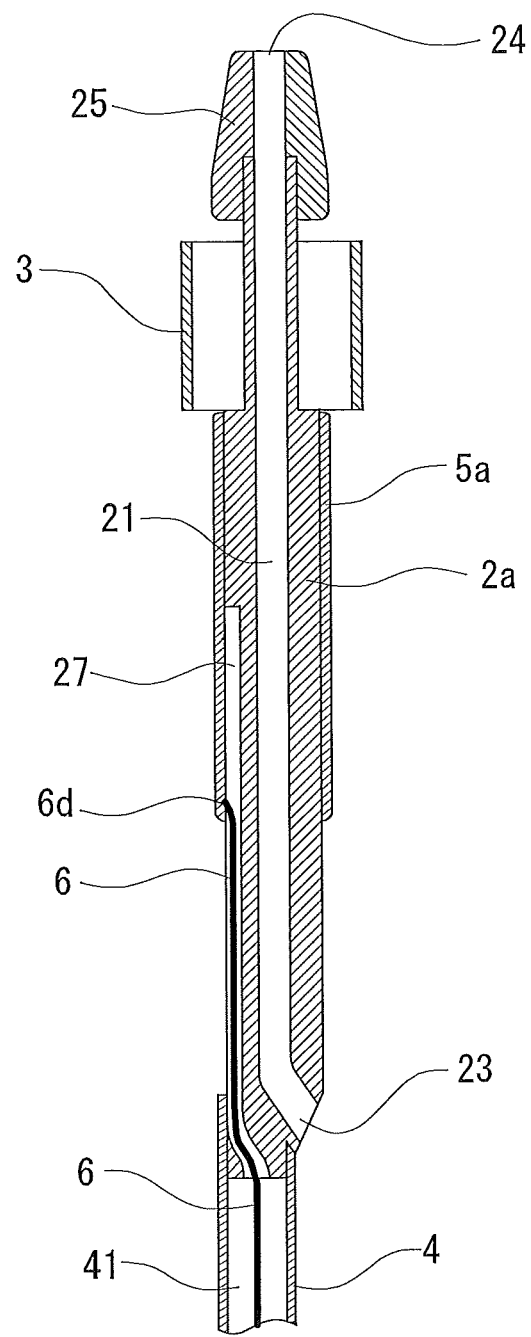
FIG. 12 is an explanatory view for explaining the operation of the stent delivery device shown in FIG. 10.

In the stent delivery device 10 of this embodiment, by pulling the operation member 53 of the pulling member 6 toward the proximal end of the stent delivery device, the stent accommodation cylindrical member 5a axially moves to the proximal side of the stent delivery device. At this time, the rear end surface of the stent 3 contacts the distal end surface of the stent-locking portion 22 of the distal-side tube 2a and is locked thereto. Thereby as the stent accommodation cylindrical member 5a moves, the stent 3 is discharged from the opening at the distal end of the stent accommodation cylindrical member 5a. As shown in FIG. 12, the stent 3 self-expands and expands the stenosed portion and is implanted therein.

In all the above-described embodiments, a plurality of (more specifically, two) the pulling members may be provided.

Figure 13:
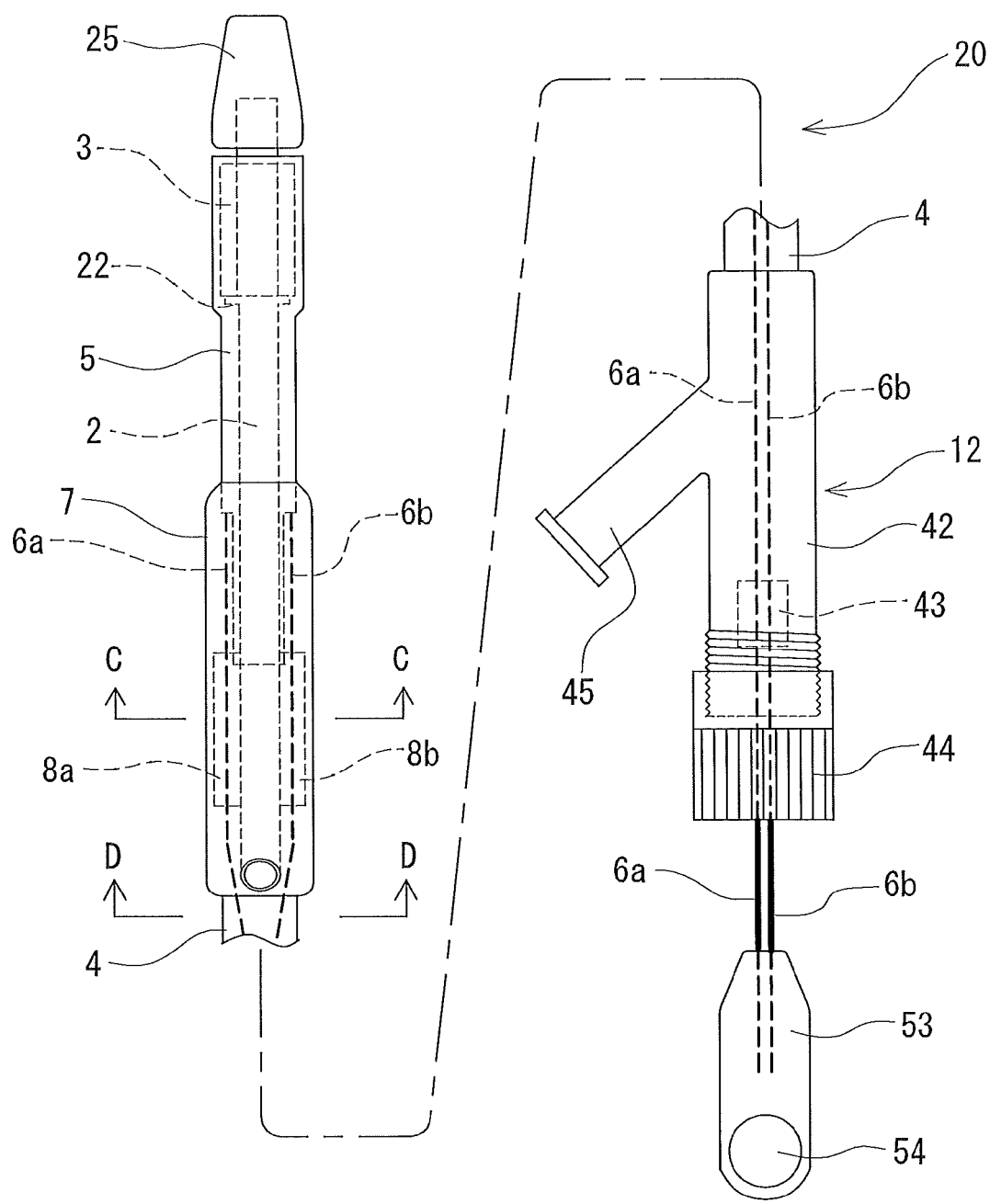
FIG. 13 is a partially schematic enlarged outlook view showing a stent delivery device of another embodiment of the present invention.
Figure 14:
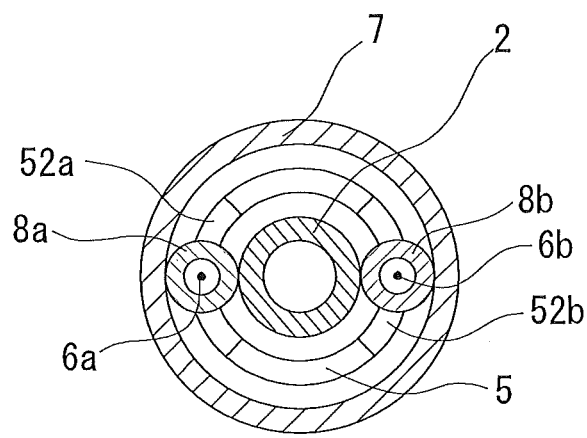
FIG. 14 is an enlarged sectional view taken along a line C-C of FIG. 13.
Figure 15:
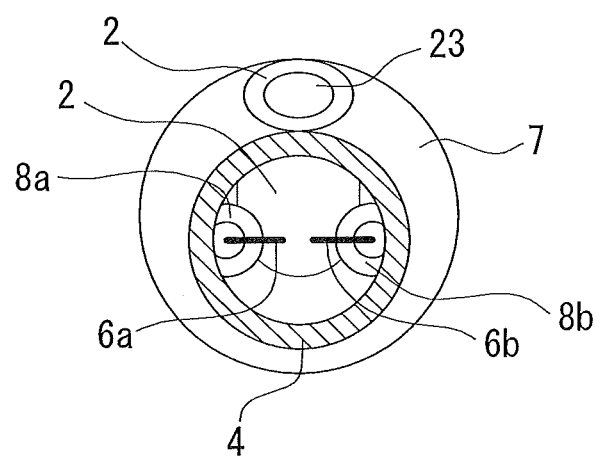
FIG. 15 is an enlarged sectional view taken along a line D-D of FIG. 13.

A stent delivery device 20 shown in FIGS. 13 through 15 has two pulling members.

FIG. 13 is a partially schematic enlarged outlook view showing a stent delivery device of another embodiment of the present invention. FIG. 14 is an enlarged sectional view taken along a line C-C of FIG. 13. FIG. 15 is an enlarged sectional view taken along a line D-D of FIG. 13.

The stent delivery device 20 is the same as the stent delivery device 1 except that the stent delivery device 20 has two pulling members and that there are some differences generated caused thereby. Other construction of the former is the same as that of the latter. Thus the same parts of the former as those of the latter are denoted by the same reference numerals as those of the latter, and description thereof is omitted herein. The above-described stent delivery device 10 may be provided with two pulling members.

As shown in FIGS. 13 and 14, the stent accommodation cylindrical member 5 of the stent delivery device 20 has two slits 52a, 52b extended from the proximal end of the stent accommodation cylindrical member 5 toward its distal end and disposed at positions opposed to each other. In correspondence to the positions of the slits 52a, 52b, the distal-side tube 2 has two tubular members 8a, 8b formed at positions opposed to each other.

Two pulling members 6a, 6b are fixed to the proximal portion of the stent accommodation cylindrical member 5 at positions opposed to each other. As shown in FIGS. 13 through 15, the pulling member 6a extends inside the proximal-side tube 4 in penetration through a tubular member 8a and fixed to the operation member 53 at the proximal portion thereof. Similarly the pulling member 6b extends inside the proximal-side tube 4 in penetration through a tubular member 8b and fixed to the operation member 53 at the proximal portion of the stent accommodation cylindrical member 5.

Figure 17:
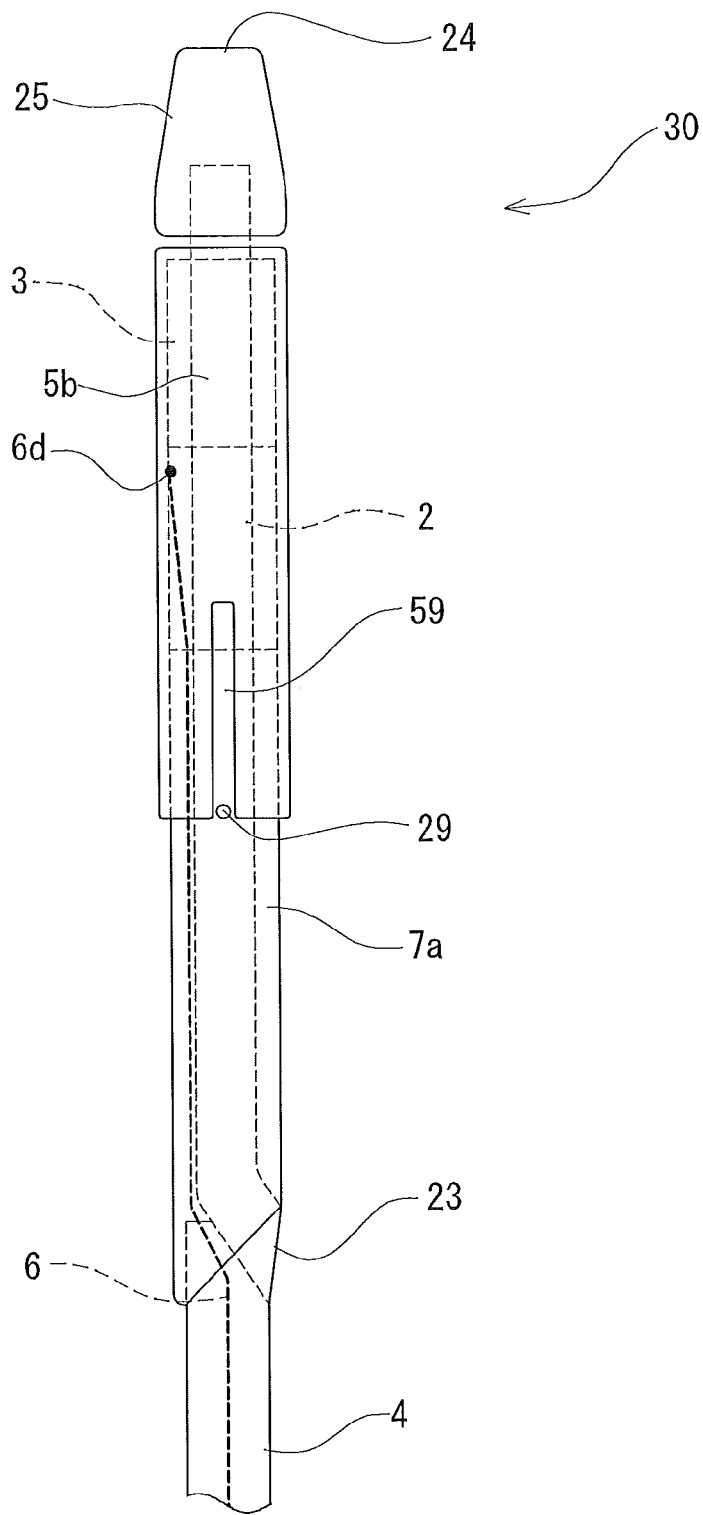
FIG. 17 is an enlarged outlook view showing a distal portion of a stent delivery device of another embodiment of the present invention.
Figure 18:
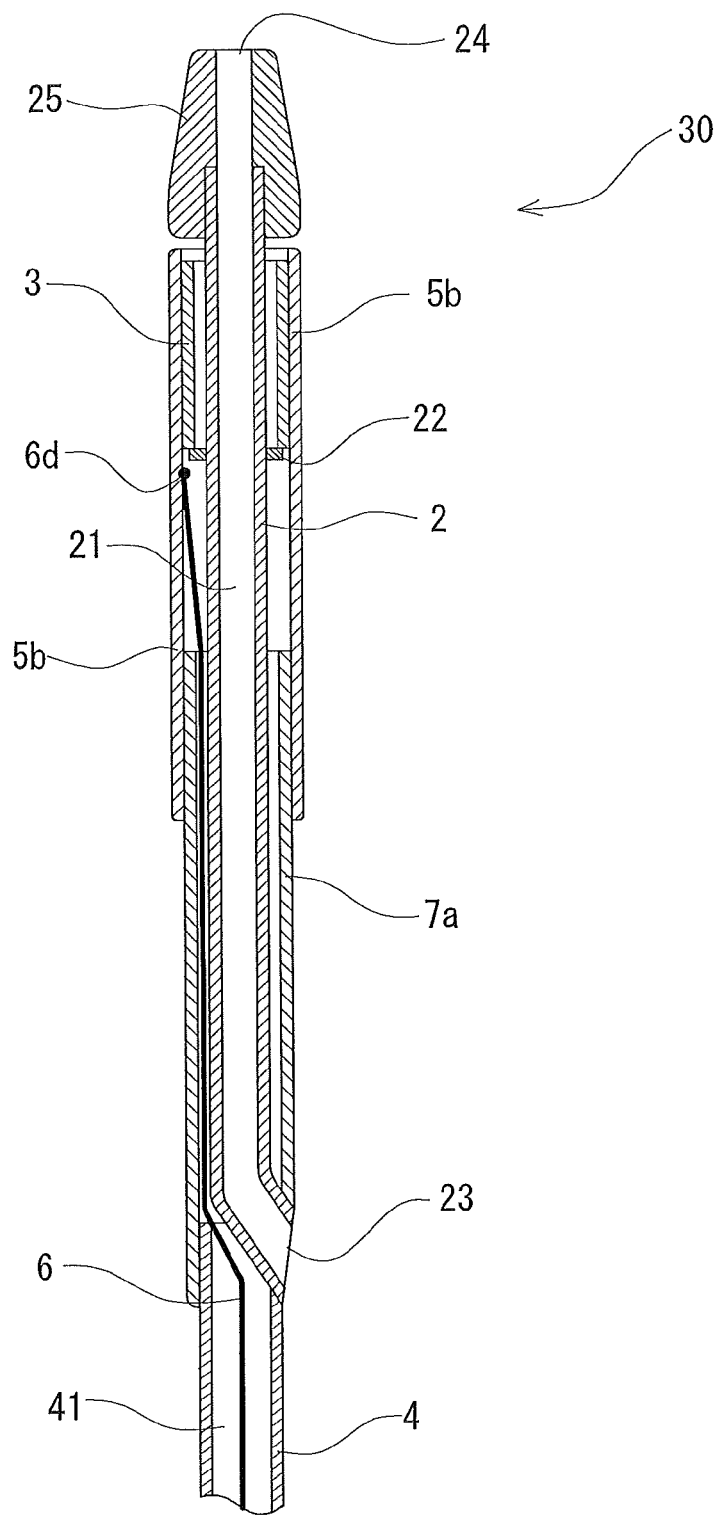
FIG. 18 is an enlarged sectional view showing the distal portion of the stent delivery device shown in FIG. 17.

The distal portion of the stent delivery device may have a construction as shown in FIGS. 17 and 18. FIG. 17 is an enlarged outlook view showing a distal portion of a stent delivery device of another embodiment of the present invention. FIG. 18 is an enlarged sectional view showing the distal portion of the stent delivery device shown in FIG. 17.

The basic construction of the stent delivery device 30 is the same as that of the stent delivery device 1 of the above-described embodiment. The stent delivery device 30 is different from the stent delivery device 1 in that in the stent delivery device 1, the stent accommodation cylindrical member 5 slides on the inner side of the intermediate tube 7, whereas in the stent delivery device 30, a stent accommodation cylindrical member 5a slides on the outer side of an intermediate tube 7a. The stent accommodation cylindrical member 5b has the same diameter over the whole length thereof. The intermediate tube 7a has also the same diameter over the whole length thereof. The outer diameter of the intermediate tube 7a is set a little smaller than the inner diameter of the stent accommodation cylindrical member 5b. Thus in the stent delivery device 30, the stent accommodation cylindrical member 5b has the largest diameter.

As described above, the distal portion of the intermediate tube 7a penetrates into the stent accommodation cylindrical member 5b from its proximal end. As shown in FIG. 18, the pulling wire 6 is fixed to the inner side of the stent accommodation cylindrical member 5 at a fixing point 69 provided at the vicinity of the stent. The proximal portion of the distal-side tube 2 and the distal portion of the proximal-side tube 4 are fixed to the proximal portion of the intermediate tube 7a.

Similarly to the stent delivery device 1, the stent accommodation cylindrical member 5b is not bonded to the intermediate tube 7a, but is movable. Although the stent accommodation cylindrical member 5b is moved to the proximal side of the stent delivery device by pulling the pulling wire 6, the stent 3 is locked to the stent-locking portion 22. Thus the stent 3 is discharged from the stent accommodation cylindrical member 5b and self-expands. Even though the entire tube is made of a soft material, this mode allows the stent to be expanded safely without being bent in a curved blood vessel or the like, because the pulling wire is disposed inside the tube.

Figure 19:
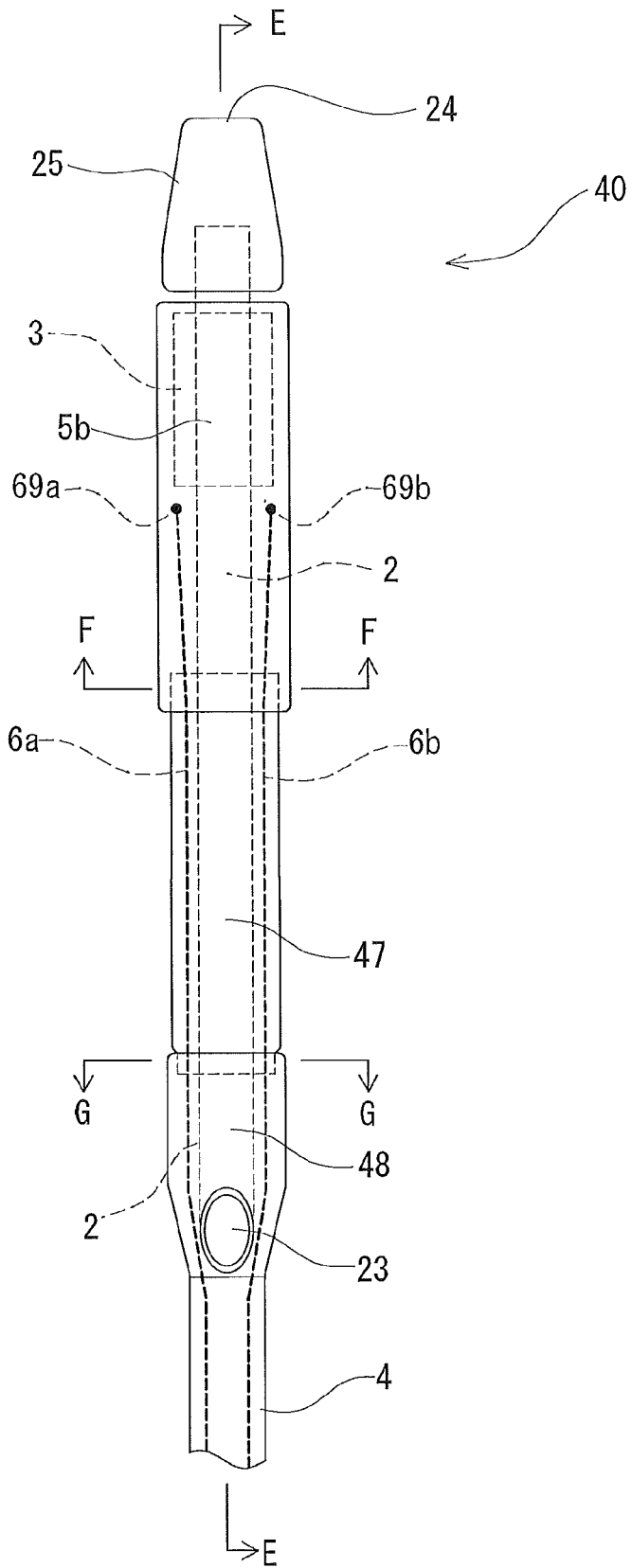
FIG. 19 is an enlarged outlook view showing a distal portion of a stent delivery device of another embodiment of the present invention.
Figure 20:
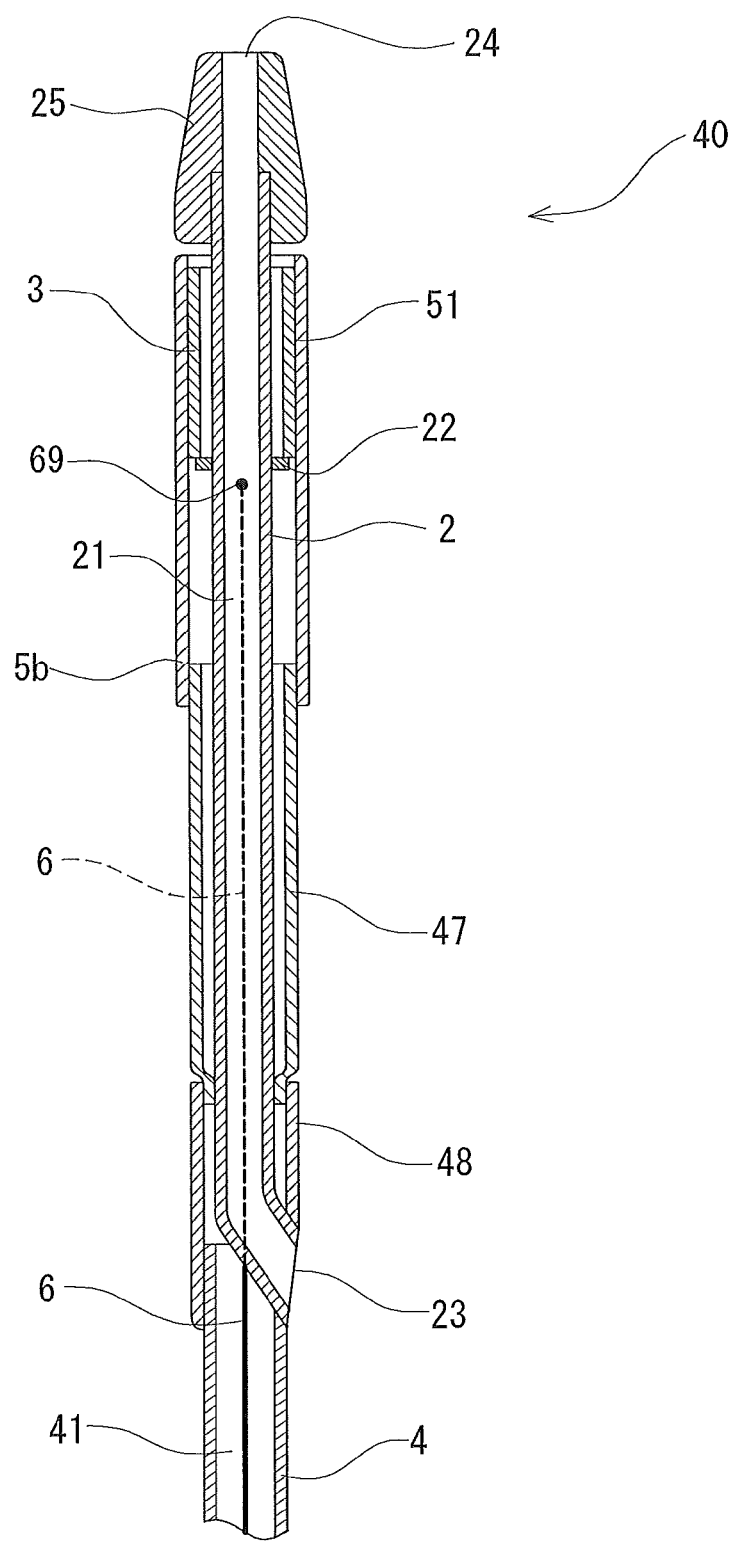
FIG. 20 is a sectional view taken along a line E-E of FIG. 19.
Figure 21:
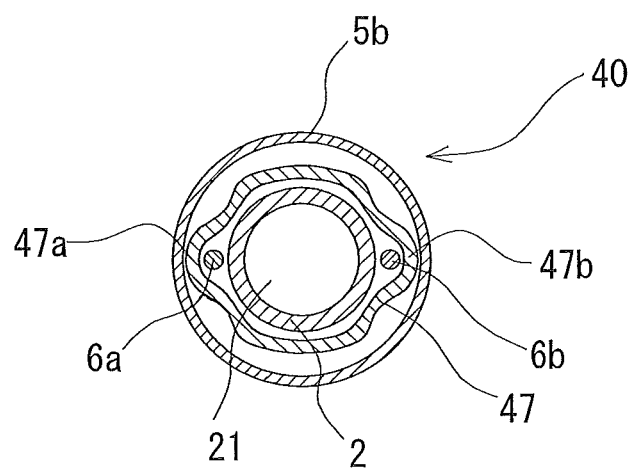
FIG. 21 is an enlarged sectional view taken along a line F-F of FIG. 19.
Figure 22:
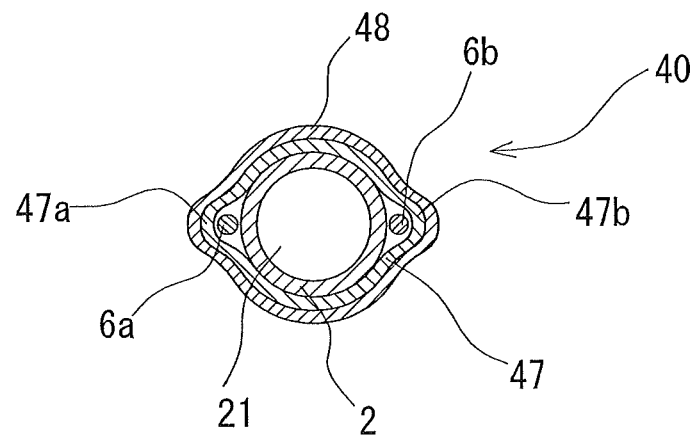
FIG. 22 is an enlarged sectional view taken along a line G-G of FIG. 19.

The distal portion of the stent delivery device may have a construction as shown in FIGS. 19 through 22. The basic construction of the stent delivery device 40 is the same as that of the above-described stent delivery device 1. FIG. 19 is an enlarged outlook view showing a distal portion of a stent delivery device of another embodiment of the present invention. FIG. 20 is a sectional view taken along a line E-E of FIG. 19. FIG. 21 is an enlarged sectional view taken along a line F-F of FIG. 19. FIG. 22 is an enlarged sectional view taken along a line G-G of FIG. 19.

The stent delivery device 40 is different from the stent delivery device 1 in that in the stent delivery device 1, the stent accommodation cylindrical member 5 slides on the inner side of the intermediate tube 7, whereas in the stent delivery device 40, a stent accommodation cylindrical member 5b slides on the outer side of an intermediate tube 47. The stent accommodation cylindrical member 5b has the same diameter over the whole length thereof. The intermediate tube 7a has also the same diameter over the whole length thereof except its proximal portion. The outer diameter of the intermediate tube 47 is set a little smaller than the inner diameter of the stent accommodation cylindrical member 5b. Thus in the stent delivery device 40, the stent accommodation cylindrical member 5b has the largest diameter.

As described above, the distal portion of the intermediate tube 47 penetrates into the stent accommodation cylindrical member 5b from its proximal end. As shown in FIGS. 19 and 20, the stent delivery device 40 has a plurality of (two) pulling wires 6a, 6b. The pulling members 6a, 6b are fixed to the inner side of the stent accommodation cylindrical member 5b at fixing points 69a, 69b respectively. The pulling wires 6a, 6b are disposed at positions substantially opposed to each other. The fixing points 69a, 69b are disposed at positions substantially opposed to each other.

As shown in FIG. 21, an intermediate tube 47 has axially extended bulged portions 47a, 47b for accommodating the pulling wire. The bulged portions 47a, 47b are formed at positions opposed to each other. Except the bulged portions 47a, 47b, the intermediate tube 47 is proximate to the distal-side tube 2. This construction prevents the pulling wire from moving on the outer surface of the distal-side tube 2 and allows the pulling wire to be pulled favorably.

As shown in FIGS. 20 and 22, the diameter of the intermediate tube 47 is decreased at its proximal side. The axially extended bulged portions 47a and 47b for accommodating the pulling wire, which are formed at positions opposed to each other are proximate to the pulling wires 6a and 6b respectively. Except the bulged portions 47a, 47b, the intermediate tube 47 is proximate to the distal-side tube 2. As shown in FIG. 20, the diameter-decreased proximal side of the intermediate tube 47 penetrates into the distal portion of a connection tube 48 and is fixed thereto. The proximal portion of the distal-side tube 2 and the distal portion of the proximal-side tube 4 are fixed to the proximal portion of the connection tube 48.

Similarly to the stent delivery device 1, the stent accommodation cylindrical member 5b is not bonded to the intermediate tube 47 and movable. Although the stent accommodation cylindrical member 5b is moved to the proximal side of the stent delivery device by pulling the pulling members 69a, 69b, the stent 3 is locked to the stent-locking portion 22. Thus the stent 3 is discharged from the stent accommodation cylindrical member 5b and self-expands. Even though the entire tube is made of a soft material, this mode allows the stent to be expanded safely without being bent in a blood vessel or the like, because the pulling wire is disposed inside the tube.

In the stent delivery device of the present invention, it is possible to prevent the movement of the stent toward the distal end thereof and easy to insert the stent delivery device to a desired portion of an organ, provided that the distal-side tube of the stent delivery device has a projected portion, for preventing the movement of the stent, which is provided at the side distal from the distal end of the stent and provided that the distal side of the above-described projected portion is gradually decreased in its diameter toward the distal end thereof.

In the stent delivery device of the present invention, it is possible to pull the pulling member favorably, provided that the stent delivery device has a member, for maintaining the position of the pulling member, which is disposed on the outer surface of the distal-side tube and has a passage through which the pulling member is capable of penetrating.

In the stent delivery device of the present invention, it is possible to move the stent accommodation cylindrical member to move favorably toward the proximal side of the stent delivery device, provided that a projected portion is provided on an outer surface of the distal-side tube and that the stent accommodation cylindrical member has a slit which extends from a proximal end thereof toward a distal side thereof and into which the projected portion is capable of moving.

In the stent delivery device of the present invention, it is possible to prevent the stent accommodation cylindrical member from moving excessively, provided that the stent delivery device has a portion for restricting a movement distance of the stent accommodation cylindrical member toward the proximal side of the stent delivery device.

EXAMPLE

The stent delivery device shown in FIGS. 1 through 7 was formed. The stent delivery device of this embodiment was formed on condition that a guide wire having a diameter of 0.035 inches. That is, the stent delivery device is of a so-called rapid exchange type. As the distal-side tube, a tube made of polyether ether ketone was used. The outer diameter and inner diameter of the distal-side tube were 1.23 mm and 0.95 mm respectively. As the stent-locking portion, a stainless steel ring was caulked to the outer surface of the distal-side tube. As the distal-end member, a polyester elastomer formed by injection molding was used. The stent was prepared by cutting a piece from a tube made of nickel titanium. As the stent accommodation cylindrical member, a polyimide tube was used. The outer diameter and inner diameter of the stent accommodation cylindrical member were 2.06 mm and 1.8 mm respectively. The outer diameter and inner diameter of the small-diameter portion were 1.60 mm and 1.36 mm respectively. As the intermediate tube, a tube made of polyimide tube was used. The outer diameter and inner diameter of the intermediate tube were 2.06 mm and 1.80 mm respectively. As the proximal-side tube, a tube made of polyether ether ketone was used. The outer diameter and inner diameter of the proximal-side tube were 1.16 mm and 0.85 mm respectively. As the pulling member, a stainless steel single wire was used. The outer diameter of the pulling member at its distal portion was 0.3 mm (length: 15 cm). The outer diameter at the proximal side thereof was 0.52 mm.

The stent delivery device of this embodiment was approached to a simulated blood vessel of an iliac arteria by using an introducer to expand the stent. The result was that the stent did not move.

A stent delivery device of another embodiment of the present invention is described below.

Figure 24:
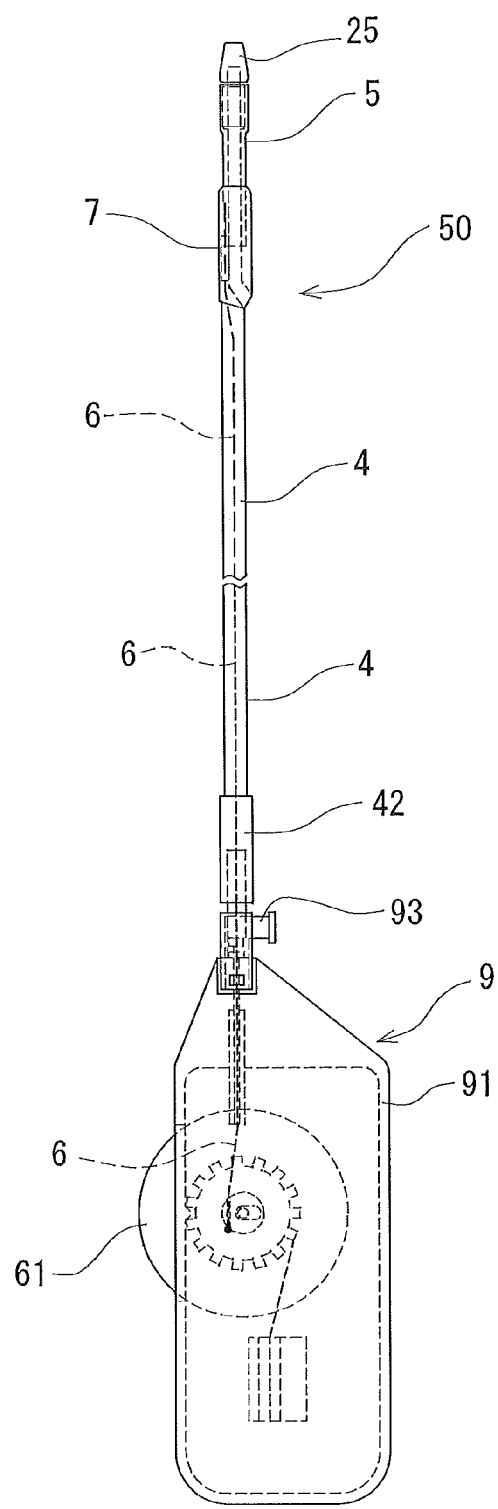
FIG. 24 is a partially schematic front view showing a stent delivery device of an embodiment of the present invention.
Figure 25:
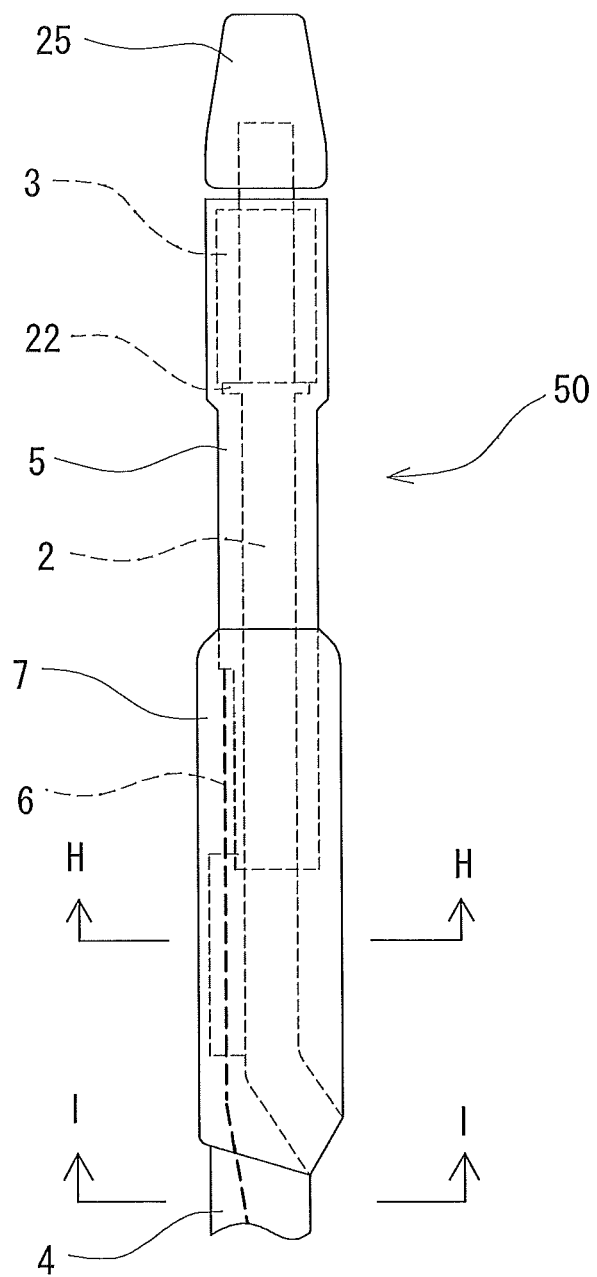
FIG. 25 is an enlarged outlook view showing the neighborhood of a distal portion of the stent delivery device shown in FIG. 24.
Figure 26:
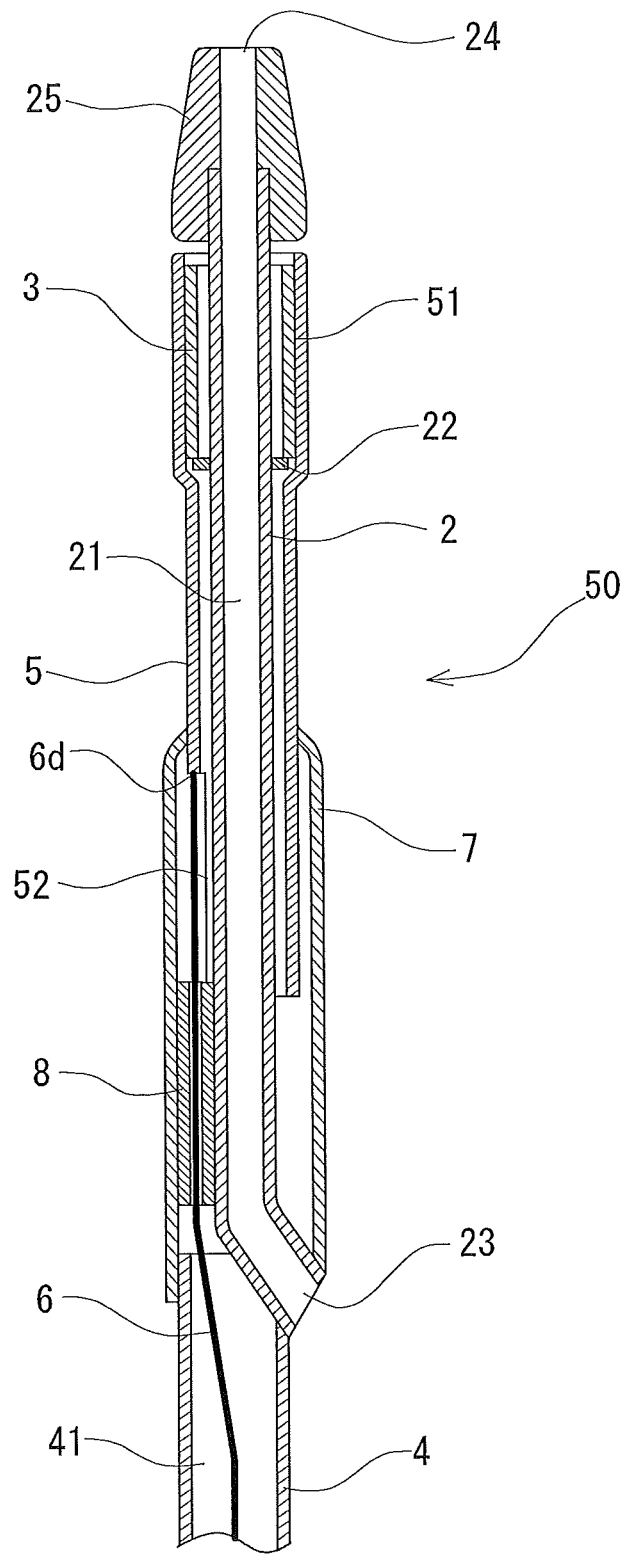
FIG. 26 is an enlarged sectional view showing the neighborhood of the distal portion of the stent delivery device shown in FIG. 24.
Figure 27:
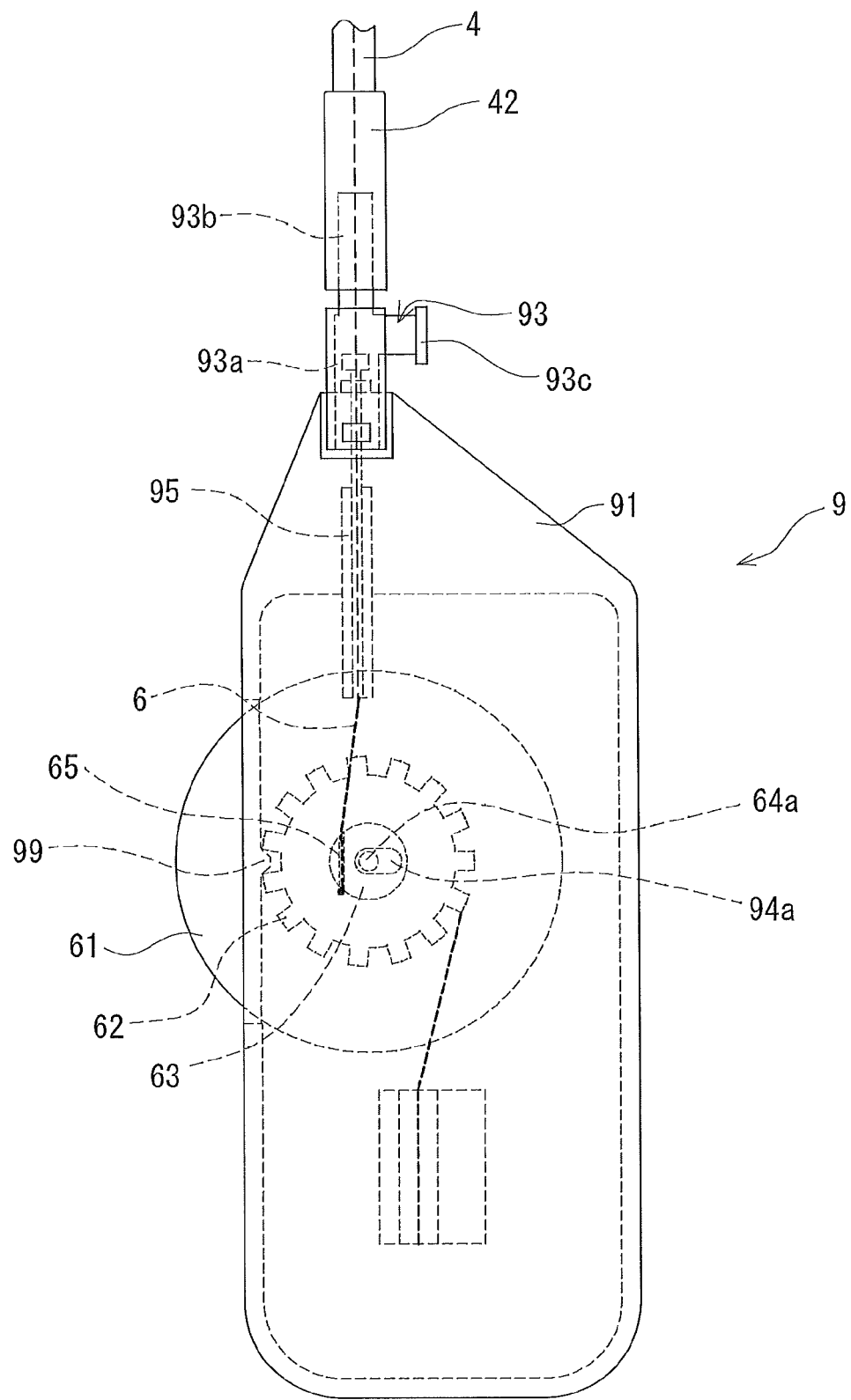
FIG. 27 is an enlarged outlook view showing the neighborhood of an operation portion of the stent delivery device shown in FIG. 24.
Figure 28:
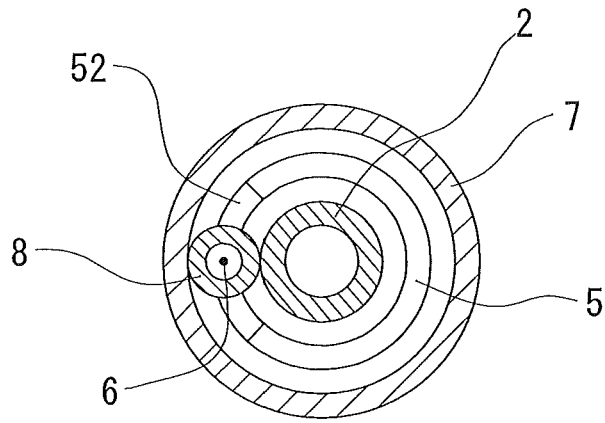
FIG. 28 is an enlarged sectional view taken along a line H-H of FIG. 25.
Figure 29:
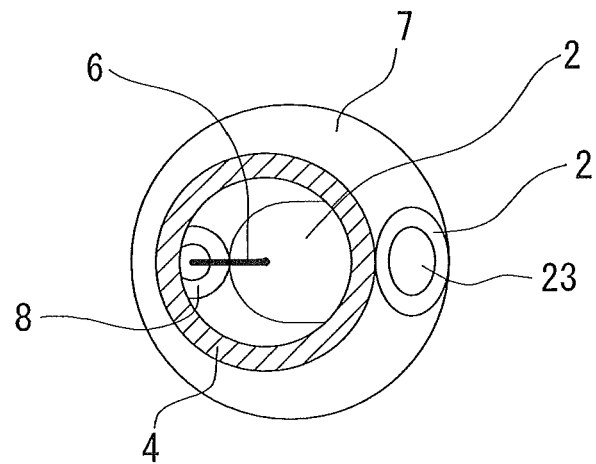
FIG. 29 is an enlarged sectional view taken along a line I-I of FIG. 25.

FIG. 24 is a partially schematic front view showing a stent delivery device of an embodiment of the present invention. FIG. 25 is an enlarged outlook view showing the neighborhood of a distal portion of the stent delivery device shown in FIG. 24. FIG. 26 is an enlarged sectional view showing the neighborhood of the distal portion of the stent delivery device shown in FIG. 24. FIG. 27 is an enlarged outlook view showing the neighborhood of an operation portion of the stent delivery device shown in FIG. 24. FIG. 28 is an enlarged sectional view taken along a line H-H of FIG. 25. FIG. 29 is an enlarged sectional view taken along a line I-I of FIG. 25.

Figure 5:
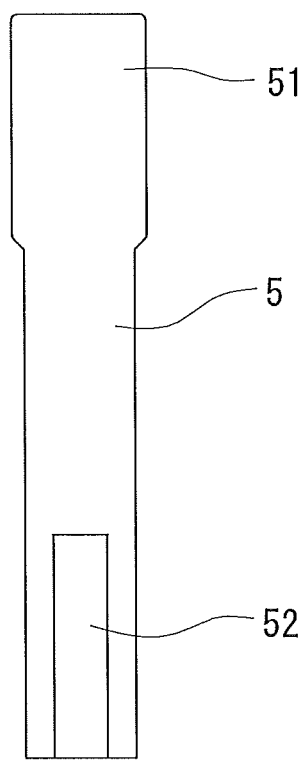
FIG. 5 is an outlook view showing an example of a stent accommodation cylindrical member for use in the stent delivery device of the present invention.
Figure 6:
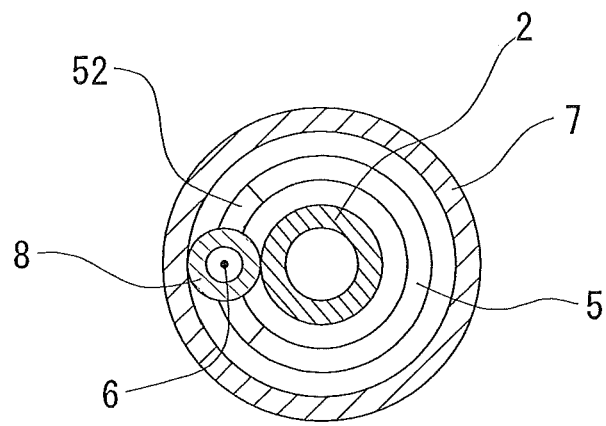
FIG. 6 is an enlarged sectional view taken along a line A-A of FIG. 2.

The outlook view showing the stent accommodation cylindrical member for use in the stent delivery device of this embodiment is similar to that shown in FIG. 5. Thus FIG. 5 is referred to.

A stent delivery device 50 of the present invention includes a distal-side tube 2 having a guide wire lumen 21; a proximal-side tube 4 whose distal portion is fixed to a proximal portion of the distal-side tube 2; a stent accommodation cylindrical member 5 which encloses a distal side of the distal-side tube 2 and is slidable toward a proximal end of the distal-side tube 2; a stent 3 accommodated in the stent accommodation cylindrical member 5; and a pulling member 6 which extends inside the proximal-side tube 4, with one end portion thereof fixed to the stent accommodation cylindrical member 5 and is pulled toward the proximal side of the proximal-side tube 4 to move the stent accommodation cylindrical member 5 toward a proximal side of the stent delivery device 1.

The distal-side tube 2 has a proximal-side opening 23 which is open at the proximal side of the distal-side tube 2 and communicates with the guide wire lumen 21; and a stent-locking portion 22 which is disposed at the distal side of the distal-side tube 2 and contacts a proximal end of the stent 3 accommodated inside the stent accommodation cylindrical member 5, thus preventing the stent 3 from moving to the proximal side of the stent delivery device. The stent 3 is formed approximately cylindrically and accommodated in the stent accommodation cylindrical member 5, with the stent 3 being compressed in an axial direction thereof. The stent 3 expands outward and returns to a configuration before the stent is compressed, when the stent is implanted in an organism.

At the proximal portion of the proximal-side tube 4, the stent delivery device 50 includes an operation portion 9 having a pulling wire winding mechanism for winding the pulling wire 6 and moving the stent accommodation cylindrical member 5 toward the proximal side of the stent delivery device.

According to the stent delivery device of the present invention using a self-expandable stent, the opening at the proximal side thereof is disposed not at the proximal end thereof, but at the proximal side of the distal-side tube. Therefore in a stent-implanting operation, it is easy to perform an operation of exchanging the stent delivery device with a stent delivery device of other type. By pulling the pulling wire to the proximal side of the stent delivery device, the stent can be discharged from the stent accommodation cylindrical member. Thus the position movement amount of the stent is very small in an operation of discharging the stent from the stent accommodation cylindrical member.

The operation portion 9 has a housing 91 (91a, 91b). It is preferable that the pulling wire winding mechanism has a rotational roller 61 for operational use (hereinafter referred to as merely rotational roller 61) having a portion exposed from the housing 91 and that by rotating the rotational roller 61, the pulling wire 6 is wound on the rotational roller 61 at its proximal side. This construction allows the operation portion 9 to be compact and an operation of rotating the rotational roller to be accomplished, with the housing 91 being held with a hand. Thus it is possible to perform an operation of discharging the stent from the stent delivery device with one hand.

It is preferable that in the stent delivery device 50, the outer diameter of the proximal-side tube 4 is set smaller than that of the portion, having the maximum diameter, which is disposed in the region of the stent delivery device 50 distal from the proximal-side tube 4. In this construction, even in a state in which the guide wire is extended along the side surface of the proximal-side tube from the opening at the proximal side of the stent delivery device to the proximal side of the stent delivery device, the outer diameter of the proximal-side tube is set almost equally to that of the portion, having the maximum diameter, which is disposed in the region of the stent delivery device distal from the proximal-side tube. Thereby the stent can be inserted into a narrow blood vessel.

The stent delivery device 50 of this embodiment has the distal-side tube 2, the proximal-side tube 4, the stent accommodation cylindrical member 5, the stent 3, the pulling wire 6, and an operation portion 9 having a mechanism for winding the pulling wire 6.

The stent delivery device 50 of this embodiment has the intermediate tube 7 that encloses the proximal side of the distal-side tube 2 and the proximal side of the stent accommodation cylindrical member 5 and is fixed at the proximal portion thereof to the proximal portion of the distal-side tube 2 and the distal portion of the proximal-side tube 4. In the stent delivery device 50 of this embodiment, the intermediate tube 7 encloses the proximal side of the distal-side tube 2 and the proximal side of the stent accommodation cylindrical member 5 without preventing the stent accommodation cylindrical member 5 from moving toward the proximal side of the stent delivery device 50. One end portion of the pulling wire 6 is fixed to the stent accommodation cylindrical member 5 inside the intermediate tube 7. The pulling wire 6 passes between the intermediate tube 7 and the distal-side tube 2 and extends into the proximal-side tube 4. This construction is preferable in that the pulling wire is not exposed.

The stent accommodation cylindrical member 5 is the same as that of the stent delivery device 1 of the above-described embodiment. As the stent 3, it is possible to use the self-expandable stent having any constructions. For example, it is possible to preferably use the stent 3 of the stent delivery device 1 of the above-described embodiment. As shown in FIGS. 25 through 29, the distal-side tube 2 is a tubular body having the guide wire lumen 21 penetrating through the distal-side tube 2 from its distal end to its proximal end. The distal-side tube 2 has a distal portion formed by a distal-end member 25 fixed to the distal end thereof and has a distal-end opening 24. The distal-side tube 2 is the same as that of the stent delivery device 1 of the above-described embodiment. The distal-end member 25 is also the same as that of the stent delivery device 1 of the above-described embodiment. As shown in FIGS. 25 and 26, the distal-side tube 2 has the stent-locking portion 22 for preventing the stent 3 from moving toward the proximal side of the stent delivery device 50. The stent-locking portion 22 is the same as that of the stent delivery device 1 of the above-described embodiment.

As shown in FIGS. 24 through 29, the proximal-side tube 4 is a tubular body extending from its distal end to its proximal end. The proximal-side tube 4 has a hub 12 fixed to its proximal end. The distal portion of the proximal-side tube is joined with the proximal portion of the distal-side tube 2. The proximal-side tube 4 has therein a lumen 41 through which the pulling wire 6 can be inserted.

The proximal-side tube 4 is the same as that of the stent delivery device 1 of the above-described embodiment. In the stent delivery device 50 of this embodiment, similarly to the stent delivery device 1 of the above-described embodiment, the outer diameter of the proximal-side tube 4 is set smaller than that of the portion, having a maximum diameter, which is disposed in the region of the stent delivery device 50 distal from the proximal-side tube 4. More specifically, in this embodiment, the outer diameter of the proximal-side tube 4 is set smaller than the maximum outer diameter of the portion where the distal-side tube 2 and the proximal-side tube 4 are fixed to each other.

Similarly to the stent delivery device 1 of the above-described embodiment, the stent delivery device 50 of this embodiment has the intermediate tube 7 which encloses the proximal side of the distal-side tube 2 and the proximal side of the stent accommodation cylindrical member 5 and is fixed at the proximal portion thereof to the proximal portion of the distal-side tube 2 and the distal portion of the proximal-side tube 4. In the stent delivery device 50 of this embodiment, the intermediate tube 7 encloses the proximal side of the distal-side tube 2 and the proximal side of the stent accommodation cylindrical member 5 without preventing the stent accommodation cylindrical member 5 from moving toward the proximal side of the stent delivery device 50. One end portion of the pulling wire 6 is fixed to the stent accommodation cylindrical member 5 inside the intermediate tube 7. The pulling wire 6 passes between the intermediate tube 7 and the distal-side tube 2 and extends into the proximal-side tube 4.

The proximal portion of the distal-side tube 2 extends inside the intermediate tube 7 and is exposed from the proximal end of the intermediate tube 7. The distal portion of the proximal-side tube 4 penetrates into the proximal portion of the intermediate tube 7. The distal-side tube 2, the proximal-side tube 4, and the intermediate tube 7 are liquid-tightly fixed to the proximal portion of the intermediate tube 7. The lumen 41 inside the proximal-side tube 4 communicates with the inside of the intermediate tube 7. As shown in FIGS. 25 and 26, the distal portion of the intermediate tube 7 is decreased in its diameter or curved. It is preferable that the distal end of the intermediate tube 7 liquid-tightly contacts the outer surface of the stent accommodation cylindrical member 5 without preventing the movement of the stent accommodation cylindrical member 5. But the distal end of the intermediate tube 7 does not necessarily have to contact the outer surface of the stent accommodation cylindrical member 5. The intermediate tube is the same as that of the stent delivery device 1 of the above-described embodiment.

The stent delivery device 50 has the pulling wire 6 extending inside the proximal-side tube 4, with one end portion thereof fixed to the stent accommodation cylindrical member 5. The pulling wire 6 is pulled toward the proximal side of the proximal-side tube 4 to move the stent accommodation cylindrical member 5 to the proximal side of the stent delivery device.

In the stent delivery device 50 of this embodiment, the pulling member 6 is constructed of a pulling wire. As shown in FIGS. 24, 25, and 27, the pulling wire 6 penetrates through the proximal-side tube 4 and extends to the outside from the proximal end of the proximal-side tube 4. The pulling wire 6 is the same as that of the stent delivery device 1 of the above-described embodiment.

The stent delivery device 50 of this embodiment has the projected portion (tubular member) 8 provided on the outer surface of the distal-side tube 2 at its proximal side. The projected portion 8 (tubular member) is capable of moving inside the slit 52 of the stent accommodation cylindrical member 5. The projected portion 8 (tubular member) is the same as that of the stent delivery device 1 of the above-described embodiment.

The stent delivery device 50 of this embodiment has a member for holding the position of the pulling wire. This member is disposed on the outer surface of the distal-side tube 2 and has a passage through which the pulling wire 6 is capable of penetrating. The stent delivery device of this embodiment has a tubular member 8 displaying the function of the member for holding the position of the pulling wire and the function of the above-described projected portion. The pulling wire 6 can be pulled favorably by the member for holding the position of the pulling wire. It is preferable that the member for holding the position of the pulling wire is disposed on an extension of a fixing portion 6d, at the proximal side thereof, where the pulling wire 6 and the stent accommodation cylindrical member 5 are fixed to each other. As the member for holding the position of the pulling wire, it is possible to use members having the passage through which the pulling wire 6 is capable of penetrating. For example, it is possible to use a ring-shaped member, a ring-shaped member having a cut-out, and a trough-shaped member. It is preferable to use a plurality of the ring-shaped members.

As the tubular member 8, a tube having a lumen whose outer diameter is larger than that of the pulling member therein is used. The length of the tubular member 8 is favorably in the range of 10 to 180 mm and more favorably in the range of 15 to 120 mm. The outer diameter of the tubular member is favorably in the range of 0.15 to 0.8 mm and more favorably in the range of 0.2 to 0.5 mm. It is favorable that the inner diameter of the tubular member is larger than the outer diameter of the pulling member by 0.05 to 0.2 mm.

It is preferable that the member for holding the position of the pulling member is fixed to the outer surface of the distal-side tube 2. But the member for holding the position of the pulling member may be fixed to the inner surface of the distal-side tube 2. Further the member for holding the position of the pulling member may be extended to the side distal from the distal end of the proximal-side tube 4. Furthermore resin having low frictional property which increases lubricity may be applied to the inner surface of the member for holding the position of the pulling member.

As shown in FIGS. 24, 27, 30 through 32, the stent delivery device 50 of the present invention has the operation portion 9 fixed to at the proximal end of the proximal-side tube 4, namely, to a hub 42 provided at the proximal end of the proximal-side tube 4.

The operation portion 9 of the stent delivery device 50 has a pulling wire winding mechanism, a locking mechanism for releasably locking a rotation of the pulling wire winding mechanism, and a reverse rotation prevention mechanism for preventing the rotation of the pulling wire winding mechanism in a direction opposite to a pulling wire winding direction.

The operation portion 9 has a housing 91 composed of a body 91a and a covering member 91b sealing an open portion of the body 91a. A connector 93 which is connected with a hub 42 is fixed to the distal portion of the housing 91. The housing 91 has a pulling wire passage 97 extended from the distal end of the distal portion thereof to the inside thereof. The connector 93 is fixed to the distal portion of the housing 91 by means of a fixing member 96 in such a way that a passage inside the connector 93 communicates with the pulling wire passage 97.

Figure 30:
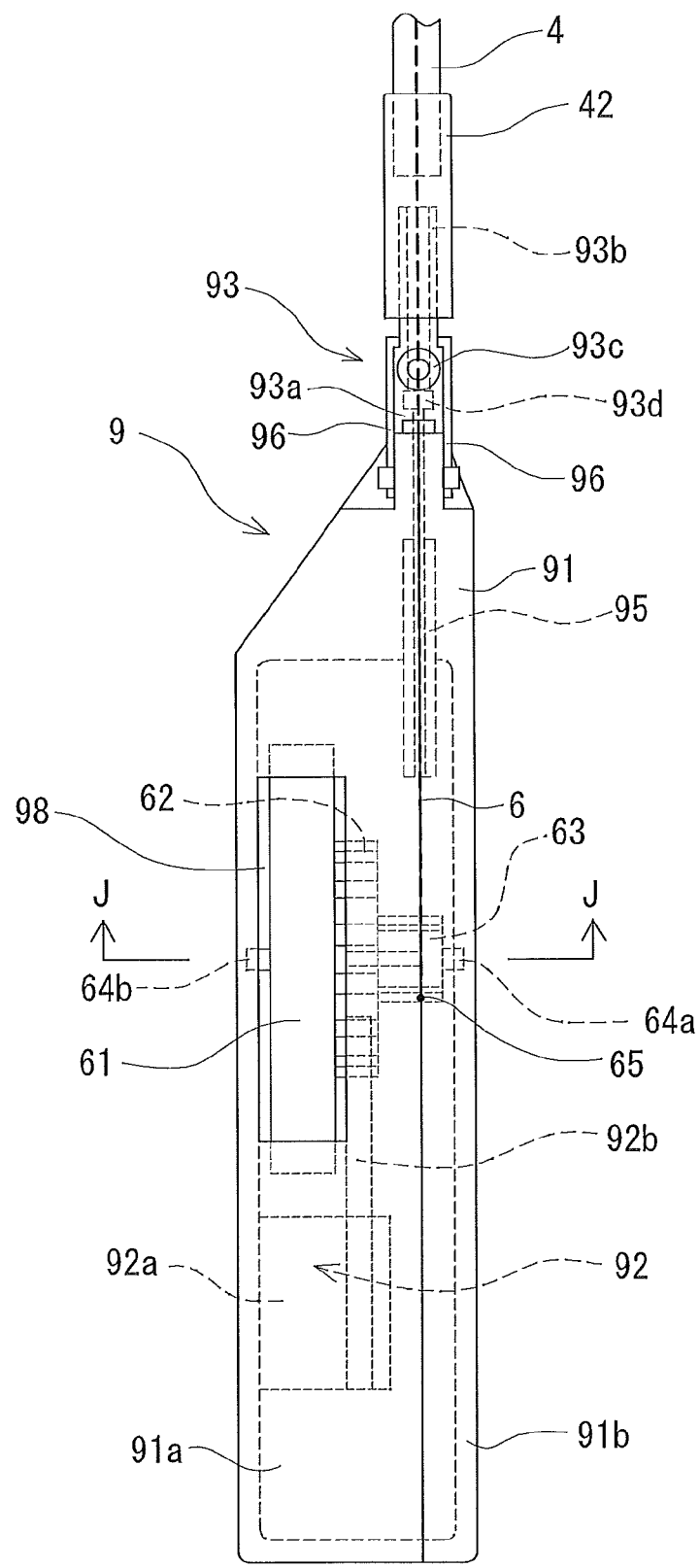
FIG. 30 is a right-hand side view showing the neighborhood of the operation portion of the stent delivery device shown in FIG. 24.
Figure 33:
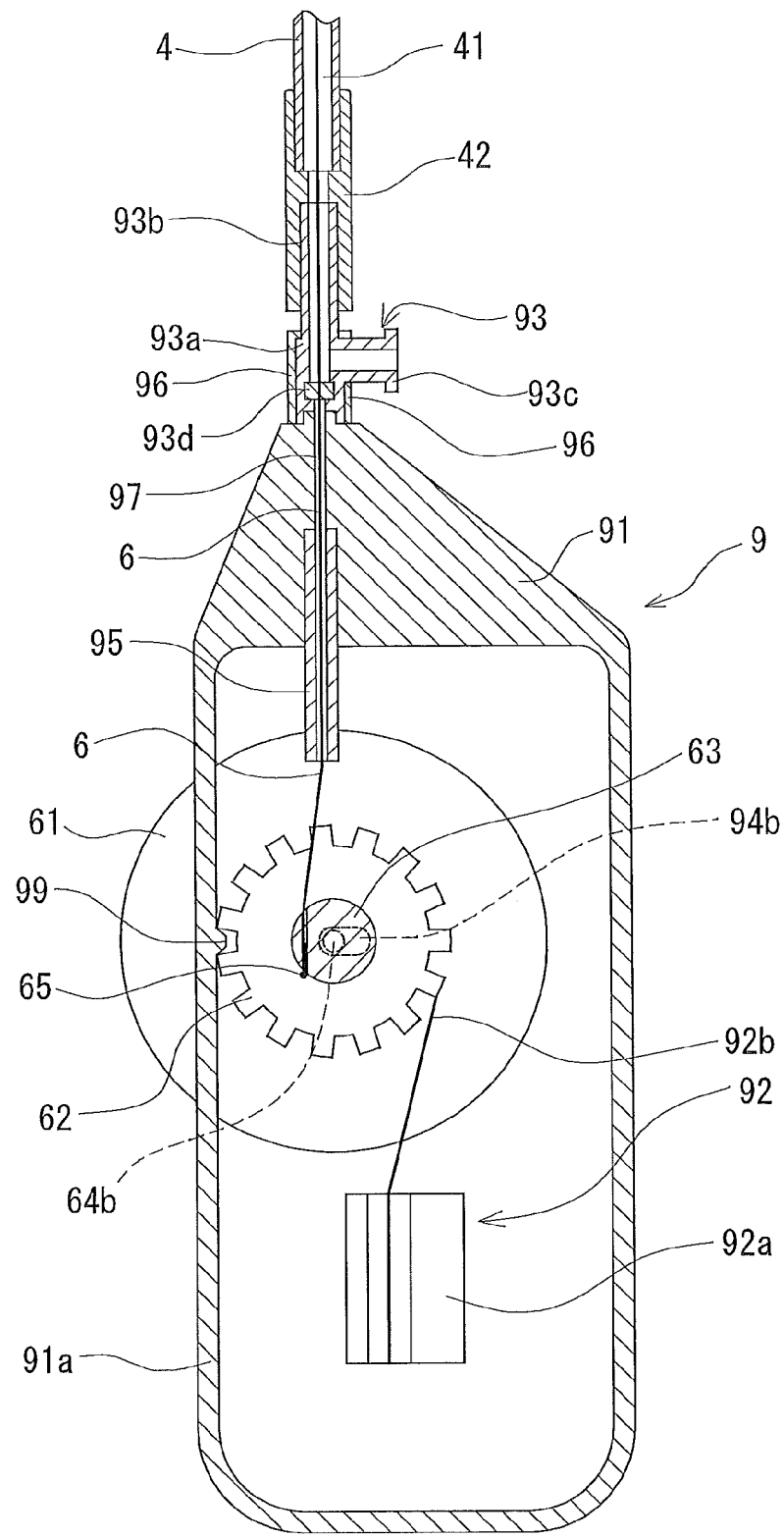
FIG. 33 is an enlarged sectional view taken along a line K-K of FIG. 32.

As shown in FIGS. 27, 30, and 33, the connector 93 includes a hollow body 93a, a connection port 93b extended from the body 93a, a side port 93c, and a sealing member 93d holding the pulling wire 6 slidably and liquid-tightly. The connection port 93b is mounted at the proximal portion of the hub 42 of the proximal-side tube 4.

As materials for forming the housing of the operation portion, the connector 93, and the hub 42, it is possible to use the following rigid or semi-rigid materials: synthetic resin including polycarbonate, polyolefins (for example, polyethylene, polypropylene, ethylene-propylene copolymer), styrene resin, for example, polystyrene, MS resin such as methacrylate-styrene copolymer, MBS resin such as methacrylate-butylene-styrene copolymer, polyester; and metal such as stainless steel, aluminum, and aluminum alloy.

The housing 91 is so provided as to enclose a pulling wire passage 97. The housing 91 projects from the proximal ends of the pulling wire passage 97 and has a wire protection tube 95 extending inside the housing. The wire protection tube 95 is made of a flexible material or an elastic material.

As the material for forming the sealing member 93 and the wire protection tube 95, the following elastic materials are used: rubbers including synthetic rubber such as urethane rubber, silicone rubber, butadiene rubber, and natural rubber such as Latex rubber; synthetic resin elastomers such as olefin elastomers (for example polyethylene elastomer, polypropylene elastomer), polyamide elastomer, styrene elastomers, (for example, styrene-butadiene-styrene copolymer, styrene-isoprene-styrene copolymer, styrene-ethylenebutylene-styrene copolymer), polyurethane, urethane elastomers, fluororesin elastomers.

Figure 31:
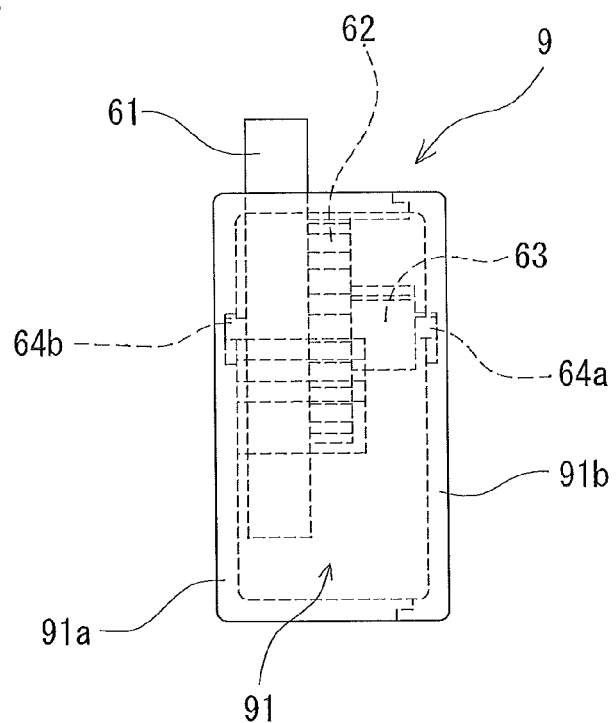
FIG. 31 is a bottom view showing the operation portion of the stent delivery device shown in FIG. 24.
Figure 32:
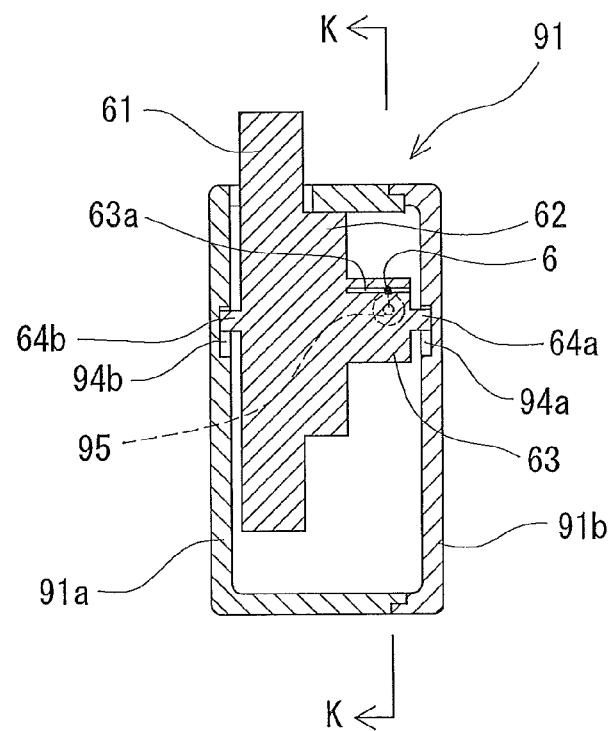
FIG. 32 is an enlarged sectional view taken along a line J-J of FIG. 30.

As shown in FIG. 30, the body 91a of the housing includes an open portion 98 for partly projecting the rotational roller 61, a locking rib 99 engaging a projected portion of a gear portion 62 (see FIG. 33) provided on the roller 61, and a bearing portion 94b accommodating one end 64b of the rotating shaft of the roller 61. The covering member 91b has a bearing portion 94a accommodating the other end 64a of the rotating shaft of the roller 61. The locking rib 99 is so configured that it is capable of penetrating into the gap between adjacent projected portions formed on the gear portion 62 of the roller 61. As shown in FIGS. 31 and 32, the bearing portions 94a and 94b accommodate the other end 64a and the one end 64b of the rotating shaft of the roller 61 respectively and are oblongly extended in a direction in which they recede from the above-described locking rib 99. The bearing portions 94a and 94b are not limited to an oblong configuration, but may have configurations which allow them to move a distance in which they disengage from the locking rib. For example, the bearing portions 94a and 94b may be rectangular, elliptic, and gourd-shaped like an operation portion 100 of the embodiment that will be described later. As shown in FIGS. 31 and 32, the bearing portions 94a and 94b of this embodiment are formed in parallel with the rotational shaft of the roller 61 and extend downward (vertical direction of open portion 98). The bearing portions 94a and 94b have a length allowing the roller 61 to move a distance longer than the height of the locking rib 99.

Figure 35:
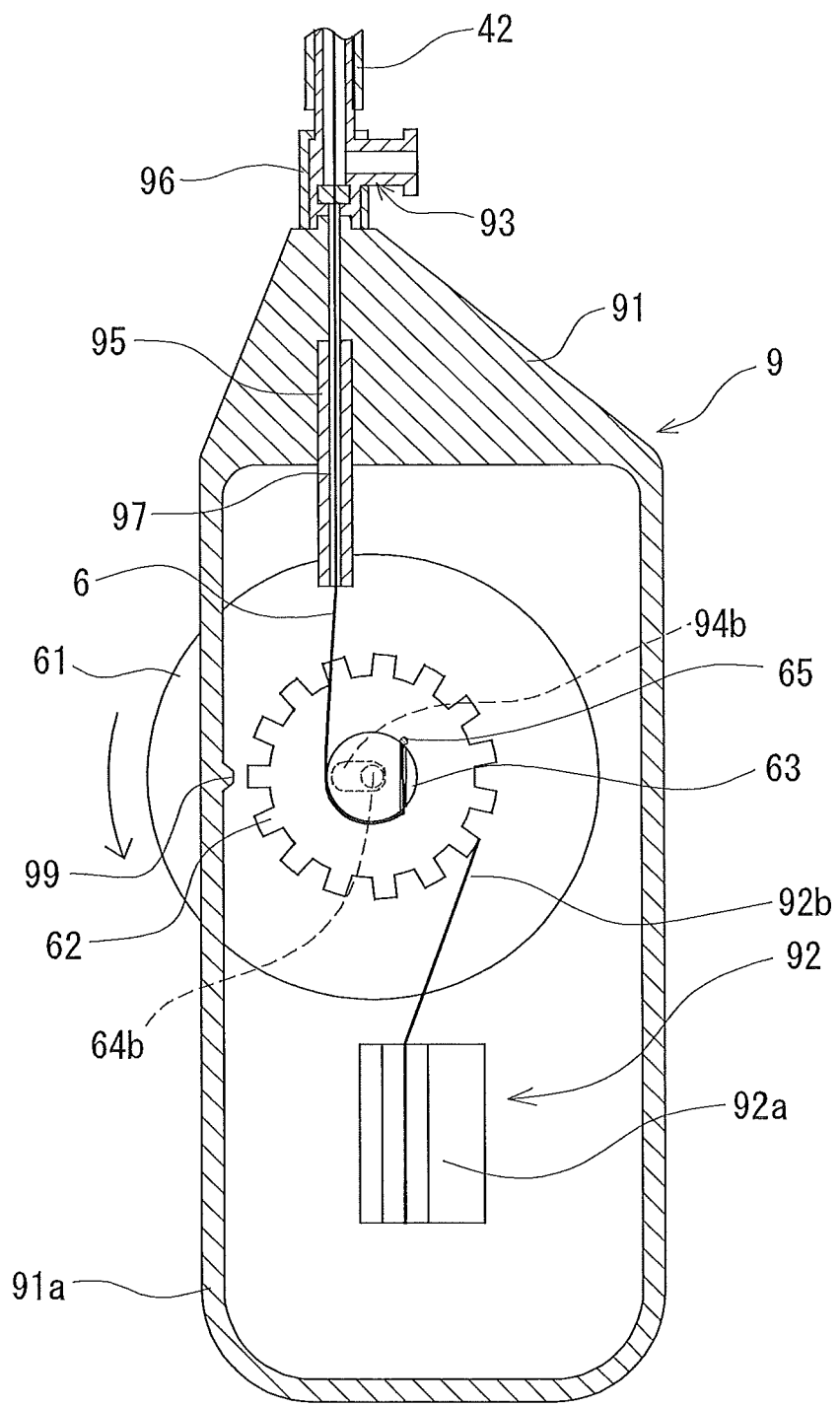
FIG. 35 is an explanatory view for explaining the operation of the stent delivery device of the present invention.
Figure 36:
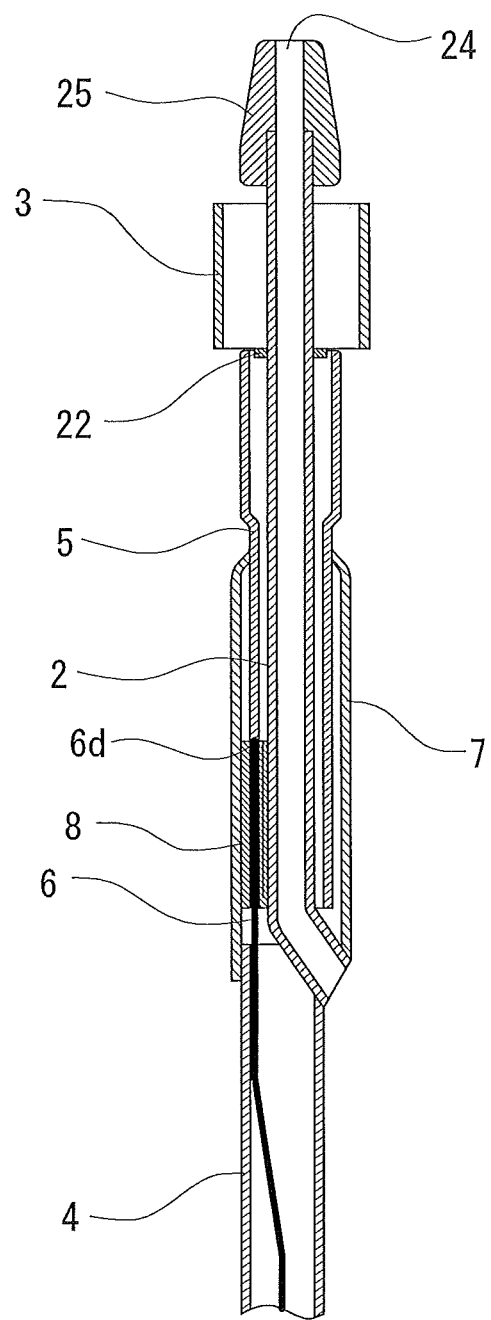
FIG. 36 is an explanatory view for explaining the operation of the stent delivery device of the present invention.

The pulling wire winding mechanism is constructed of the roller 61 and a winding shaft portion 63 which is rotated by the rotation of the roller 61. The proximal portion of the pulling wire 6 is held by the winding shaft portion 63 or secured thereto. More specifically, as shown in FIG. 32, an anchoring portion 65 larger than the wire 6 is provided at the proximal portion of the pulling wire 6. A slit 63a capable of accommodating the pulling wire 6 is formed in the winding shaft portion 63. The slit 63a of the winding shaft portion 63 accommodates the proximal portion of the pulling wire 6, with the anchoring portion 65 disposed outward from the proximal end of the slit 63a. Thereby when the winding shaft portion 63 having the above-described construction rotates, the wire 6 is wound on the outer surface thereof, as shown in FIG. 35. The method of holding the pulling wire 6 on the winding shaft portion 63 or securing the pulling wire 6 thereto is not limited to the above-described method, but any methods can be used. For example, the proximal end of the pulling wire 6 or the proximal portion thereof may be directly secured to the winding shaft.

It is preferable that the proximal portion of the pulling wire 6 to be wound on the winding shaft portion 63 is soft to allow the pulling wire 6 to be wound easily. To make the proximal portion of the pulling wire 6 flexible, it is possible to adopt a method of forming the proximal portion of the pulling wire 6 of a flexible material and a method of decreasing the diameter of the proximal portion of the pulling wire 6.

In this embodiment, the winding shaft portion 63 is formed integrally with the rotational roller 61 to make the winding shaft portion 63 and the rotational roller 61 coaxial with each other. Thus by rotating the rotational roller 61, the winding shaft portion 63 rotates simultaneously therewith. It is preferable that the winding amount of the pulling wire is smaller than the amount of an operation required to rotate the rotational roller. By doing so, the pulling wire can be wound slowly and the stent accommodation cylindrical member 5 is allowed to move toward the proximal side of the stent delivery device slowly and favorably. In this embodiment, because the outer diameter of the winding shaft portion is set smaller than that of the rotational roller, the winding amount of the pulling wire is allowed to be smaller than the amount of the operation required rotating the rotational roller.

The outer diameter of the winding shaft portion 63 is favorably in the range of 1 to 60 mm and more favorably in the range of 3 to 30 mm. The outer diameter of the rotational roller is favorably 1 to 20 times and more favorably 1 to 10 times larger than that of the p winding shaft portion. More specifically, the outer diameter of the rotational roller is favorably in the range of 10 to 60 mm and more favorably in the range of 15 to 50 mm.

The rotational roller and the winding shaft portion do not necessarily have to be formed integrally, but the winding shaft portion may be constructed of a separate member which follows the rotation of the rotational roller. As the transmission system of the rotational roller, it is possible to use a gear type, a belt type, and the like. It is preferable that surfaces of parts which have a possibility of contact with the surface of the rotational roller 61 in operating the rotational roller 61 is not slippery. For example, it is preferable to treat surfaces of parts which have a possibility of contact with the surface of the rotational roller 61 in operating the rotational roller 61 by knurling treatment, emboss treatment, application of a high-frictional material, and the like.

The operation portion 9 of this embodiment has the locking mechanism for releasably locking the rotation of the pulling wire winding mechanism and the reverse rotation prevention mechanism for preventing the rotation of the pulling wire winding mechanism in the direction opposite to the pulling wire winding direction.

Figure 34:
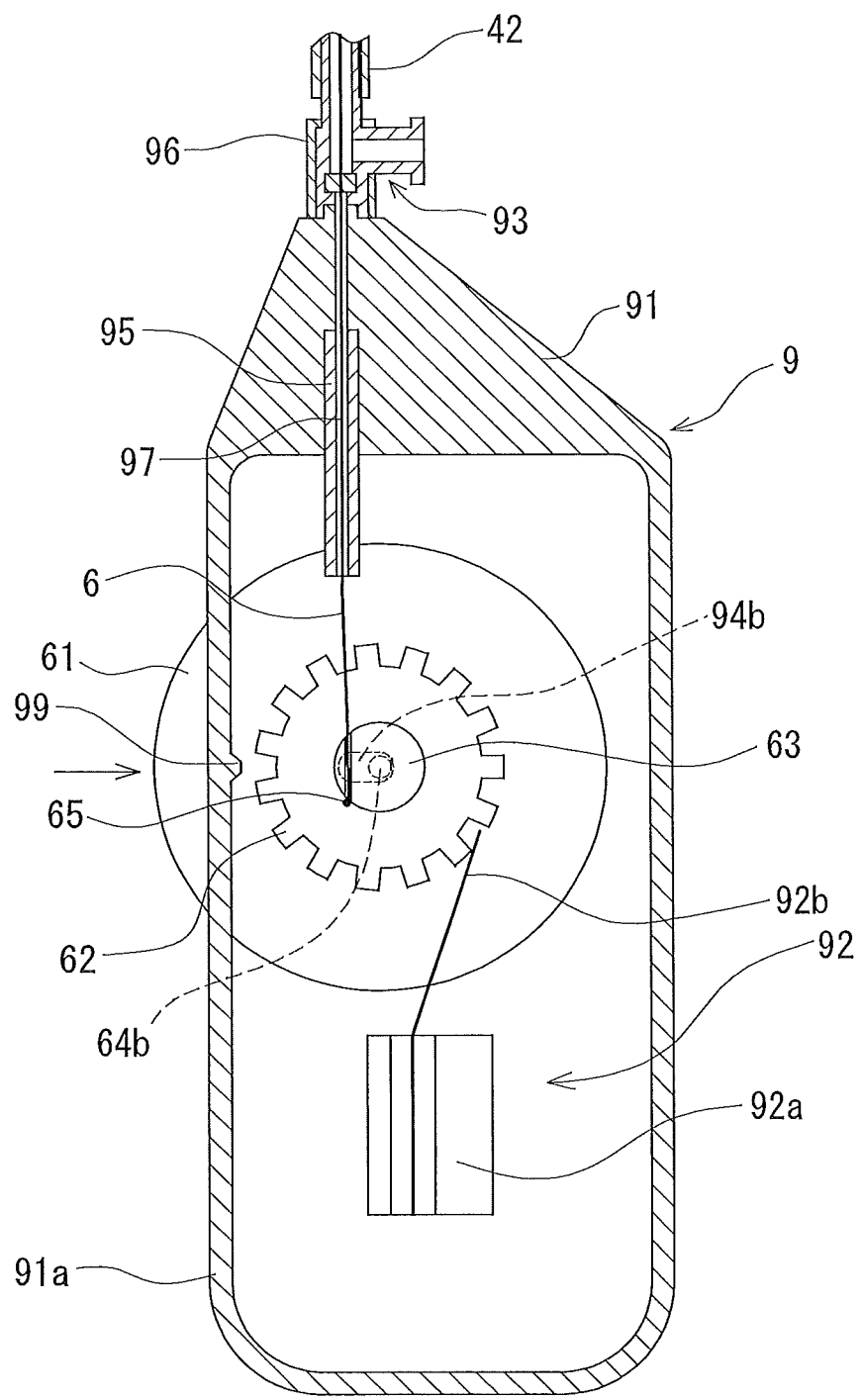
FIG. 34 is an explanatory view for explaining the operation of the stent delivery device of the present invention.

As shown in FIGS. 27, 30 through 33, the rotational roller 61 has the gear portion 62 which is coaxial therewith and rotates together therewith. The rotational roller 61 has a portion partly exposed from the open portion 98. The exposed portion serves as the operation portion. The roller 61 has other end 64a provided on one side surface of the rotating shaft thereof and one end 64b provided on the other side surface (side surface of winding shaft) thereof. An urging means 92 for urging the rotational roller 61 toward the open portion 98 of the housing 91 is provided inside the housing 91. More specifically, an urging member 92b of the urging means 92 urges the roller 61. The body 91a of the housing accommodates the locking rib 99 capable of penetrating into the gap between adjacent projected portions formed on the gear portion 62 of the roller 61. Therefore the rotating roller 61 has a state shown in FIG. 33, when the rotating roller 61 is urged by the urging member 92b. Thus the locking rib 99 engages the projected portion of the gear portion 62, which prevents the rotating roller 61 from rotating. When the rotating roller 61 is pressed in the direction in which it moves away from the locking rib 99, namely, in a direction shown with the arrow of FIG. 34, the one end 64b and other end 64a of the rotating shaft of the roller 61 move inside the bearing portions 94b and 94a respectively provided in the housing 91. Thereby the rotational roller 61 has a state shown in FIG. 34. In this state, the locking rib 99 is in disengagement from the projected portions of the gear portion 62 and thus rotatable. Thus the operation portion 9 of this embodiment prevents the rotation of the rotational roller 61 when it is not pressed and has the locking mechanism for releasably locking the rotation of the pulling wire winding mechanism.

The operation portion of this embodiment has the reverse rotation prevention mechanism composed of the urging means 92 having the urging member 92b and the above-described gear portion 62. The reverse rotation prevention mechanism prevents the rotation of the pulling wire winding mechanism in the direction opposite to the pulling wire winding direction. The urging means 92 has the urging member 92b and the fixing member 92a for fixing the urging member 92b to the housing 91. As the urging member 92b, a leaf spring is used. The leaf spring extends from the fixing member 92a to a lower portion of the gear portion 62 through the rear (direction opposite to distal portion of operation portion) of the gear portion 62 in such a way that the distal end of the leaf spring engages the projected portions disposed at the lower portion of the gear portion 62. Because the leaf spring is pressed against the gear portion 62, with the leaf spring in contact therewith, as described above, the roller 62 is urged toward the open portion 98 of the housing. The roller 61 is pressed as described above and has a state shown in FIG. 33 in which the roller 61 is rotatable. As shown in FIG. 35, the roller 61 is rotatable in the direction (pulling wire-winding direction) shown with the arrow of FIG. 35. If an operation of rotating the roller 61 in the opposite direction is performed, the projected portion of the gear portion 62 and the distal end of the urging member 92b engage each other. Thereby the rotation of the roller 61 is prevented. Thereby the reverse rotation prevention mechanism prevents the rotation of the pulling wire winding mechanism in the direction opposite to the pulling wire winding direction. As the material for the leaf spring serving as the urging member, any materials capable of displaying elasticity can be used. For example, it is possible to use metal (steel for spring) and synthetic resin.

The outer diameter of the gear portion 62 is favorably in the range of 10 to 60 mm and more favorably in the range of 15 to 50 mm. The number of cogs thereof is favorably in the range of 4 to 200 mm and more favorably in the range of 4 to 70.

Figure 41:
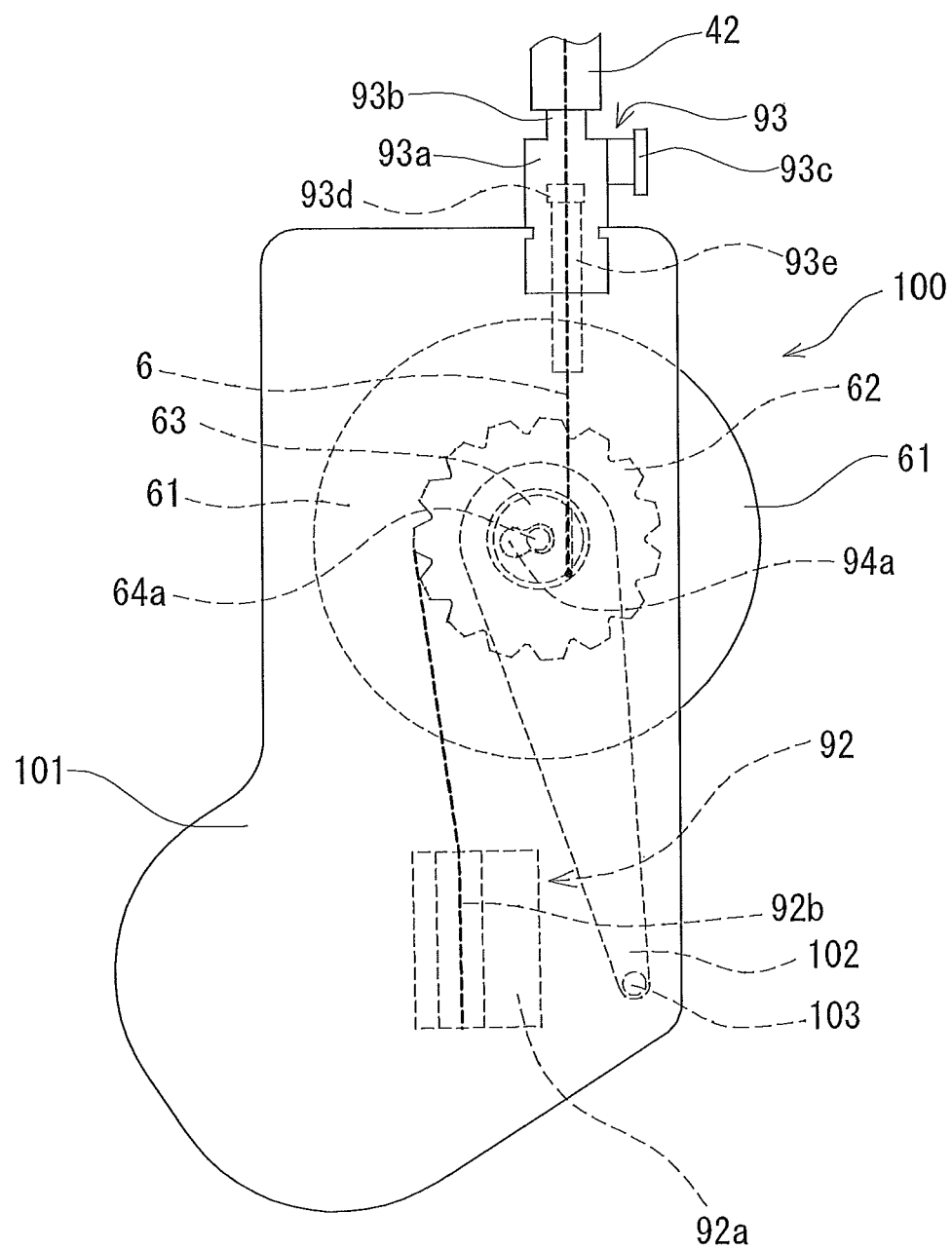
FIG. 41 is an enlarged outlook view showing the neighborhood of an operation portion of a stent delivery device of another embodiment of the present invention.
Figure 42:
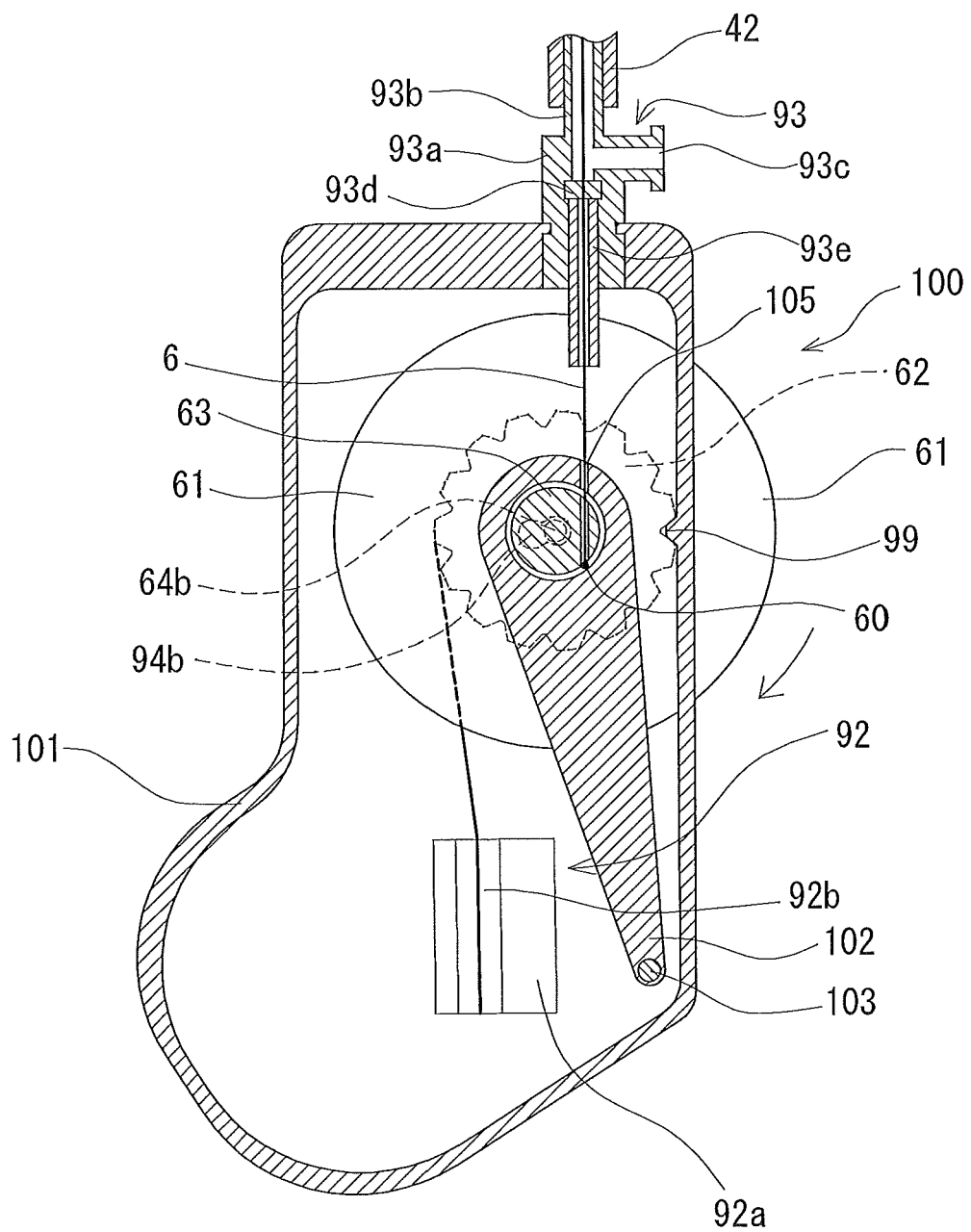
FIG. 42 is an enlarged sectional view showing the neighborhood of the operation portion of the stent delivery device shown in FIG. 41.
Figure 43:
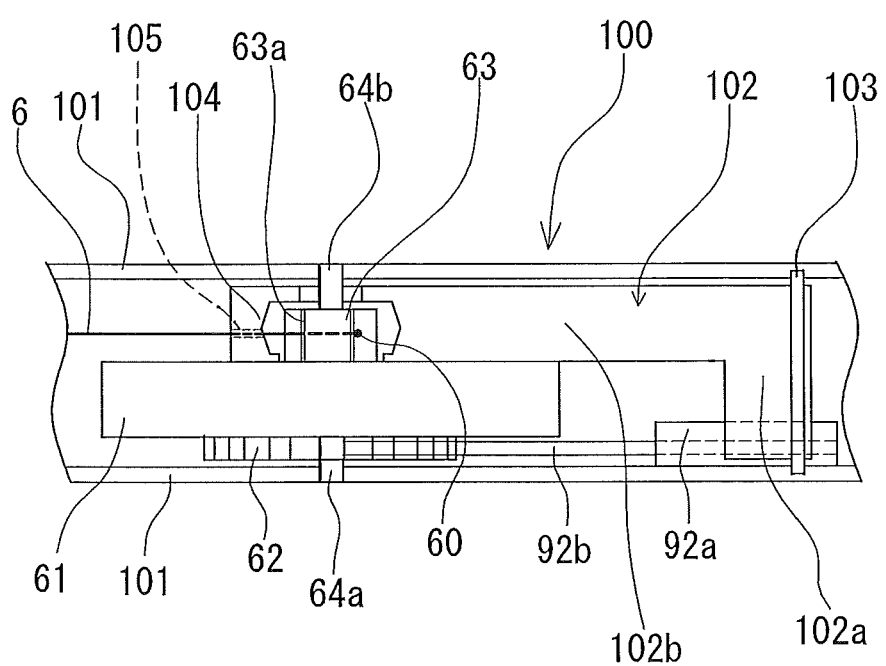
FIG. 43 is an explanatory view for explaining an internal construction of the neighborhood of an operation portion of the stent delivery device shown in FIG. 41.

The operation portion may have a construction as shown in FIGS. 41 through 43.

FIG. 41 is an enlarged outlook view showing the neighborhood of an operation portion of a stent delivery device of another embodiment of the present invention. FIG. 42 is an enlarged sectional view showing the neighborhood of the operation portion of the stent delivery device shown in FIG. 41. FIG. 43 is an explanatory view for explaining an internal construction of the neighborhood of an operation portion of the stent delivery device shown in FIG. 41.

The basic construction of an operation portion 100 of the stent delivery device of this embodiment is the same as that of the above-described operation portion 9. The operation portion 100 is different from the operation portion 9 in the configuration of the housing 101, and the position of the winding shaft portion 63 and that of the gear portion 62 for the rotational roller 61. In addition, the operation portion 100 has a collar member 102 and a connector 93 has a wire protection tube 93e.

As shown in FIGS. 41 and 42, the operation portion 100 has a housing 101. The proximal side of the housing 101 is bent and rounded. This configuration allows the housing 101 to be held easily and the roller to be operated easily. The housing 101 has a connector-mounting portion at its distal portion. The connector-mounting portion is formed as a concave portion on which the proximal portion of the connector 93 can be mounted.

As shown in FIG. 42, the connector 93 includes a hollow body 93a, a connection port 93b extended from the body 93a, a side port 93c extended therefrom, a sealing member 93d holding the pulling wire 6 slidably and liquid-tightly, and the wire protection tube 93e. The wire protection tube 93e extends from the body 93a and is projected into the housing 101.

As the material for forming the housing 101 of the operation portion and the connector 93, the following elastic materials are used: rubbers including synthetic rubber such as urethane rubber, silicone rubber, butadiene rubber, and natural rubber such as Latex rubber; synthetic resin elastomers such as olefin elastomers (for example polyethylene elastomer, polypropylene elastomer), polyamide elastomer, styrene elastomers, (for example, styrene-butadiene-styrene copolymer, styrene-isoprene-styrene copolymer, styrene-ethylenebutylene-styrene copolymer), polyurethane, urethane elastomers, fluororesin elastomers.

As shown in FIGS. 41 and 42, the housing 101 includes an open portion for partly projecting the rotational roller 61, a locking rib 99 engaging projected portions of a gear portion 62 (see FIG. 42) provided on the roller 61, a bearing portion 94b accommodating one end 64b of the rotating shaft of the roller 61, and a bearing portion 94a accommodating the other end 64a of the rotating shaft of the roller 61. The locking rib 99 is so configured that it is capable of penetrating into the gap between adjacent projected portions formed on the gear portion 62 of the roller 61. As shown in FIGS. 41 and 42, the bearing portions 94a and 94b accommodate the one end 64b and the other end 64a of the rotating shaft of the roller 61 respectively and have the shape of a gourd extended in a direction in which they recede from the above-described locking rib 99. The bearing portions 94a and 94b are not limited to the shape of the gourd, but may have configurations which allow them to move a distance in which they are capable of disengaging from the locking rib. For example, the bearing portions 94a and 94b may be rectangular, elliptic, and gourd-shaped. In the operation portion 100 of the embodiment, the bearing portions 94a and 94b are gourdlike, as shown in FIGS. 41 and 42. Therefore the rotational roller 61 is pressed to allow the ends 64b, 64a of the rotating shaft of the roller 61 accommodated in a space formed at one side of the bearing portions 94a, 94b to ride across opposed rib portions formed on the inner side surface of the central portion of the bearing portions 94a, 94b. Thereby the ends 64b, 64a of the rotating shaft of the roller 61 are accommodated in a space formed at the other side of the bearing portions 94a, 94b. In this state, the roller 61 is pressed by the urging member. Thereby the ends 64b, 64a of the rotating shaft of the roller 61 contact opposed ribs formed on the inner side surface of the central portion of the bearing portions 94a, 94b and thus do not move to the space formed at the one side of the bearing portions 94a, 94b. Therefore the roller 61 keeps a rotatable state.

In this embodiment, the operation portion 100 has the collar member 102. The collar member 102 accommodates the winding shaft portion 63 and has a collar portion 104 forming an annular space between it and the winding shaft portion 63. The collar portion 104 prevents the pulling wire wound around the winding shaft portion 63 from becoming loose. The collar member 102 has a function of guiding the rotational roller in its movement and suppressing shaking of the rotational roller, when the rotational roller is pressed. The shaft of the collar member 102 is supported with a pin 103. Thus as shown in FIGS. 41 and 42, the bearing portions 94a, 94b are formed in the shape of a gentle circular arc about the pin 103. The bearing portions 94a and 94b have the length allowing the roller 61 to move a distance longer than the height of the locking rib 99. As shown in FIG. 43, the collar member 102 has a passage 105 which reaches the space inside the collar portion 104 from the side surface thereof. The pulling wire 6 penetrates through the passage 105 and is fixed to the winding shaft portion 63.

The pulling wire winding mechanism is constructed of the roller 61 and the winding shaft portion 63 which is rotated by the rotation of the roller 61. The proximal portion of the pulling wire 6 is held by the winding shaft portion 63 or secured thereto. More specifically, as shown in FIG. 42, an anchoring portion 65 larger than the wire 6 is provided at the proximal portion of the pulling wire 6. A slit 63a capable of accommodating the pulling wire 6 is formed in the winding shaft portion 63. The slit 63a of the winding shaft portion 63 accommodates the proximal portion of the pulling wire 6, with the anchoring portion 65 disposed outward from the slit 63a. Thereby when the winding shaft portion 63 having the above-described construction rotates, the wire 6 is wound on the outer surface thereof. The method of holding the proximal portion of the pulling wire 6 on the winding shaft portion 63 or securing the pulling wire 6 thereto is not limited to the above-described method, but any methods can be used. For example, the proximal end of the pulling wire 6 or the proximal portion thereof may be directly secured to the winding shaft.

It is preferable that the proximal portion of the pulling wire 6 to be wound on the winding shaft portion 63 is soft to allow the pulling wire 6 to be wound easily. To make the proximal portion of the pulling wire 6 flexible, it is possible to adopt a method of making the proximal portion of the pulling wire 6 of a flexible material and a method of decreasing the diameter of the proximal portion of the pulling wire 6.

In this embodiment, the winding shaft portion 63 is formed integrally with the rotational roller 61 to make the winding shaft portion 63 and the rotational roller 61 coaxial with each other. As shown in FIG. 43, the winding shaft portion 63 is provided on one side surface of the rotational roller 61. Thus by rotating the rotational roller 61, the winding shaft portion 63 rotates simultaneously therewith. It is preferable that the winding amount of the pulling wire is smaller than the amount of an operation required to rotate the rotational roller. By doing so, the pulling wire can be wound slowly, and moreover the stent accommodation cylindrical member 5 is allowed to move toward the proximal side of the stent delivery device slowly and favorably. In this embodiment, because the outer diameter of the winding shaft portion is smaller than that of the rotational roller, the winding amount of the pulling wire is allowed to be smaller than the amount of the operation required to rotate the rotational roller.

The outer diameter of the winding shaft portion 63 is favorably in the range of 1 to 60 mm and more favorably in the range of 3 to 30 mm. The outer diameter of the rotational roller is favorably 1 to 20 times and more favorably 1 to 10 times larger than that of the winding shaft portion. More specifically, the outer diameter of the rotational roller is favorably in the range of 10 to 60 mm and more favorably in the range of 15 to 50 mm.

The rotational roller and the winding shaft portion does not necessarily have to be formed integrally, but the winding shaft portion may be constructed of a separate member which follows the rotation of the rotational roller. As the transmission system of the rotational roller, it is possible to use a gear type, a belt type, and the like. It is preferable that surfaces of parts which have a possibility of contact with the surface of the rotational roller 61 in operating the rotational roller 61 is not slippery. For example, it is preferable to treat surfaces of parts which have a possibility of contact with the surface of the rotational roller 61 in operating the rotational roller 61 by knurling treatment, emboss treatment, application of a high-frictional material, and the like.

The operation portion 100 of the stent delivery device has the locking mechanism for releasably locking the rotation of the pulling wire winding mechanism, and the reverse rotation prevention mechanism for preventing the rotation of the pulling wire winding mechanism in a direction opposite to a pulling wire winding direction.

As shown in FIGS. 41 through 43, the rotational roller 61 has the gear portion 62 which is coaxial therewith and rotates together therewith. As shown in FIG. 43, the gear portion 62 is provided on the other side surface (in other words, surface opposite to surface on which winding shaft portion 63 is provided) of the rotational roller 61. Thus the gear portion 62 and the winding shaft portion 63 are partitioned from each other by a wall constructed of the rotational roller.

The rotational roller 61 has the portion partly exposed from the open portion 98. The exposed portion serves as the operation portion. The roller 61 has other end 64a provided on one side surface (side surface of gear) of the rotating shaft thereof and the one end 64b provided on the other side surface (side surface of winding shaft) thereof.

An urging means 92 for urging the rotational roller 61 toward the open portion 98 of the housing 101 is provided inside the housing 101. More specifically, an urging member 92b of the urging means 92 urges the roller 61. The housing 101 accommodates the locking rib 99 capable of penetrating into the gap between adjacent projected portions formed on the gear portion 62 of the roller 61. Therefore the rotating roller 61 has a state shown in FIG. 42, when the rotating roller 61 is urged by the urging member 92b. Thus the locking rib 99 engages the projected portion of the gear portion 62. Thus the rotating roller 61 is incapable of rotating. When the rotating roller 61 is pressed in the direction in which it moves away from the locking rib 99, the one end 64b and other end 64a of the rotating shaft of the roller 61 move inside the bearing portions 94b and 94a respectively provided in the housing 101. Thereby the rotational roller 61 becomes rotatable. Thus the operation portion 100 of this embodiment prevents the rotation of the rotational roller 61, when it is not pressed and has the locking mechanism for releasably locking the rotation of the pulling wire winding mechanism.

The operation portion of this embodiment has the reverse rotation prevention mechanism composed of the urging means 92 having the urging member 92b and the above-described gear portion 62. The reverse rotation prevention mechanism prevents the rotation of the pulling wire winding mechanism in the direction opposite to the pulling wire winding direction. The urging means 92 has the urging member 92b and the fixing member 92a for fixing the urging member 92b to the housing 101. As the urging member 92b, a leaf spring is used. The leaf spring extends from the fixing member 92a to a lower portion of the gear portion 62 through the rear (direction opposite to distal portion of operation portion) of the gear portion 62 in such a way that the distal end of the leaf spring engages the projected portions disposed at the lower portion of the gear portion 62. Because the leaf spring is pressed against the gear portion 62, with the leaf spring in contact therewith, as described above, the roller 61 is urged toward the open portion 98 of the housing. The roller 61 is pressed as described above and the roller 61 is rotatable. The roller 61 is rotatable in the direction (pulling wire-winding direction) shown with the arrow of FIG. 42. If an operation of rotating the roller 61 in the opposite direction is performed, the projected portion of the gear portion 62 and the distal end of the urging member 92b engage each other. Thereby the rotation of the roller 61 is prevented. Thereby the reverse rotation prevention mechanism prevents the rotation of the pulling wire winding mechanism in the direction opposite to the pulling wire winding direction.

The diameter of the gear portion 62 is set smaller than that of the rotational roller. The outer diameter of the gear portion 62 is favorably in the range of 10 to 60 mm and more favorably in the range of 15 to 50 mm. The number of cogs thereof is favorably in the range of 4 to 200 and more favorably in the range of 4 to 70.

As shown in FIG. 43, in the operation portion 100, the urging member (leaf spring) 92 penetrates between the inner surface of the housing 101 and the side surface of the rotational roller 61, and the distal end thereof contacts the gear portion 62. Therefore the movement of the urging member 92b in a lateral direction is prevented by the inner surface of the housing 101 and the side surface of the rotational roller 61.

The shaft of the collar member 102 of the operation portion 100 is supported with the pin 103 at its one end. The collar portion 104 at the other side of the collar member 102 accommodates the winding shaft portion 63 and forms an annular space between the collar portion 104 and the winding shaft portion 63. The annular space is not very large and formed annularly between collar portion 104 and the outer surface of the wound wire. As shown in FIG. 43, a thick portion 102a having a width equal to or a little smaller than the inner-side dimension of the housing 101 is formed at a portion, of the collar member 102, supported with the pin 103. The portion from the thick portion 102a to the collar portion 104 is formed as a thin portion 102b capable of penetrating between the inner surface of the housing 101 and the side surface of the rotational roller 61. The thickness of the thin portion 102b is set equally to or a little smaller than the dimension between the inner surface of the housing 101 and the side surface of the rotational roller 61. Therefore the collar member 102 prevents a movement of the rotational roller 61 in a lateral direction (horizontal direction) toward the winding shaft portion. Further the urging member 92b prevents a movement of the rotational roller 61 toward the gear portion. Thereby the rotational roller 61 is prevented from shaking.

The method of using the stent delivery device 50 of the present invention is described below with reference to the drawings.

In most cases, initially as shown in FIGS. 24 and 25, one end of the guide wire implanted in a human body is inserted into the opening 24 of the distal-end member 25 to expose the guide wire (not shown) from the proximal-side opening 23. Thereafter the guide wire is inserted into a guide catheter (not shown) disposed in the human body. Thereafter the stent delivery device 50 is moved forward along the guide wire to dispose a stent accommodation portion of the stent accommodation cylindrical member 5 in a desired stenosed portion.

After the rotational roller 61 of the operation portion 9 is pressed, the rotational roller is rotated in the direction shown with the arrow of FIG. 35. Thereby the stent accommodation cylindrical member 5 axially moves to the proximal side of the stent delivery device. At this time, the rear end surface of the stent 3 contacts the distal end surface of the stent-locking portion 22 of the distal-side tube 2 and is locked thereto. Thereby as the stent accommodation cylindrical member 5 moves, the stent 3 is discharged from the opening at the distal end of the stent accommodation cylindrical member 5. As shown in FIG. 31, owing to the discharge, the stent 3 self-expands, expands the stenosed portion, and is implanted therein.

A stent delivery device 60 of another embodiment of the present invention is described below.

Figure 37:
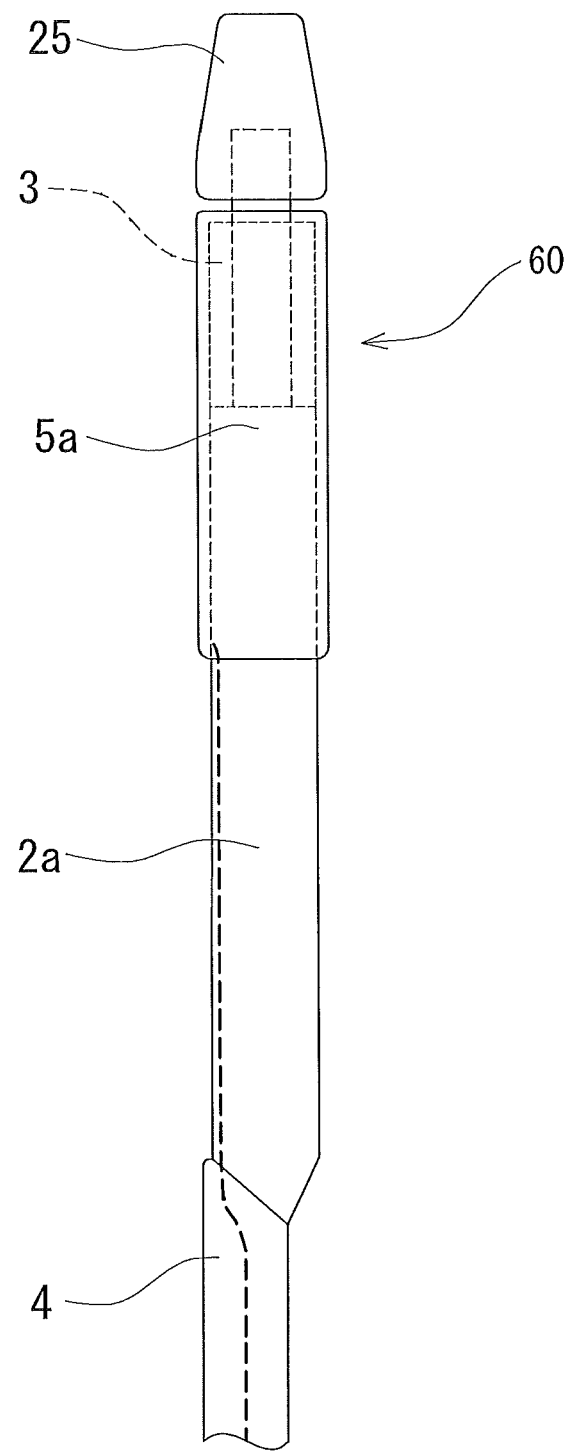
FIG. 37 is a schematic enlarged outlook view showing a neighborhood of the distal portion of the stent delivery device of another embodiment of the present invention.

FIG. 37 is a schematic enlarged outlook view showing a neighborhood of the distal portion of the stent delivery device of another embodiment of the present invention.

The enlarged sectional view of FIG. 37 showing the neighborhood of the distal portion of the stent delivery device is similar to that shown in FIG. 11. Thus FIG. 11 is referred to. The explanatory view for explaining the action of the stent delivery device shown in FIG. 37 is similar to that shown in FIG. 12. Thus FIG. 12 is referred to.

The stent delivery device 60 is the same as the stent delivery device 50 except that the stent delivery device 60 does not have the intermediate tube and is different from that of the latter in the mode of the distal-side tube. Other construction of the former is the same as that of the latter. Thus the same parts of the former as those of the latter are denoted by the same reference numerals as those of the latter, and description thereof is omitted herein.

The stent delivery device 60 is the same as the stent delivery device 10 in that the stent delivery device 60 does not have the intermediate tube and is different from that of the latter in the mode of the distal-side tube. Thus the stent delivery device 60 is described briefly with reference to the description of the stent delivery device 10.

The stent delivery device 60 of this embodiment has the distal-side tube 2a; the proximal-side tube 4; the stent accommodation cylindrical member 5a; the stent 3; and the pulling wire 6.

As shown in FIGS. 37, 11, and 12, as the stent accommodation cylindrical member 5a, a cylindrical member having almost the same diameter is used. A slit 59 as shown in FIG. 16 may be formed in the stent accommodation cylindrical member 5a. As shown in FIG. 16, a projected portion 29 formed on the outer surface of the distal-side tube is capable of advancing into the slit 59. In this embodiment, until the distal end of the slit 59 contacts the projected portion 29, the stent accommodation cylindrical member 5a is movable toward the proximal side of the stent delivery device. Thus the length of the slit 59 is set equal to or a little longer than the length in the range from the proximal end of the stent 3 accommodated in the stent accommodation cylindrical member 5a to the distal end of the stent accommodation cylindrical member 5a. As shown in FIG. 12, owing to the discharge from the stent accommodation cylindrical member 5, the stent 3 self-expands and expands the stenosed portion and is implanted therein.

The stent accommodation cylindrical member 5a is the same as that of the stent delivery device 1 of the above-described embodiment. The stent 3 is accommodated in the stent accommodation cylindrical member 5a at its distal portion. The stent 3 is the same as that of the stent delivery device 1 of the above-described embodiment.

As shown in FIGS. 37, 11, and 12, the distal-side tube 2a is a tubular body having the guide wire lumen 21 penetrating through the distal-side tube 2a from its distal end to its proximal end. The distal-side tube 2a has a distal portion formed by a distal-end member 25 fixed to the distal end thereof and has a distal-end opening 24. The distal portion formed by the distal-end member 25 may be formed integrally with the distal-side tube 2a. The distal-side tube 2a is the same as that of the stent delivery device 1 of the above-described embodiment.

In this embodiment, the outer diameter of the proximal-side tube 4 is also set smaller than a portion, having a maximum diameter, which is disposed in a region of the stent delivery device 60 distal from the proximal-side tube 4. More specifically, in this embodiment, the outer diameter of the stent accommodation cylindrical member 5a is set maximum. The outer diameter of the proximal-side tube 4 is set smaller than the outer diameter of the stent accommodation cylindrical member 5a. As shown in FIGS. 37 and 11, in this embodiment, the distal portion of the proximal-side tube 4 is fixed to the proximal portion of the distal-side tube 2a by shifting the axis of the proximal-side tube 4 in a direction away from the proximal-side opening 23 with respect to the axis of the distal-side tube 2a.

The distal-side tube 2a extends from the vicinity of the fixing point 6d at which the pulling wire 6 and the stent accommodation cylindrical member 5a are fixed to each other to the proximal side of the stent delivery device. The distal-side tube 2a has a passage 27 for the pulling member. In this embodiment, the passage 27 for the pulling member is formed of a concave portion extended axially on the outer surface of the distal-side tube 2a. The passage 27 for the pulling member may be a lumen extended in penetration through the wall of the distal-side tube 2a.

In the stent delivery device 60 of this embodiment, by operating the rotational roller 61 of the operation member 9 of the pulling wire 6 toward the proximal end of the stent delivery device, the stent accommodation cylindrical member 5a axially moves to the proximal side of the stent delivery device. At this time, the rear end surface of the stent 3 contacts the proximal end 26a of the small-diameter portion 26 of the distal-side tube 2a and is locked thereto. Thereby as the stent accommodation cylindrical member 5a moves, the stent 3 is discharged from the opening at the distal end of the stent accommodation cylindrical member 5a. As shown in FIG. 12, the stent 3 self-expands and expands the stenosed portion and is implanted therein.

In all the above-described embodiments, a plurality of (more specifically, two) the pulling members may be provided.

Figure 38:
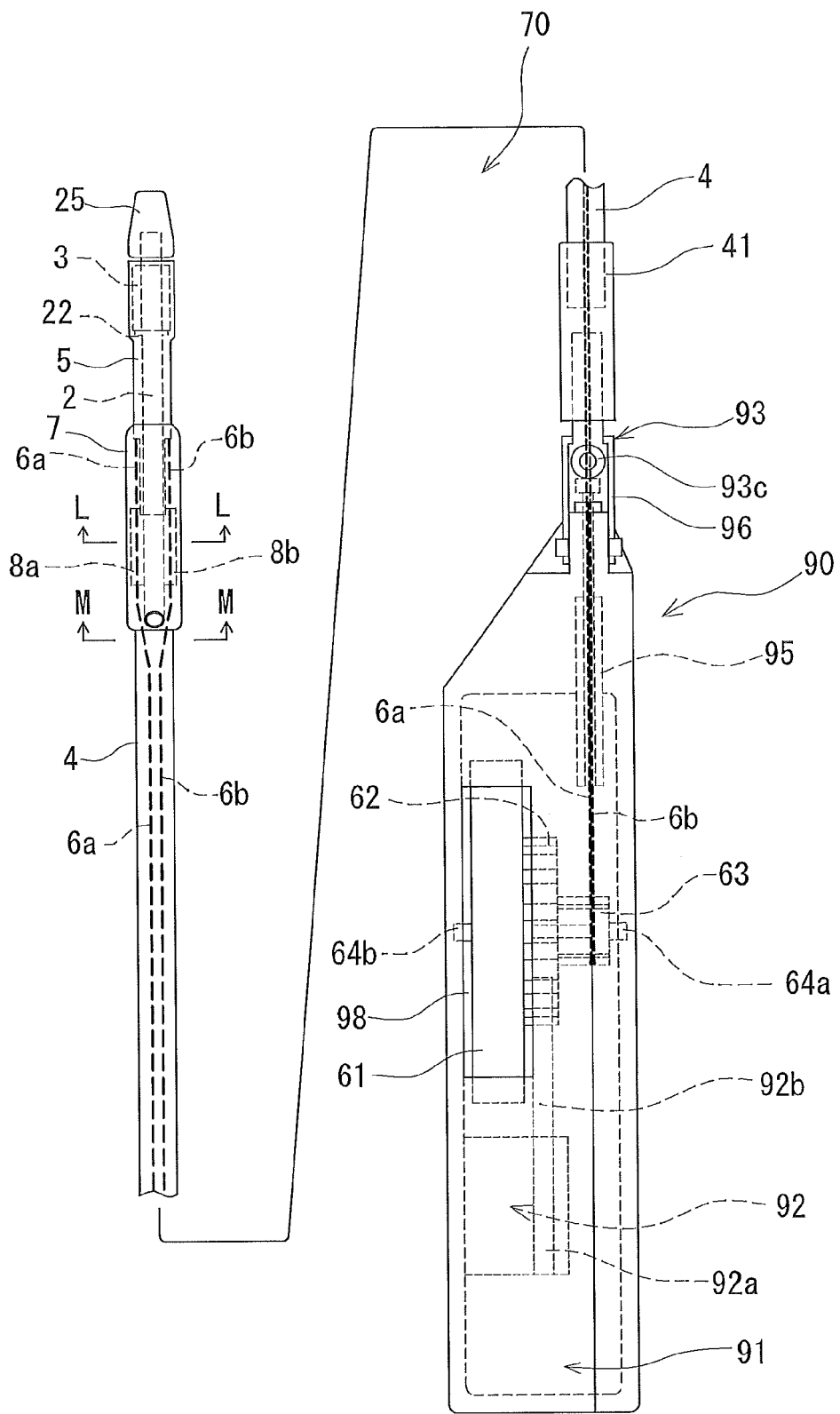
FIG. 38 is a partially schematic enlarged outlook view showing a stent delivery device of another embodiment of the present invention.
Figure 39:
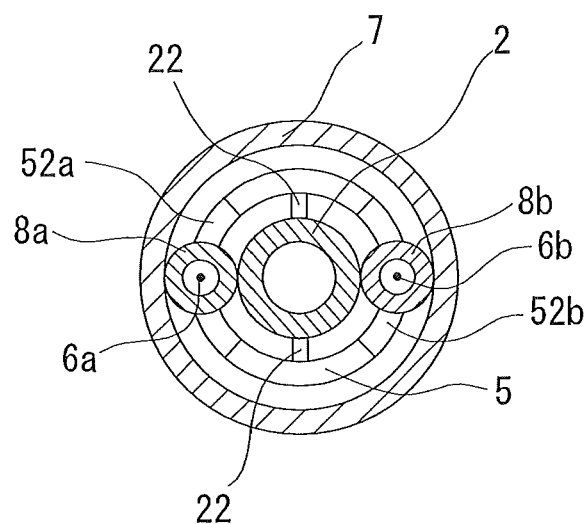
FIG. 39 is an enlarged sectional view taken along a line L-L of FIG. 38.
Figure 40:
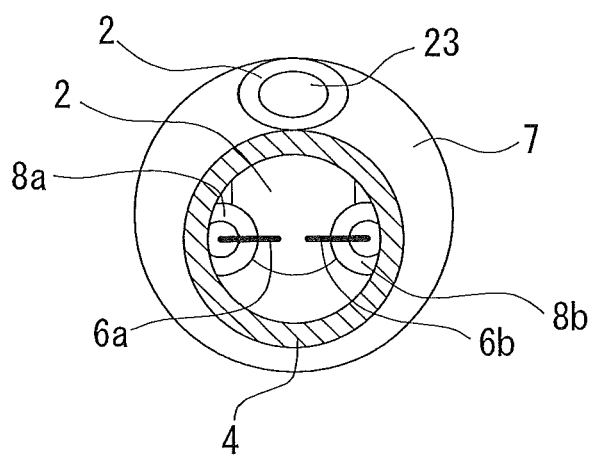
FIG. 40 is an enlarged sectional view taken along a line M-M of FIG. 38.

A stent delivery device 70 shown in FIGS. 38 through 40 has tow pulling wires.

FIG. 38 is a partially schematic enlarged outlook view showing a stent delivery device of another embodiment of the present invention. FIG. 39 is an enlarged sectional view taken along a line L-L of FIG. 38. FIG. 40 is an enlarged sectional view taken along a line M-M of FIG. 38.

The stent delivery device 70 is the same as the stent delivery device 50 except that the stent delivery device 70 has two pulling members and that there are some differences generated caused thereby. Other construction of the former is the same as that of the latter. Thus the same parts of the former as those of the latter are denoted by the same reference numerals as those of the latter, and description thereof is omitted herein. The above-described stent delivery device 60 may be provided with two pulling wires. The construction having two pulling wires is the same as that of the above-described stent delivery device 20.

As shown in FIGS. 38 and 39, the stent accommodation cylindrical member 5 of the stent delivery device 70 has two slits 52a, 52b extended from the proximal end of the stent accommodation cylindrical member 5 toward its distal end and disposed at positions opposed to each other. In correspondence to the positions of the slits 52a, 52b, the distal-side tube 2 has two tubular members 8a, 8b formed at positions opposed to each other.

Two pulling members 6a, 6b are fixed to the proximal portion of the stent accommodation cylindrical member 5 at positions opposed to each other. As shown in FIGS. 38 through 40, the pulling wire 6a extends inside the proximal-side tube 4 in penetration through the tubular member 8a and fixed to the winding shaft of the operation portion 9 at the proximal portion thereof. Similarly the pulling wire 6b extends inside the proximal-side tube 4 in penetration through the tubular member 8b and fixed to the winding shaft of the operation portion 9 at the proximal portion thereof. When the two pulling members 6a, 6b are used, they may be integrated with each other at the proximal portion of the stent accommodation cylindrical member 5.

In the stent delivery device of the present invention, it is possible to prevent the movement of the stent toward the distal end thereof and easy to insert the stent delivery device to a desired portion of an organ, provided that the distal-side tube of the stent delivery device has a projected portion, for preventing the movement of the stent, which is provided at the side distal from the distal end of the stent and provided that the distal side of the above-described projected portion is gradually decreased in its diameter toward the distal end thereof.

In the stent delivery device of the present invention, it is possible to pull a pulling wire favorably, provided that the stent delivery device has a member, for maintaining the position of the pulling wire, which is disposed on the outer surface of the distal-side tube and has a passage through which the pulling wire is capable of penetrating.

In the stent delivery device of the present invention, it is possible to move the stent accommodation cylindrical member to move favorably toward the proximal side of the stent delivery device, provided that a projected portion is provided on an outer surface of the distal-side tube and that the stent accommodation cylindrical member has a slit which extends from a distal end thereof toward a distal side thereof and into which the projected portion is capable of moving.

In the stent delivery device of the present invention, it is possible to prevent the stent accommodation cylindrical member from moving excessively, provided that the stent delivery device has a portion for restricting a movement distance of the stent accommodation cylindrical member toward the proximal side of the stent delivery device.

A stent delivery device of another embodiment of the present invention is described below.

Figure 44:
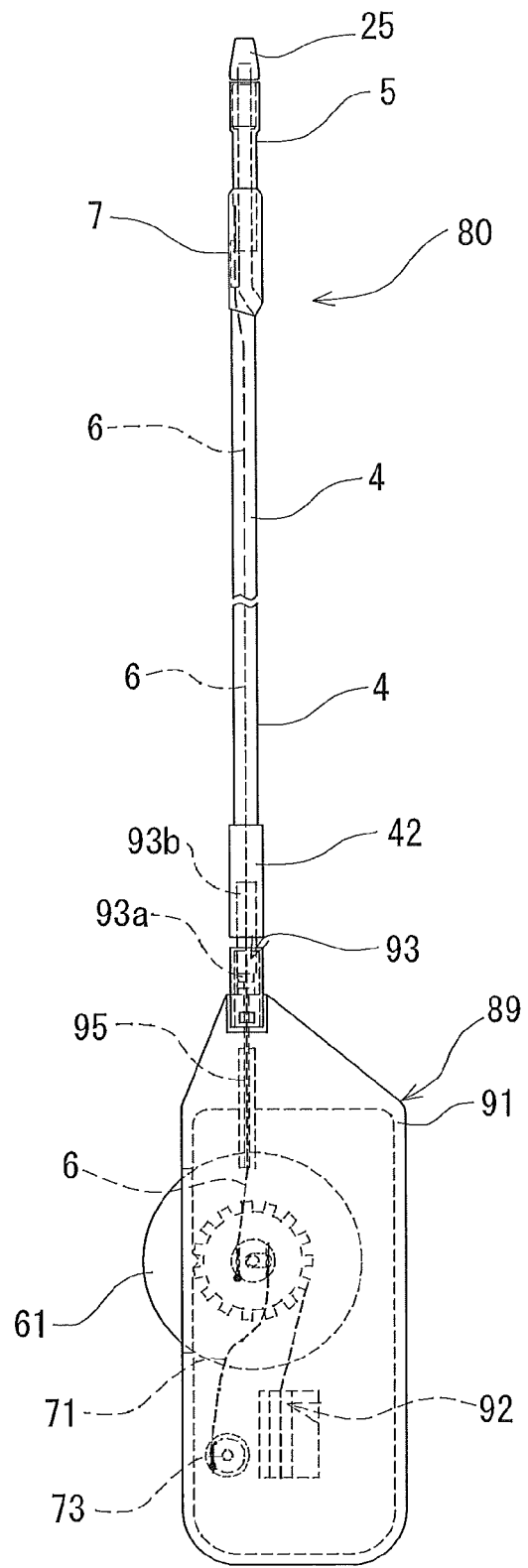
FIG. 44 is a partially schematic front view showing a stent delivery device of an embodiment of the present invention.
Figure 45:
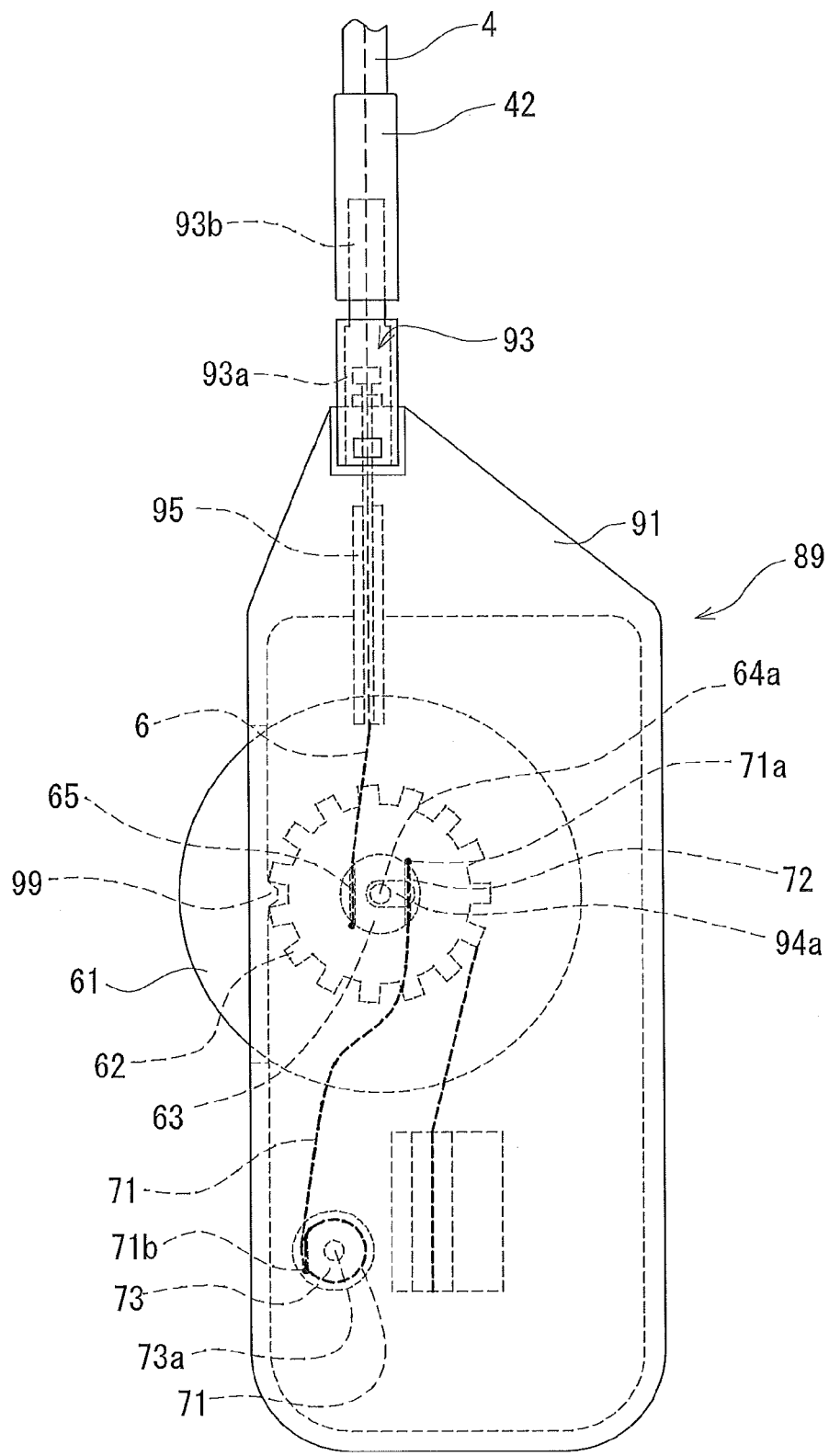
FIG. 45 is an enlarged outlook view showing the neighborhood of the operation portion of the stent delivery device shown in FIG. 44.
Figure 46:
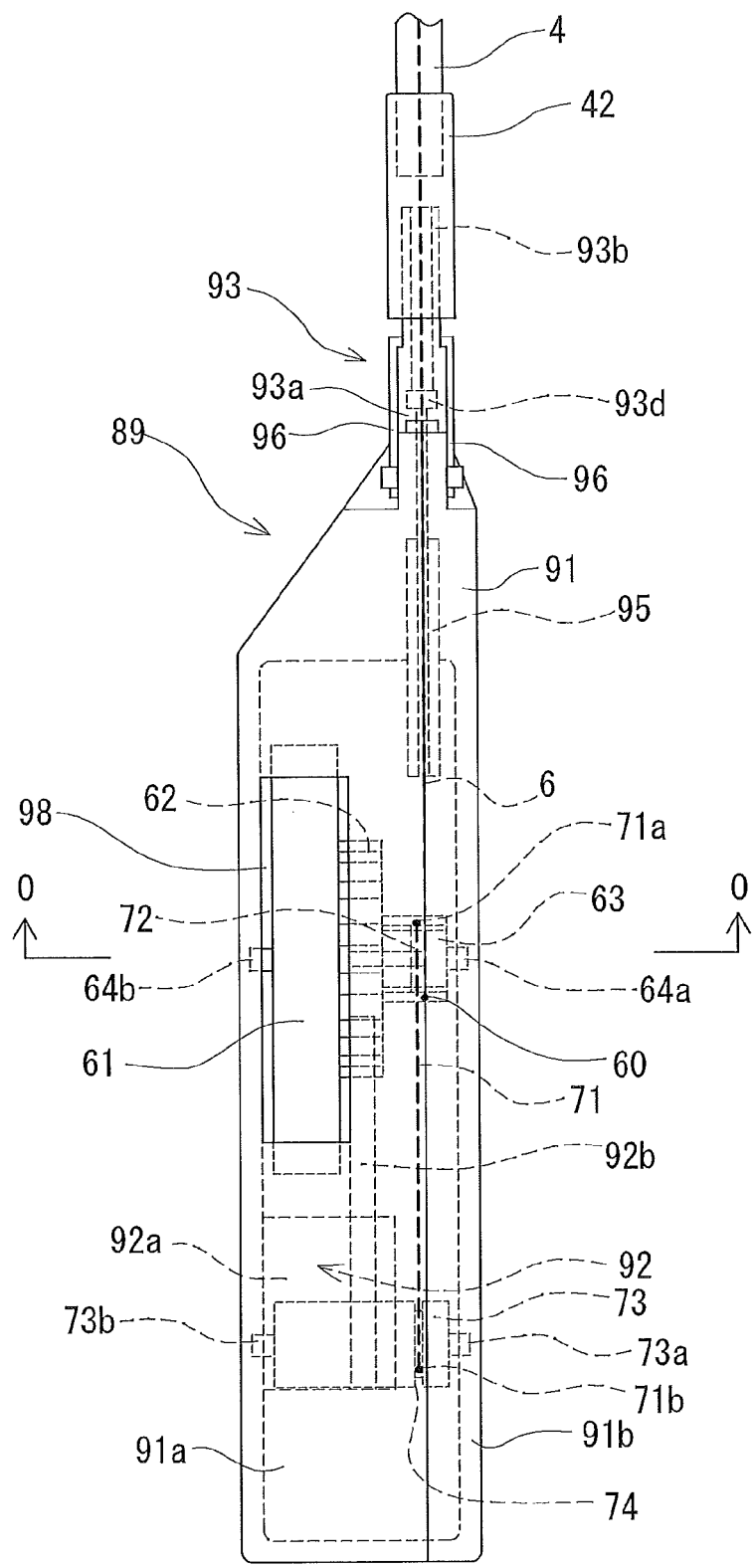
FIG. 46 is an enlarged left-hand side view showing the neighborhood of the operation portion of the stent delivery device shown in FIG. 44.
Figure 47:
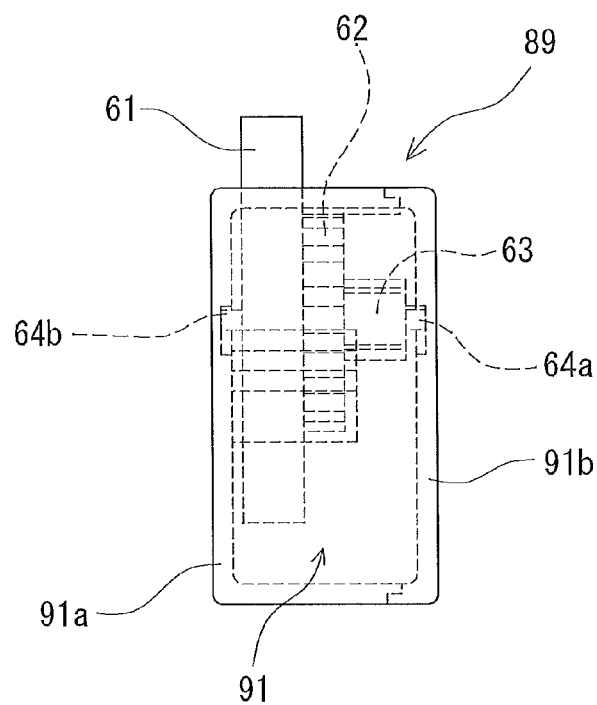
FIG. 47 is an enlarged bottom view showing the operation portion of the stent delivery device shown in FIG. 44.
Figure 48:
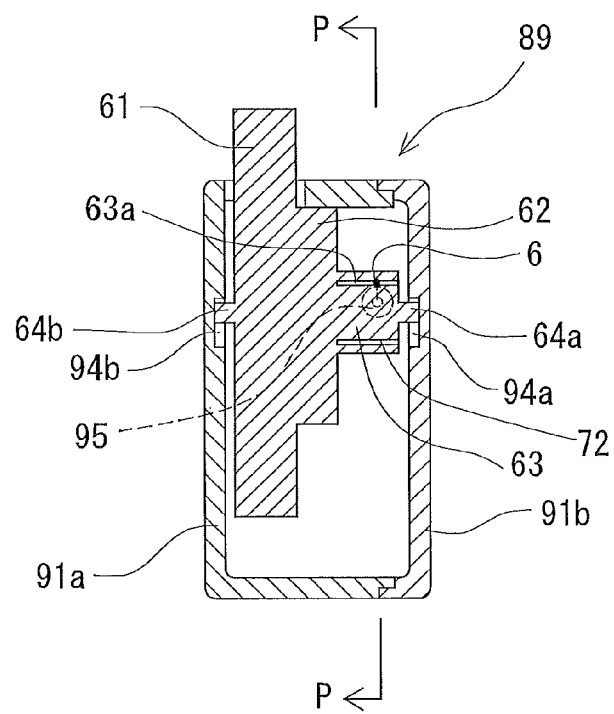
FIG. 48 is a sectional view taken along a line O-O of FIG. 46.
Figure 49:
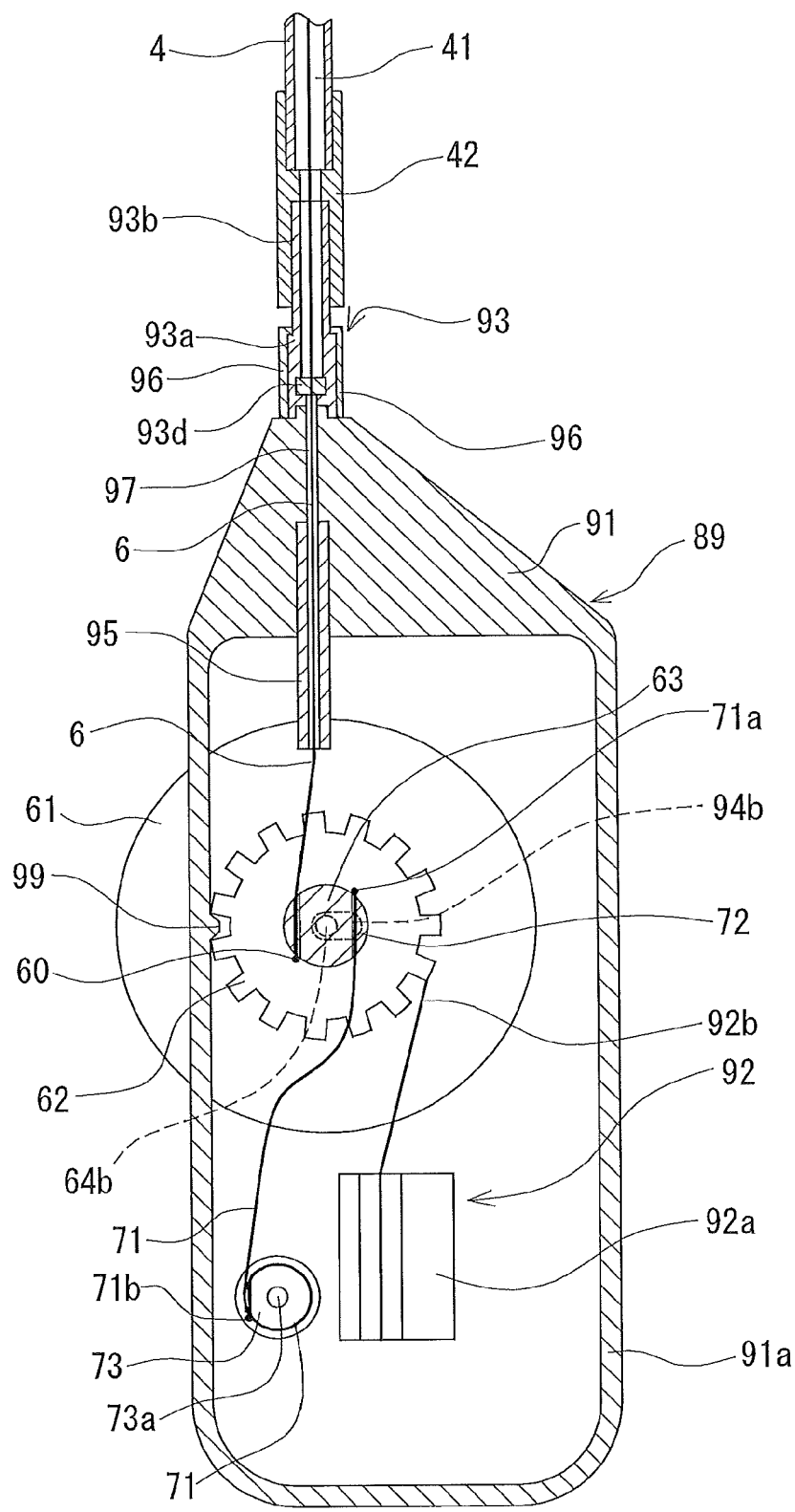
FIG. 49 is an enlarged sectional view taken along a line P-P of FIG. 48.
Figure 50:
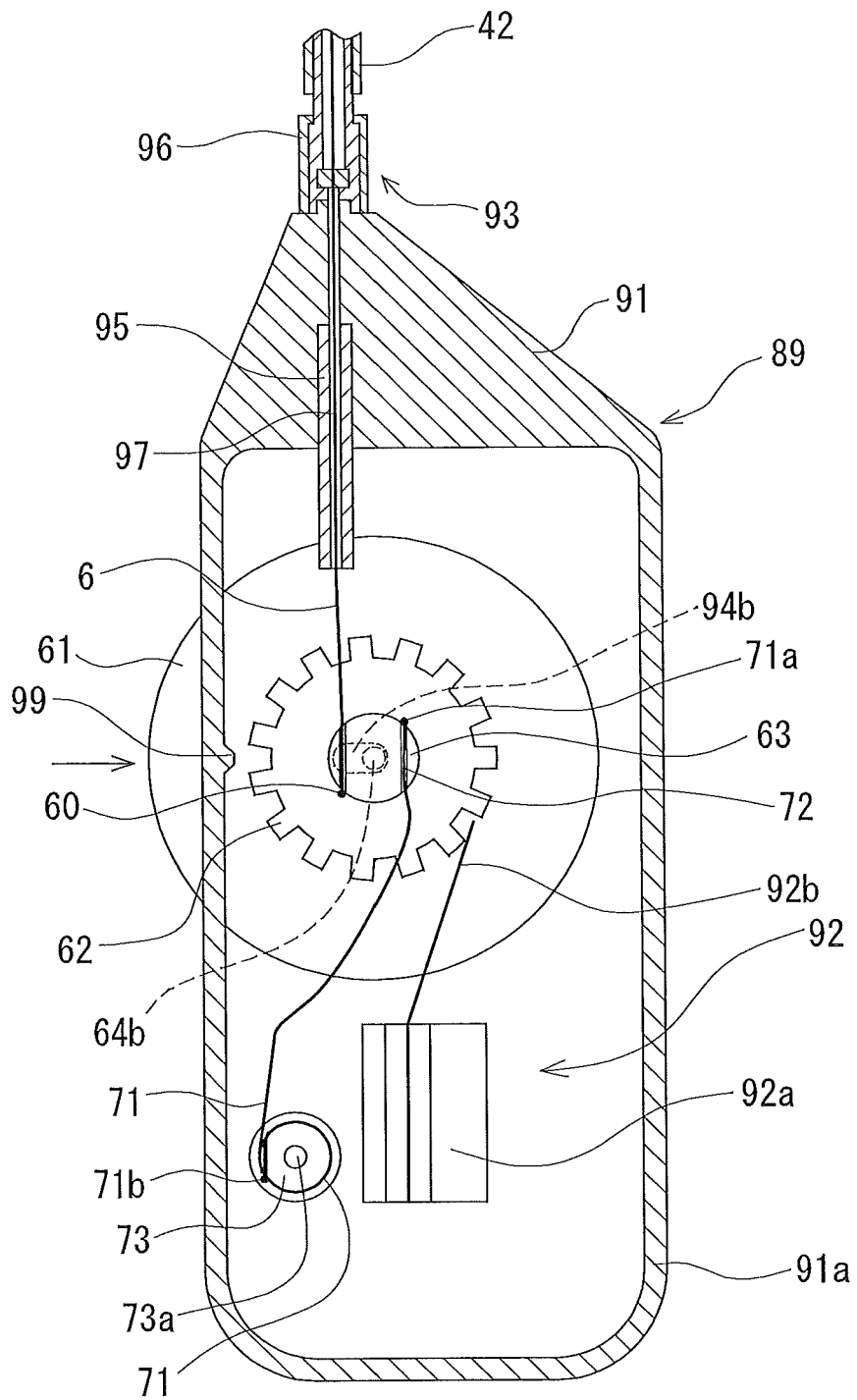
FIG. 50 is an explanatory view for explaining the operation of the stent delivery device of the present invention.
Figure 51:
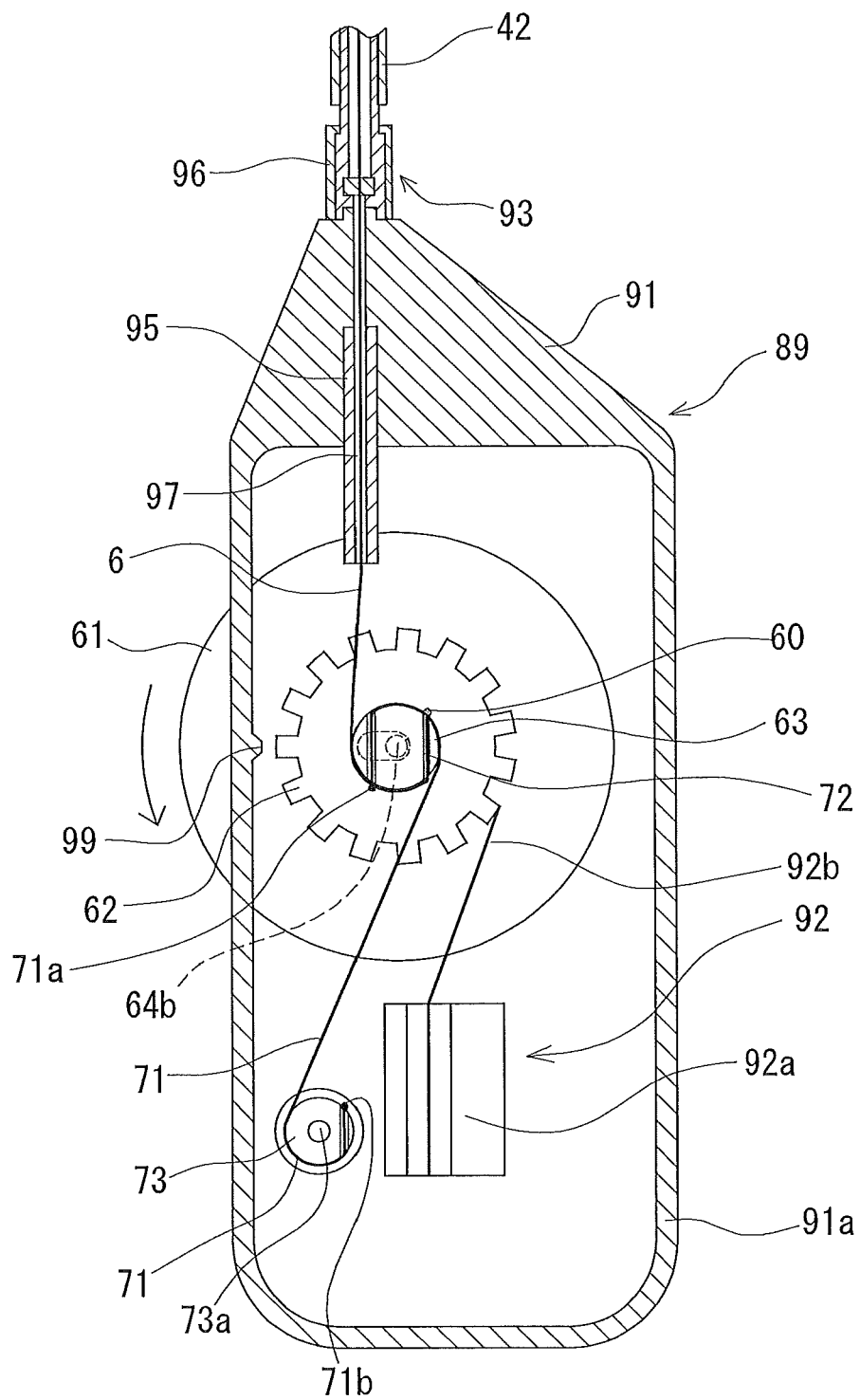
FIG. 51 is an explanatory view for explaining the operation of the stent delivery device of the present invention.

FIG. 44 is a partially schematic front view showing a stent delivery device of an embodiment of the present invention. FIG. 45 is an enlarged outlook view showing the neighborhood of the operation portion of the stent delivery device shown in FIG. 44. FIG. 46 is an enlarged left-hand side view showing the neighborhood of the operation portion of the stent delivery device shown in FIG. 44. FIG. 47 is an enlarged bottom view showing the operation portion of the stent delivery device shown in FIG. 44. FIG. 48 is a sectional view taken along a line O-O of FIG. 46. FIG. 49 is an enlarged sectional view taken along a line P-P of FIG. 48. FIG. 50 and FIG. 51 are an explanatory view for explaining the operation of the stent delivery device of the present invention.

The basic construction of a stent delivery device 80 is the same as that of the stent delivery device 50 of the above-described embodiment. In the stent delivery device 80 of this embodiment, at the proximal portion of the proximal-side tube 4, the stent delivery device 80 includes an operation portion 89 having a pulling wire winding mechanism for winding the pulling wire 6 and moving the stent accommodation cylindrical member 5 to the proximal side of the stent delivery device and a wire winding amount restriction mechanism for restricting the length of a wire wound by the pulling wire winding mechanism.

According to the stent delivery device 80 of the present invention using a self-expandable stent, the opening at the proximal side thereof is disposed not at the proximal end thereof, but at the proximal side of the distal-side tube. Therefore in a stent-implanting operation, it is easy to perform an operation of exchanging the stent delivery device with a stent delivery device of other type. By pulling the pulling wire to the proximal side of the stent delivery device, the stent can be discharged from the stent accommodation cylindrical member. Thus the position movement amount of the stent is very small in an operation of discharging the stent from the stent accommodation cylindrical member. Further the wire for pulling the bound stent to the proximal side of the stent delivery device is prevented from being excessively wound. Thus a catheter is prevented from being curved or damaged.

An operation portion 89 has a housing 91 (91a, 91b). It is preferable that the pulling wire winding mechanism has a rotational roller 61 for operational use (hereinafter referred to as merely rotational roller 61) having a portion exposed from the housing 91 and that by rotating the rotational roller 61, the pulling wire 6 is wound on the rotational roller 61 at its proximal side. This construction allows the operation portion 89 to be compact and an operation of rotating the rotational roller to be accomplished, with the housing 91 being held with a hand. Thus it is possible to perform an operation of discharging the stent from the stent delivery device with one hand.

It is preferable that in a stent delivery device 80, the outer diameter of the proximal-side tube is set smaller than that of the portion, having the maximum diameter, which is disposed in the region of the stent delivery device 80 distal from the proximal-side tube 4. In this construction, even in a state in which the guide wire is extended along the side surface of the proximal-side tube from the opening at the proximal side of the stent delivery device to the proximal side of the stent delivery device, the outer diameter of the proximal-side tube is set almost equally to that of the portion, having the maximum diameter, which is disposed in the region of the stent delivery device distal from the proximal-side tube. Thereby the stent can be inserted into a narrow blood vessel.

The stent delivery device 80 of this embodiment has the distal-side tube 2, the proximal-side tube 4, the stent accommodation cylindrical member 5, the stent 3, the pulling wire 6, and an operation portion 89 having a mechanism for winding the pulling wire 6 and the wire winding amount restriction mechanism.

The stent delivery device 80 of this embodiment has an intermediate tube 7 that encloses the proximal side of the distal-side tube 2 and the proximal side of the stent accommodation cylindrical member 5 and is fixed at a proximal portion thereof to the proximal portion of the distal-side tube 2 and the distal portion of the proximal-side tube 4. In the stent delivery device 80 of this embodiment, the intermediate tube 7 encloses the proximal side of the distal-side tube 2 and the proximal side of the stent accommodation cylindrical member 5 without preventing the stent accommodation cylindrical member 5 from moving toward the proximal side of the stent delivery device 80. The one end portion of the pulling wire 6 is fixed to the stent accommodation cylindrical member 5 inside the intermediate tube 7. The pulling wire 6 passes between the intermediate tube 7 and the distal-side tube 2 and extends into the proximal-side tube 4. This construction is preferable in that the pulling wire is not exposed.

The stent accommodation cylindrical member 5 is the same as that of the stent delivery device 1 of the above-described embodiment. As the stent 3, it is possible to use the self-expandable stent of any types. For example, it is possible to preferably use the stent 3 of the stent delivery device 1 of the above-described embodiment. As shown in FIGS. 24 through 29, the distal-side tube 2 is a tubular body having the guide wire lumen 21 penetrating through the distal-side tube 2 from its distal end to its proximal end. The distal-side tube 2 has a distal portion formed by a distal-end member 25 fixed to the distal end thereof and has a distal-end opening 24. The distal-side tube 2 is the same as that of the stent delivery device 1 of the above-described embodiment. The distal-end member 25 is also the same as that of the stent delivery device 1 of the above-described embodiment. As shown in FIG. 26, the distal-side tube 2 has the stent-locking portion 22 for preventing the stent 3 from moving to the proximal side of the stent delivery device 1. The stent-locking portion 22 is the same as that of the stent delivery device 1 of the above-described embodiment.

As shown in FIGS. 24 through 29, the proximal-side tube 4 is a tubular body extending from its distal end to its proximal end and has the hub 42 fixed to its proximal end. The enlarged outlook view of FIG. 44 showing the distal end of the stent delivery device and the vicinity thereof is similar to that shown in FIG. 25. Thus FIG. 25 is referred to. The enlarged sectional view of FIG. 44 showing the distal end of the stent delivery device and the vicinity thereof is similar to that shown in FIG. 26. Thus FIG. 26 is referred to. The distal portion of the proximal-side tube 4 is joined with the proximal portion of the distal-side tube 2. The proximal-side tube 4 has therein the lumen 41 into which the pulling wire 6 can be inserted. The proximal-side tube 4 is the same as that of the stent delivery device 1 of the above-described embodiment.

The stent delivery device 80 of this embodiment has the intermediate tube 7 which encloses the proximal side of the distal-side tube 2 and the proximal side of the stent accommodation cylindrical member 5 and is fixed at the proximal portion thereof to the proximal portion of the distal-side tube 2 and the distal portion of the proximal-side tube 4. In the stent delivery device 80 of this embodiment, the intermediate tube 7 encloses the proximal side of the distal-side tube 2 and the proximal side of the stent accommodation cylindrical member 5 without preventing the stent accommodation cylindrical member 5 from moving toward the proximal side of the stent delivery device 80. The one end portion of the pulling wire 6 is fixed to the stent accommodation cylindrical member 5 inside the intermediate tube 7. The pulling wire 6 passes between the intermediate tube 7 and the distal-side tube 2 and extends into the proximal-side tube 4.

The proximal portion of the distal-side tube 2 extends inside the intermediate tube 7 and is exposed from the proximal end of the intermediate tube 7. The distal portion of the proximal-side tube 4 penetrates into the proximal portion of the intermediate tube 7. At the proximal portion of the intermediate tube 7, the distal-side tube 2, the proximal-side tube 4, and the intermediate tube 7 are liquid-tightly fixed. The lumen 41 inside the proximal-side tube 4 communicates with the inside of the intermediate tube 7. As shown in FIGS. 2 and 3, the distal portion of the intermediate tube 7 is decreased in its diameter or curved. It is preferable that the distal end of the intermediate tube 7 liquid-tightly contacts the outer surface of the stent accommodation cylindrical member 5 without preventing the movement of the stent accommodation cylindrical member 5. But the distal end of the intermediate tube 7 does not necessarily have to contact the outer surface of the stent accommodation cylindrical member 5. The intermediate tube is the same as that of the stent delivery device 1 of the above-described embodiment.

The stent delivery device 80 has the pulling wire 6 extending inside the proximal-side tube 4, with one end portion thereof fixed to the stent accommodation cylindrical member 5 and being pulled toward the proximal side of the proximal-side tube 4 to move the stent accommodation cylindrical member 5 to the proximal side of the stent delivery device. The pulling wire 6 is the same as that of the stent delivery device 1 of the above-described embodiment.

The stent delivery device 80 of this embodiment has the projected portion (tubular member) 8 provided on the outer surface of the distal-side tube 2 at its proximal side. The projected portion 8 (tubular member) is capable of moving inside the slit 52 of the stent accommodation cylindrical member 5. The projected portion 8 (tubular member) is the same as that of the stent delivery device 1 of the above-described embodiment. The slit 52 is also the same as that of the stent delivery device 80 of the above-described embodiment. The stent delivery device 1 of this embodiment may have a movement distance restriction portion for restricting a movement distance of the stent accommodation cylindrical member 5 toward the proximal side of the stent delivery device. More specifically, owing to the movement of the stent accommodation cylindrical member 5 toward the proximal side of the stent delivery device, the projected portion (in this embodiment, tubular member though which wire penetrates) 8 contacts the distal end of the slit 52, thus preventing a further movement of the stent accommodation cylindrical member 5 toward the proximal side of the stent delivery device.

The stent delivery device 80 of this embodiment has a member for holding the position of the pulling wire. This member is disposed on the outer surface of the distal-side tube 2 and has a passage through which the pulling wire 6 is capable of penetrating. The stent delivery device of this embodiment has a tubular member 8 displaying the function of the member for holding the position of the pulling wire and the function of the above-described projected portion. The member for holding the position of the pulling wire is the same as that of the stent delivery device 1 of the above-described embodiment.

As shown in FIGS. 44, 45, 46 through 51, the stent delivery device 80 of the present invention has a operation portion 89 fixed to at the proximal end of the proximal-side tube 4, namely, to a hub 42 provided at the proximal end of the proximal-side tube 4.

The operation portion 89 of the stent delivery device 80 has the wire winding amount restriction mechanism in addition to the pulling wire winding mechanism. Further the operation portion 89 of the stent delivery device 80 has the locking mechanism for releasably locking the rotation of the pulling wire winding mechanism, and the reverse rotation prevention mechanism for preventing the rotation of the pulling wire winding mechanism in the direction opposite to the pulling wire winding direction.

The operation portion 89 has the housing 91 composed of the body 91a and the covering member 91b sealing the open portion of the body 91a. The connector 93 which is connected with the hub 42 is fixed to the distal portion of the housing 91. The housing 91 has the pulling wire passage 97 extended from the distal end of the distal portion thereof to the inside thereof. The connector 93 is fixed to the distal portion of the housing 91 by means of the fixing member 96 in such a way that a passage inside the connector 93 communicates with the pulling wire passage 97.

As shown in FIGS. 45, 46, and 49, the connector 93 includes a hollow body 93a, a connection port 93b extended from the body 93a, and a sealing member 93d holding the pulling wire 6 slidably and liquid-tightly. The connection port 93b is mounted at the proximal portion of the hub 42 of the proximal-side tube 4. The connector 93 may have a side port 93c communicating with the inside of the body thereof.

The operation portion 89 of the stent delivery device 80 is the same as operation portion 9 of the stent delivery device 50 of the above-described embodiment except that the construction of the wire winding amount restriction mechanism of the former is different from that of the latter.

As shown in FIGS. 44 through 51, the stent delivery device of this embodiment has the wire winding amount restriction mechanism. The wire winding amount restriction mechanism of this embodiment is constructed of a linear member 71, having a predetermined length, whose one end 71b is held by the operation portion. The other end 71a of the linear member 71 is fixed to the winding shaft portion 63 of the rotational roller 61 or a linear member-winding shaft portion (not shown) provided separately from the winding shaft portion. After a predetermined amount of the linear member 71 is wound around the winding shaft portion 63 or around the linear member-winding shaft portion by the rotation of the rotational roller 61 in a wire-winding direction, the linear member 71 cannot further wound.

More specifically, the operation portion 89 accommodates a bobbin 73 on which the linear member 71 is wound, with one end 71b of the linear member 71 held thereby. As exemplified in FIG. 58, the bobbin 73 has a rotational shaft having two end portions 73a, 73b. The bobbin 73 can be rotated by the rotation of the rotational shaft. The bobbin 73 further has an annular groove 74 on which the linear member is wound and a groove or a hole 75 communicating with the annular groove 74. The other end 71a of the linear member 71 is held by the winding shaft portion 63 of the rotational roller 61. More specifically, the other end of the linear member is inserted into a slit 72 (see FIG. 48) formed on the rotational roller 61, and the other end 71a bulged in a width larger than the width of the slit 72 is held by the winding shaft portion 63.

Therefore as shown in FIGS. 50 and 51, when the rotational roller 61 is rotated in the direction in which the pulling wire 6 is wound, the pulling wire held by the winding shaft portion 63 is wound thereon, and the linear member 71 held by the winding shaft portion 63 is also wound thereon. When the linear member wound around the bobbin is all fed out as a result of rotation of the bobbin 73 with the progress of the winding of the linear member 71, the bobbin is nonrotatable. Thereby the rotational roller is incapable of further rotating. Thus the pulling wire is prevented from being excessively pulled.

In this embodiment, the linear member 71 is wound around the winding shaft portion 63. But in addition, it is possible to provide the rotational roller 61 with the linear member winding shaft separately from the winding shaft portion 63 and wind the linear member around the linear member winding shaft.

It is preferable that the winding effective length (in other words, length of the rotational roller that can be wound around shaft portion) of the linear member 71 is a little longer than the axial length of the stent. When not only the pulling wire but also the linear member 71 is wound around the winding shaft portion 63, the winding amount of the pulling wire and that of the linear member for the rotational roller are equal to each other. Thus the winding effective length of the linear member can be set easily.

As the material for forming the linear member 71, any materials difficult to break can be preferably used. Further materials difficult to stretch can be also preferably used. Thus the following substances can be used: stainless steel wire (preferably, high tensile stainless wire for spring); music wire (preferably, nickel-plated or chromium-plated music wire); super-elastic alloy wire; wires made of metal such as Ni—Ti alloy, Cu—Zn alloy, Ni—Al alloy, tungsten, tungsten alloy, titanium, titanium alloy, cobalt alloy; tantalum, comparatively high rigidity polymeric materials such as polyamide, polyimide, ultra-high-molecular-weight polyethylene, polypropylene, and fluororesin; and combinations of these substances.

Figure 53:
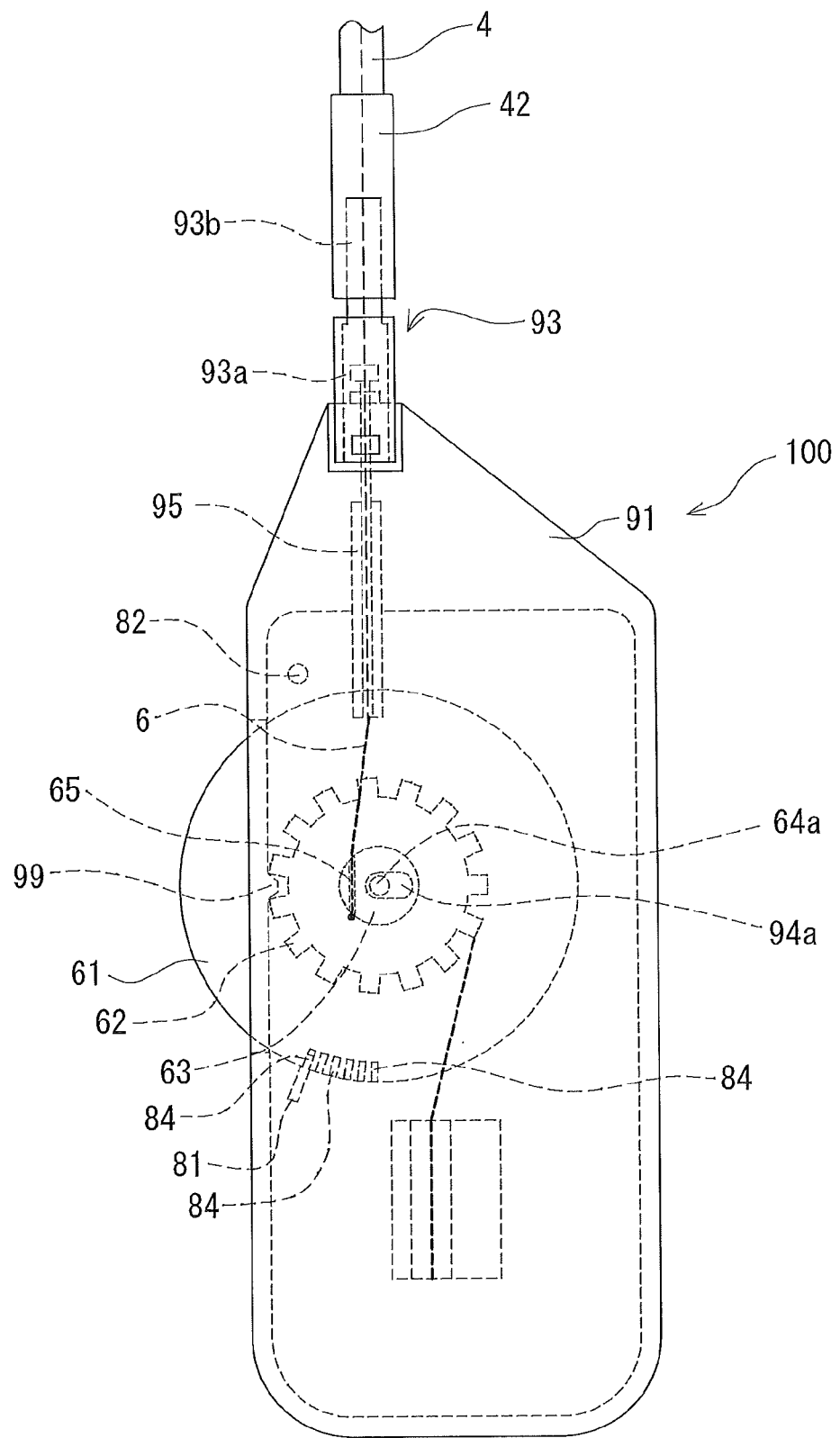
FIG. 53 is an enlarged front view showing the neighborhood of an operation portion of a stent delivery device of another embodiment of the present invention.

The wire winding amount restriction mechanism is not limited to the one described in the above-described embodiment, provided that a wire winding amount restriction mechanism restricts the winding amount of the wire to be pulled by the pulling wire winding mechanism. The above-described wire winding amount restriction mechanism of the above-described type restricts the rotatable amount of the rotational roller. The operation portion 100 shown in FIGS. 53 and 54 is capable of serving as the wire winding amount restriction mechanism of this type.

The operation portion 100 serving as the wire winding amount restriction mechanism includes a projected portion 81 and a locking portion 82 with which the rotational roller 61 provided in the operation portion 100 contacts after it rotates in a predetermined amount in the wire-winding direction and which prevents a further rotation of the rotational roller 61.

Figure 54:
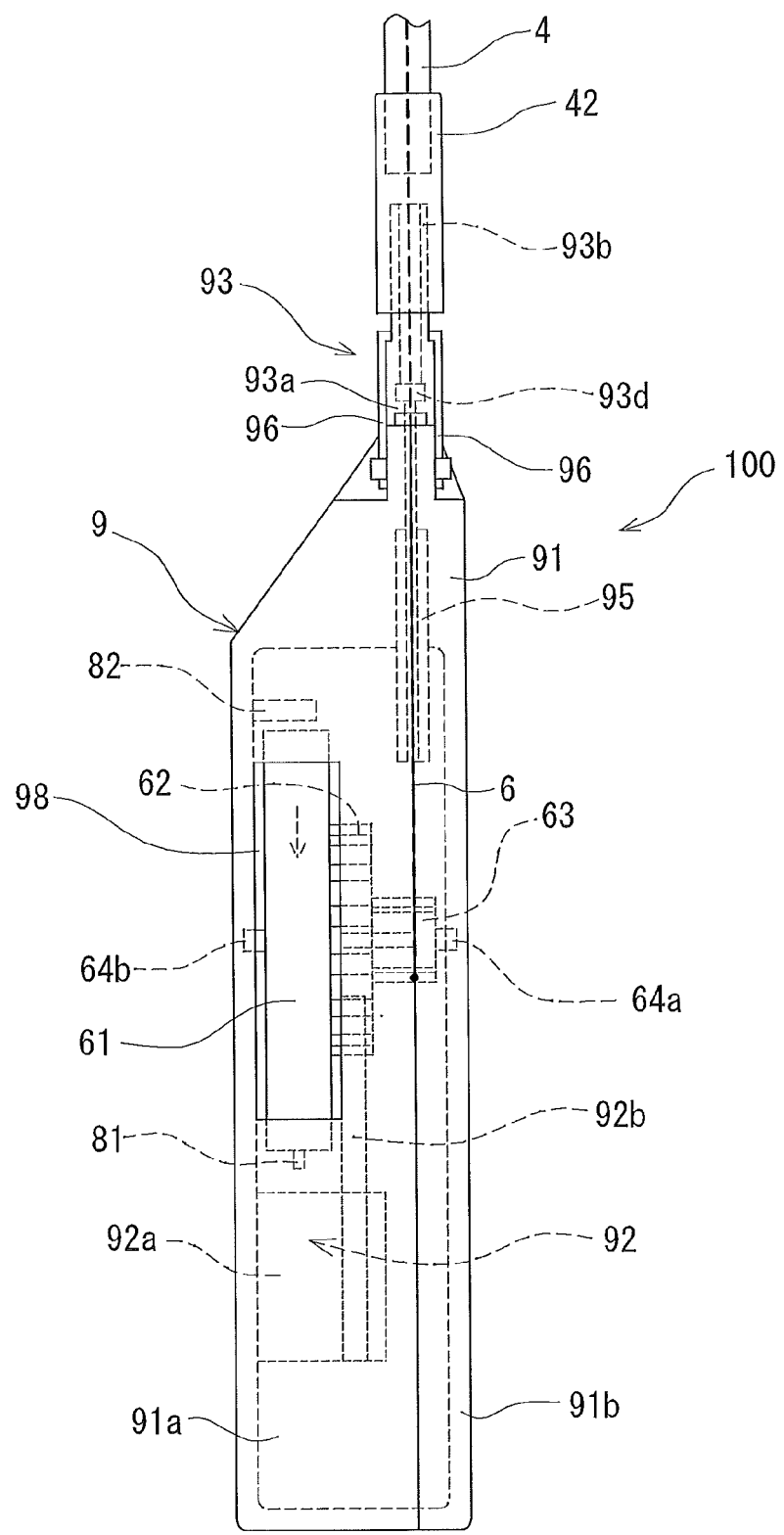
FIG. 54 is a left-hand side view showing the neighborhood of the operation portion of the stent delivery device shown in FIG. 53.

In the operation portion 100, when the rotational roller 61 is rotated in a direction with the arrow of FIG. 54, the pulling wire 6 is wound. But when the projected portion 81 contacts the locking portion 82, the roller 61 cannot be rotated further. Thus the pulling wire cannot be wound further. In this operation portion, the length of the wire to be pulled by the pulling wire winding mechanism is restricted. This operation portion also restricts the rotatable amount of the rotational roller.

The position of the projected portion 81 of the wire winding amount restriction mechanism of this embodiment can be adjusted in the rotational roller 61. Therefore the rotatable amount of the rotational roller 61 can be adjusted. More specifically, a plurality of concave portions 84 is formed on the surface of the rotational roller 61. In the embodiment, the concave portions 84 are formed at regular intervals. The projected portion 81 is removably mounted on the concave portions 84. Thus a concave portion at an arbitrary position can be selected. Thereby the rotatable amount of the rotational roller 61 can be adjusted.

In the above-described embodiment, the projected portions 81 are formed on the outer surface of the rotational roller in a direction in which they project from the outer surface of the rotational roller. But they may be formed on a flat plane. In this case, the locking portion is provided at a position corresponding to that of the projected portion.

The operation portion may be constructed as shown in FIGS. 55 through 58.

Figure 55:
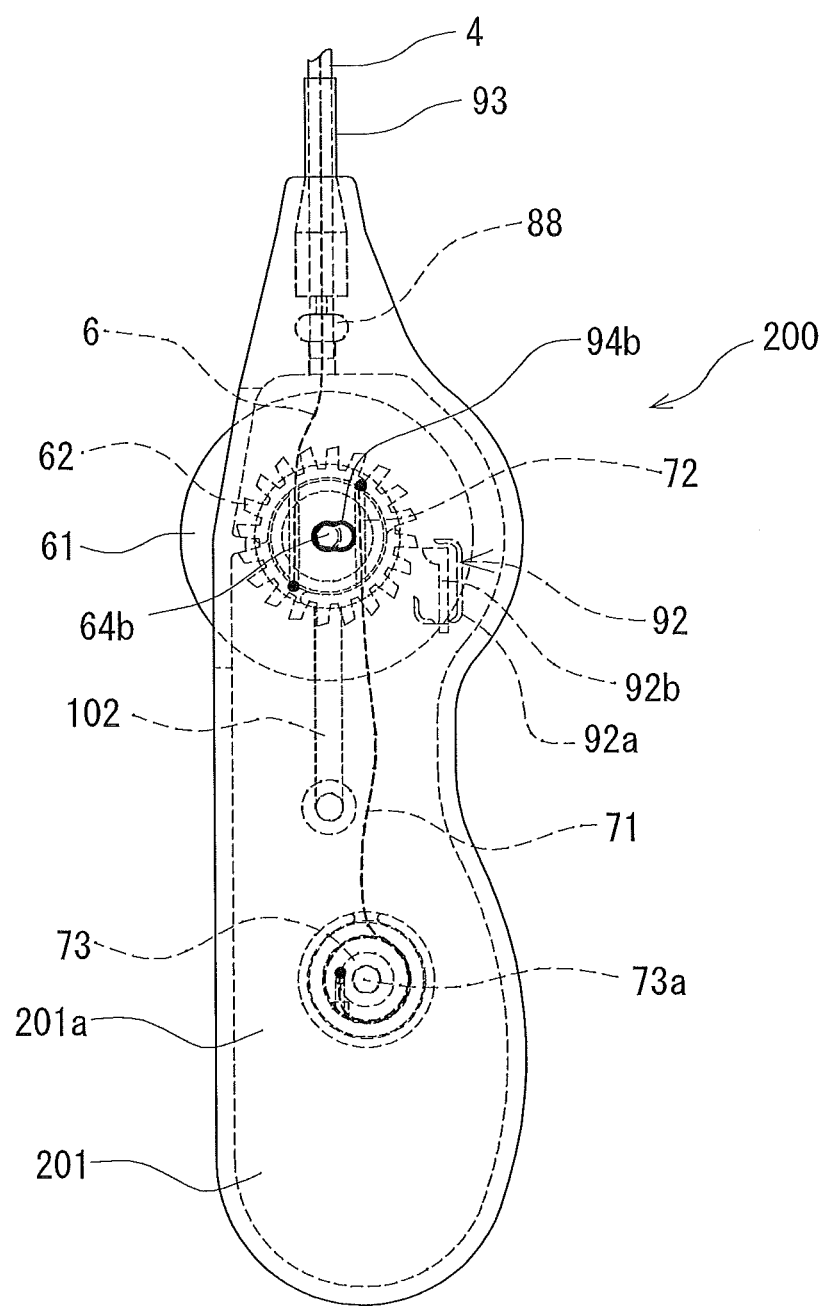
FIG. 55 is an enlarged front view showing the neighborhood of an operation portion of a stent delivery device of another embodiment of the present invention.
Figure 56:
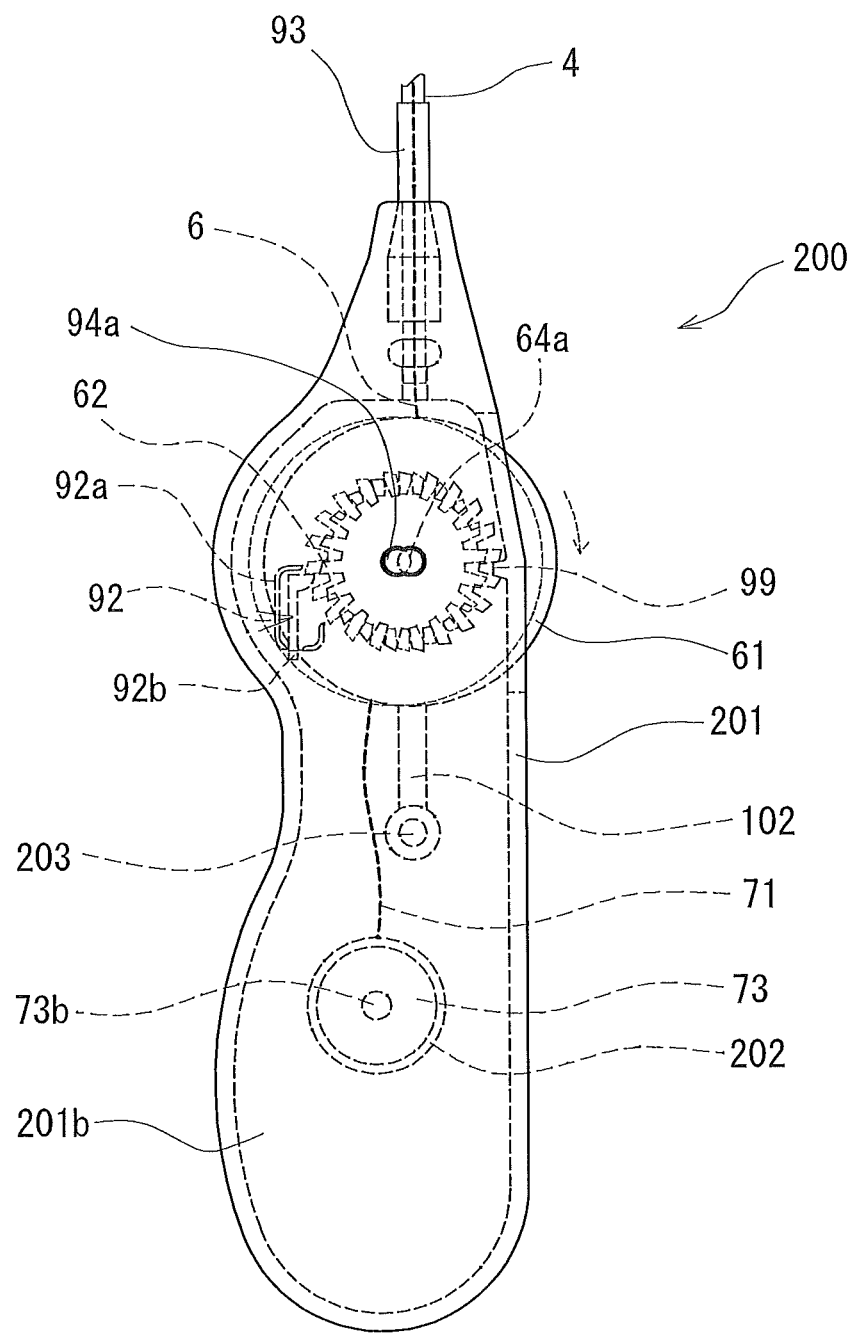
FIG. 56 is a rear side view showing the neighborhood of the operation portion of the stent delivery device shown in FIG. 55.
Figure 57:
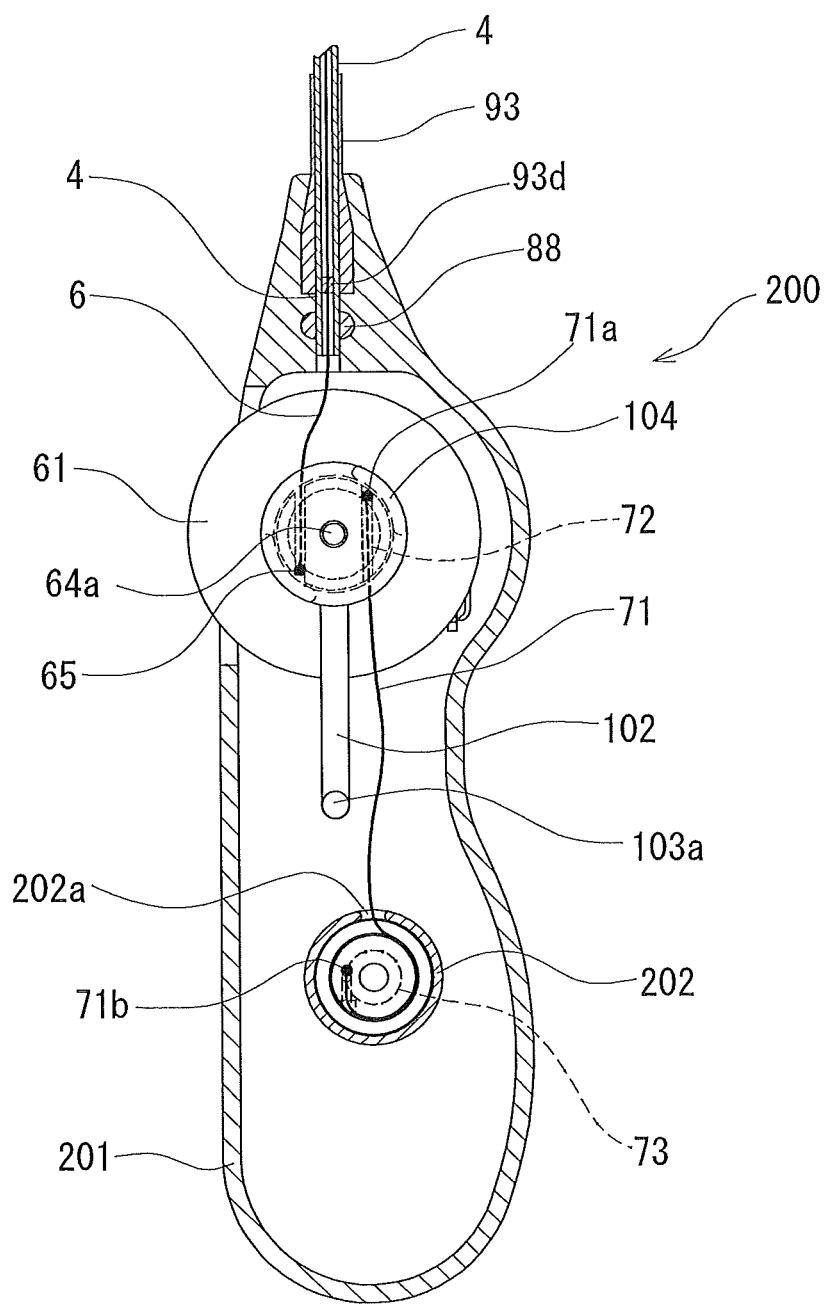
FIG. 57 is an explanatory view for explaining an internal construction of the neighborhood of an operation portion of the stent delivery device shown in FIG. 55.
Figure 58:
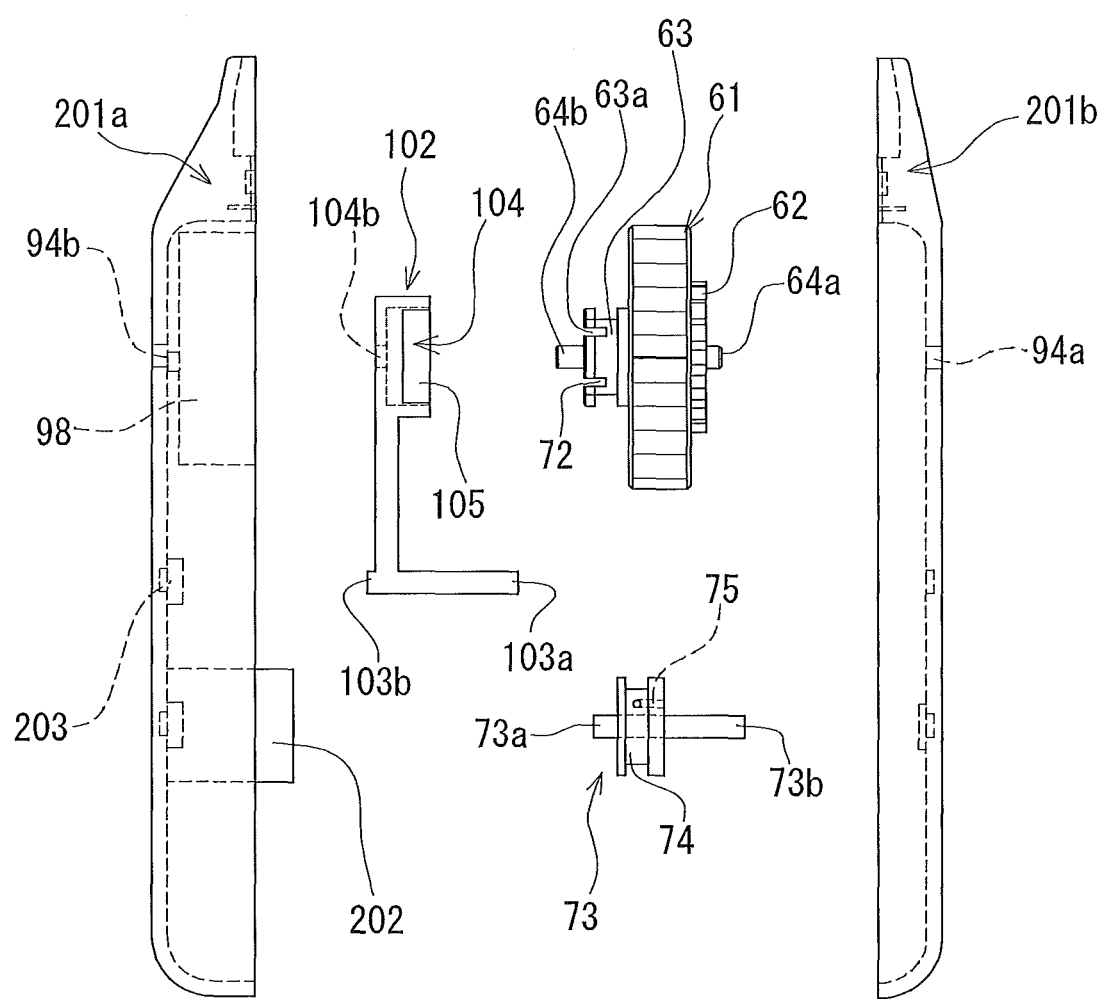
FIG. 58 is an explanatory view for explaining the internal construction of the neighborhood of the operation portion of the stent delivery device shown in FIG. 55.

FIG. 55 is an enlarged front view showing the neighborhood of an operation portion of a stent delivery device of another embodiment of the present invention. FIG. 56 is a rear side view showing the neighborhood of the operation portion of the stent delivery device shown in FIG. 55. FIG. 57 is an explanatory view for explaining an internal construction of the neighborhood of an operation portion of the stent delivery device shown in FIG. 55. FIG. 58 is an explanatory view for explaining the internal construction of the neighborhood of the operation portion of the stent delivery device shown in FIG. 55.

The basic construction of an operation portion 200 of this embodiment is the same as that of the above-described operation portion 100. The operation portion 200 is different from the operation portion 100 in the configuration of a housing shown in FIG. 58, the position of the winding shaft portion 63 and that of the gear portion 62 with respect to the rotational roller 61, the operation portion 200 has a collar member 102, the operation portion 200 is provided with a sealing member 88, and the operation portion 200 has a bobbin accommodation portion 202.

As shown in FIGS. 55 through 58, an operation portion 200 has a housing 201. The housing 201 is constructed of a first housing 201a and a second housing 201b. The proximal side and central portion of the housing 201 is bent and rounded. This configuration allows the housing 201 to be held easily and the roller to be operated easily.

A connector 93 is fixed to the proximal end of the proximal-side tube 4. The connector 93 accommodates a sealing member 93d sealing the pulling wire 6 slidably and liquid-tightly. The proximal portion of the proximal-side tube 4 projects from the proximal portion of the connector 93 and is liquid-tightly fixed by means of a sealing member 88 disposed inside the operation portion 200. The proximal end of the proximal-side tube 4 penetrates through the sealing member 88. As in the case of the above-described operation portion 9, a wire protection tube may be provided. The housing 201 has a connector-mounting portion at its distal portion. As shown in FIG. 57, the proximal side of the connector 93 is fixedly accommodated in the connector-mounting portion.

The above-described materials can be used to compose the housing 201 of the operation portion and the connector 93. As materials for the sealing member 88, the sealing member 93d, and the wire protection tube, the above-described elastic materials are used.

As shown in FIGS. 55 through 58, the housing 201 includes an open portion for partly projecting the rotational roller 61, a locking rib 99 engaging projected portions of a gear portion 62 (see FIG. 56) provided on the roller 61, a bearing portion 94b accommodating one end 64b of the rotating shaft of the roller 61, and a bearing portion 94a accommodating the other end 64a of the rotating shaft of the roller 61. The locking rib 99 is so configured that it is capable of penetrating into the gap between adjacent projected portions formed on the gear portion 62 of the roller 61. As shown in FIGS. 55 and 56, the bearing portions 94a and 94b accommodate the one end 64b and the other end 64a of the rotating shaft of the roller 61 respectively and have the shape of a gourd extended in a direction in which they recede from the above-described locking rib 99. The bearing portions 94a and 94b are not limited to the shape of the gourd, but may have configurations which allow them to move a distance in which they are capable of disengaging from the locking rib. For example, the bearing portions 94a and 94b may be rectangular, elliptic, and gourd-shaped. In the operation portion 200 of the embodiment, the bearing portions 94a and 94b are gourdlike, as shown in FIGS. 55 and 56. Therefore the rotational roller 61 is pressed to allow the ends 64b, 64a of the rotating shaft of the roller 61 accommodated in a space formed at one side of the bearing portions 94a, 94b to ride across opposed rib portions formed on the inner side surface of the central portion of the bearing portions 94a, 94b. Thereby the ends 64b, 64a of the rotating shaft of the roller 61 are accommodated in a space formed at the other side of the bearing portions 94a, 94b. The state of the roller 61 is shown with the broken line of FIG. 56. In this state, the roller 61 is pressed by the urging member. Thereby the ends 64b, 64a of the rotating shaft of the roller 61 contact opposed ribs formed on the inner side surface of the central portion of the bearing portions 94a, 94b and thus do not move to the space formed at the one side of the bearing portions 94a, 94b. Therefore the roller 61 keeps a rotatable state.

In this embodiment, as shown in FIGS. 57 and 58, the operation portion 200 has a collar member 102. The collar member 102 accommodates the winding shaft portion 63 and has a collar portion 104 forming an annular space between it and the winding shaft portion 63. The collar portion 104 prevents the pulling wire wound around the winding shaft portion 63 from becoming loose. The collar member 102 has a function of guiding the rotational roller in its movement and suppressing shaking of the rotational roller when the rotational roller is pressed. The shaft of the collar member 102 is supported with a pin 103. Thus as shown in FIGS. 55 and 56, the bearing portions 94a, 94b are formed in the shape of a gentle circular arc about the pin 103. The bearing portions 94a and 94b have the length allowing the roller 61 to move a distance longer than the height of the locking rib 99. As shown in FIG. 58, the collar member 102 has two opposed cut-out portions 105 which reach the space inside the collar portion 104 from the side surface thereof. The pulling wire 6 penetrates through one of the cut-out portions 105 and is fixed to the winding shaft portion 63. The linear member 71 penetrates through the other cut-out portion 105 and is fixed to the winding shaft portion 63.

The pulling wire winding mechanism is constructed of the roller 61 and the winding shaft portion 63 which is rotated by the rotation of the roller 61. The proximal portion of the pulling wire 6 is held by the winding shaft portion 63 or secured thereto. More specifically, as shown in FIG. 57, an anchoring portion 65 larger than the wire 6 is provided at the proximal portion of the pulling wire 6. A slit 63a capable of accommodating the pulling wire 6 is formed in the winding shaft portion 63. The slit 63a of the winding shaft portion 63 accommodates the proximal portion of the pulling wire 6, with the anchoring portion 65 disposed outward from the slit 63a. Thereby when the winding shaft portion 63 having the above-described construction rotates, the wire 6 is wound on the outer surface thereof. The method of holding the proximal portion of the pulling wire 6 on the winding shaft portion 63 or securing the pulling wire 6 thereto is not limited to the above-described method, but any methods can be used. For example, the proximal end of the pulling wire 6 or the proximal portion thereof may be directly secured to the winding shaft.

It is preferable that the proximal portion of the pulling wire 6 to be wound on the winding shaft portion 63 is soft to allow the pulling wire 6 to be wound easily. To make the proximal portion of the pulling wire 6 flexible, it is possible to adopt a method of making the proximal portion of the pulling wire 6 of a flexible material and a method of decreasing the diameter of the proximal portion of the pulling wire 6.

In this embodiment, the winding shaft portion 63 is formed integrally with the rotational roller 61 to make the winding shaft portion 63 and the rotational roller 61 coaxial with each other. As shown in FIG. 55, the winding shaft portion 63 is provided on one side surface of the rotational roller 61. Thus by rotating the rotational roller 61, the winding shaft portion 63 rotates simultaneously therewith. It is preferable that the winding amount of the pulling wire is smaller than the amount of an operation required to rotate the rotational roller. By doing so, the pulling wire can be wound slowly, and moreover the stent accommodation cylindrical member 5 is allowed to move toward the proximal side of the stent delivery device slowly and favorably. In this embodiment, because the outer diameter of the winding shaft portion is smaller than that of the rotational roller, the winding amount of the pulling wire is allowed to be smaller than the amount of the operation required to rotate the rotational roller.

The outer diameter of the winding shaft portion 63 is favorably in the range of 1 to 60 mm and more favorably in the range of 3 to 30 mm. The outer diameter of the rotational roller is favorably 1 to 20 times and more favorably 1 to 10 times larger than that of the winding shaft portion. More specifically, the outer diameter of the rotational roller is favorably in the range of 10 to 60 mm and more favorably in the range of 15 to 50 mm.

The rotational roller and the winding shaft portion do not necessarily have to be formed integrally, but the winding shaft portion may be constructed of a separate member which follows the rotation of the rotational roller. As the transmission system of the rotational roller, it is possible to use a gear type, a belt type, and the like. It is preferable that surfaces of parts which have a possibility of contact with the surface of the rotational roller 61 in operating the rotational roller 61 is not slippery. For example, it is preferable to treat surfaces of parts which have a possibility of contact with the surface of the rotational roller 61 in operating the rotational roller 61 by knurling treatment, emboss treatment, application of a high-frictional material, and the like.

The other end of the linear member 71 is held by the winding shaft portion 63 or secured thereto. More specifically, as shown in FIGS. 57 and 58, a bulged portion (in other words, anchoring portion) 71a larger than the linear member 71 is provided at the other end portion of the linear member 71. A slit 72 capable of accommodating the linear member 71 is formed in the winding shaft portion 63. The slit 72 accommodates the other end portion of the linear member 71, with the anchoring portion 71a disposed outward from the proximal end of the slit 72. Thereby when the winding shaft portion 63 having the above-described construction rotates, the linear member 71 is wound on the outer surface thereof. The method of holding the linear member 71 on the winding shaft portion 63 or securing the linear member 71 thereto is not limited to the above-described method, but any methods can be used. For example, the proximal end of the linear member 71 or the proximal portion thereof may be directly secured to the winding shaft.

It is preferable that the portion of the linear member 71 to be wound on the winding shaft portion 63 is soft to allow the linear member 71 to be wound easily. To make the proximal portion of the linear member 71 flexible, it is possible to adopt a method of making the portion of the linear member 71 to be wound of a flexible material and a method of decreasing the diameter of the portion of the linear member 71 to be wound.

In this embodiment, the winding shaft portion 63 is formed integrally with the rotational roller 61 to make the winding shaft portion 63 and the rotational roller 61 coaxial with each other. As shown in FIG. 55, the winding shaft portion 63 is provided on one side surface of the rotational roller 61. By rotating the rotational roller 61, the winding shaft portion 63 rotates simultaneously therewith. It is preferable that the winding amount of the linear member is smaller than the amount of an operation required to rotate the rotational roller. By doing so, the linear member can be wound slowly.

In this embodiment, the linear member 71 is wound around the winding shaft portion 63. But in addition, it is possible to provide the rotational roller 61 with the linear member winding shaft separately from the winding shaft portion 63 and wind the linear member around the linear member winding shaft.

The operation portion 200 has a bobbin accommodation portion 202 which is a cylindrical projected portion provided on the inner surface of the housing 201 of the operation portion and rotatably accommodates the bobbin. A slit 202a into which the linear member is inserted is provided inside the bobbin accommodation portion. The bobbin accommodation portion prevents the linear member 71 wound around the bobbin 73 from becoming loose. As shown in FIG. 58, the bobbin 73 has an annular groove 74 on which the linear member is wound and groove or a hole 75 communicating with the annular groove.

The operation portion 200 of this embodiment has the locking mechanism for releasably locking a rotation of the pulling wire winding mechanism, and the reverse rotation prevention mechanism for preventing the rotation of the pulling wire winding mechanism in the direction opposite to the pulling wire winding direction.

As shown in FIGS. 55 and 56, the rotational roller 61 has the gear portion 62 which is coaxial therewith and rotates together therewith. As shown in FIG. 56, the gear portion 62 is provided on the other side surface (in other words, surface opposite to surface on which winding shaft portion 63 is provided) of the rotational roller 61. Thus the gear portion 62 and the winding shaft portion 63 are partitioned from each other by a wall constructed of the rotational roller.

The rotational roller 61 has the portion partly exposed from the open portion 98. The exposed portion serves as the operation portion. The roller 61 has one end 64a provided on one side surface (side surface of gear) of the rotating shaft thereof and the other end 64b provided on the other side surface (side surface of winding shaft) thereof.

The urging means 92 for urging the rotational roller 61 toward the open portion 98 of the housing 101 is provided inside the housing 201. More specifically, the urging member 92b of the urging means 92 urges the roller 61. The housing 201 accommodates the locking rib 99 capable of penetrating into the gap between adjacent projected portions formed on the gear portion 62 of the roller 61. Therefore the rotating roller 61 has a state shown in FIG. 56, when the rotating roller 61 is urged by the urging member 92b. Thus the locking rib 99 engages the projected portion of the gear portion 62. Thus the rotating roller 61 is incapable of rotating. When the rotating roller 61 is pressed in the direction in which it moves away from the locking rib 99, the one end 64b and other end 64a of the rotating shaft of the roller 61 move inside the bearing portions 94b and 94a respectively provided in the housing 201. Thereby the rotational roller 61 becomes rotatable. Thus the operation portion 200 of this embodiment prevents the rotation of the rotational roller 61 when it is not pressed and has the locking mechanism for releasably locking the rotation of the pulling wire winding mechanism.

The operation portion of this embodiment has the reverse rotation prevention mechanism composed of the urging means 92 having the urging member 92b and the above-described gear portion 62. The reverse rotation prevention mechanism prevents the rotation of the pulling wire winding mechanism in the direction opposite to the pulling wire winding direction. The urging means 92 has the urging member 92b and the fixing member 92a for fixing the urging member 92b to the housing 201. As the urging member 92b, a spring-like member is used. The springlike member extends from the fixing member 92a to a lower portion of the gear portion 62 through the rear (direction opposite to distal portion of operation portion) of the gear portion 62 in such a way that the distal end of the springlike member engages the projected portions disposed at the lower portion of the gear portion 62. Because the springlike member is pressed against the gear portion 62, with the springlike member in contact therewith, as described above, the roller 62 is urged toward the open portion 98 of the housing. The roller 61 is pressed as described above and the roller 61 is rotatable. The roller 61 is rotatable in the direction (pulling wire-winding direction) shown with the arrow of FIG. 56. If an operation of rotating the roller 61 in the opposite direction is performed, the projected portion of the gear portion 62 and the distal end of the urging member 92b engage each other. Thereby the rotation of the roller 61 is prevented. Thereby the reverse rotation prevention mechanism prevents the rotation of the pulling wire winding mechanism in the direction opposite to the pulling wire winding direction.

The diameter of the gear portion 62 is set smaller than that of the rotational roller. The outer diameter of the gear portion 62 is favorably in the range of 10 to 60 mm and more favorably in the range of 15 to 50 mm. The number of cogs thereof is favorably in the range of 4 to 200 and more favorably in the range of 4 to 70.

As shown in FIG. 55, in the operation portion 200, the urging member 92 penetrates between the inner surface of the housing 201 and the side surface of the rotational roller 61, and the distal end thereof contacts the gear portion 62. Therefore the movement of the urging member 92b in a lateral direction is prevented by the inner surface of the housing 201 and the side surface of the rotational roller 61.

The shaft of the collar member 102 of the operation portion 200 is supported with the pin 103 at its one end. The collar portion 104 at the other side of the collar member 102 accommodates the winding shaft portion 63 and forms an annular space between the collar portion 104 and the winding shaft portion 63. The annular space is not very large and formed annularly between collar portion 104 and the outer surface of the wound wire.

In the stent delivery devices 80 and 120, by rotating the roller in the direction shown with the arrow of FIG. 51, the linear member 71 is wound around the winding shaft portion 63. After a windable amount of the linear member 71 is wound, it is impossible to perform an operation of rotating the roller 61.

The stent delivery devices 80, 120 of this embodiment may have a mode similar to that of the stent delivery device 10 of the above-described embodiment. As described above, the stent delivery device 10 is the same as the stent delivery device 1 except that the stent delivery device 10 does not have the intermediate tube and that the mode of the distal-side tube the former is different from the mode of the distal-side tube of the latter. Other construction of the former is the same as that of the latter.

Figure 52:
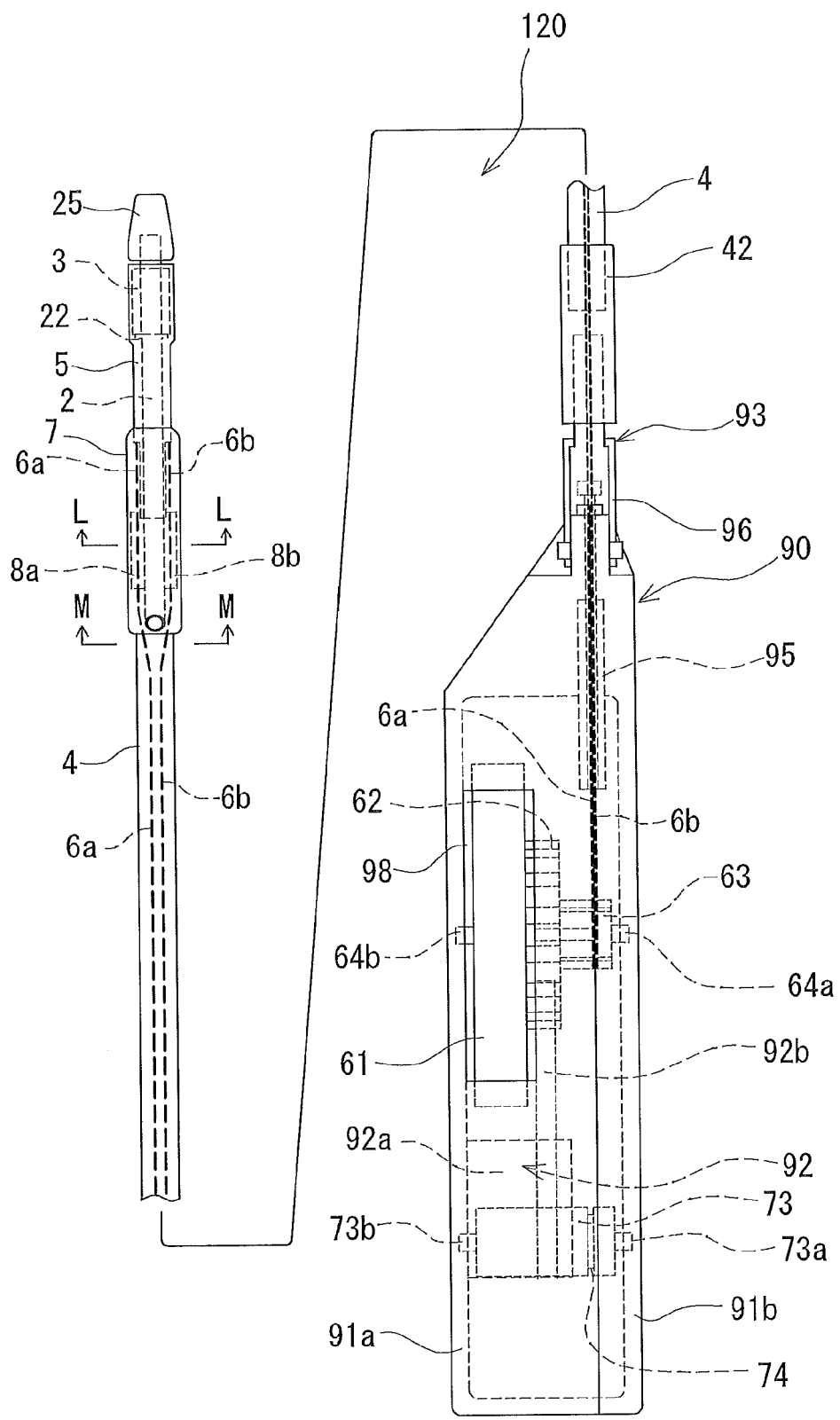
FIG. 52 is a partially schematic enlarged outlook view showing a stent delivery device of another embodiment of the present invention.

The stent delivery device 80 of this embodiment may have a plurality of (more specifically, two) the pulling members. A stent delivery device 120 of the embodiments shown in FIGS. 52, 39, and 40 has two pulling wires. FIG. 52 is a partially schematic enlarged outlook view showing a stent delivery device of another embodiment of the present invention. The sectional view taken along the line L-L shown in FIG. 52 is similar to that shown in FIG. 39. The sectional view taken along the line M-M shown in FIG. 52 is similar to that shown in FIG. 40.

The stent delivery device 120 is the same as the stent delivery device 80 except that the stent delivery device 120 has two pulling members and that there are some differences generated caused thereby. Other construction of the former is the same as that of the latter. Thus the same parts of the former as those of the latter are denoted by the same reference numerals as those of the latter, and description thereof is omitted herein. The above-described stent delivery device 120 may be provided with two pulling members.

As shown in FIGS. 52 and 39, the stent accommodation cylindrical member 5 of the stent delivery device 120 has two slits 52a, 52b extended from the proximal end of the stent accommodation cylindrical member 5 toward its distal end and disposed at positions opposed to each other. In correspondence to the positions of the slits 52a, 52b, the distal-side tube 2 has two tubular members 8a, 8b formed at positions opposed to each other.

Two pulling members 6a, 6b are fixed to the proximal portion of the stent accommodation cylindrical member 5 at positions opposed to each other. As shown in FIGS. 52, 39, and 40, the pulling member 6a extends inside the proximal-side tube 4 in penetration through the tubular member 8a and enters into the operation portion 90 at the proximal portion thereof. Similarly the pulling member 6b extends inside the proximal-side tube 4 in penetration through the tubular member 8b and fixed to the winding shaft of the operation portion 9 at the proximal portion of the stent accommodation cylindrical member 5.

In the stent delivery device of the present invention, it is possible to pull a pulling wire favorably, provided that the stent delivery device has a member, for maintaining the position of the pulling wire, which is disposed on the outer surface of the distal-side tube and has a passage through which the pulling wire is capable of penetrating.

In the stent delivery device of the present invention, it is possible to move the stent accommodation cylindrical member to move favorably toward the proximal side of the stent delivery device, provided that a projected portion is provided on an outer surface of the distal-side tube and that the stent accommodation cylindrical member has a slit which extends from a distal end thereof toward a distal side thereof and into which the projected portion is capable of moving.

In all the above-described embodiments, a rigidity-imparting member (not shown) may be inserted into the proximal-side tube 4. It is preferable that the proximal portion of the rigidity-imparting member is fixed to the proximal-side tube and that the distal end of the rigidity-imparting member is projected from the distal end of the proximal-side tube and extended to the inside the distal-side tube. It is preferable that only the proximal portion of the rigidity-imparting member is fixed to the proximal-side tube and other portions thereof are not fixed not to prevent the stent delivery device from curving. The rigidity-imparting member serves as a means for preventing the proximal-side tube from being extremely bent at a portion to be bent and the proximal-side tube from zigzagging in a blood vessel without much deteriorating the flexibility of the proximal-side tube. It is preferable that the rigidity-imparting member is made of a linear member. It is preferable that the linear member is a metal wire. As the metal wire, an elastic metal and a super-elastic alloy can be used. The diameter of the metal wire is in the range of 0.05 to 1.5 mm and favorably in the range of 0.1 to 1.0 mm. A high tensile stainless steel wire for spring and a super-elastic alloy wire are particularly favorable.

In all the above-described embodiments, the stent delivery devices have a rigidity-imparting member 11 respectively.

Figure 59:
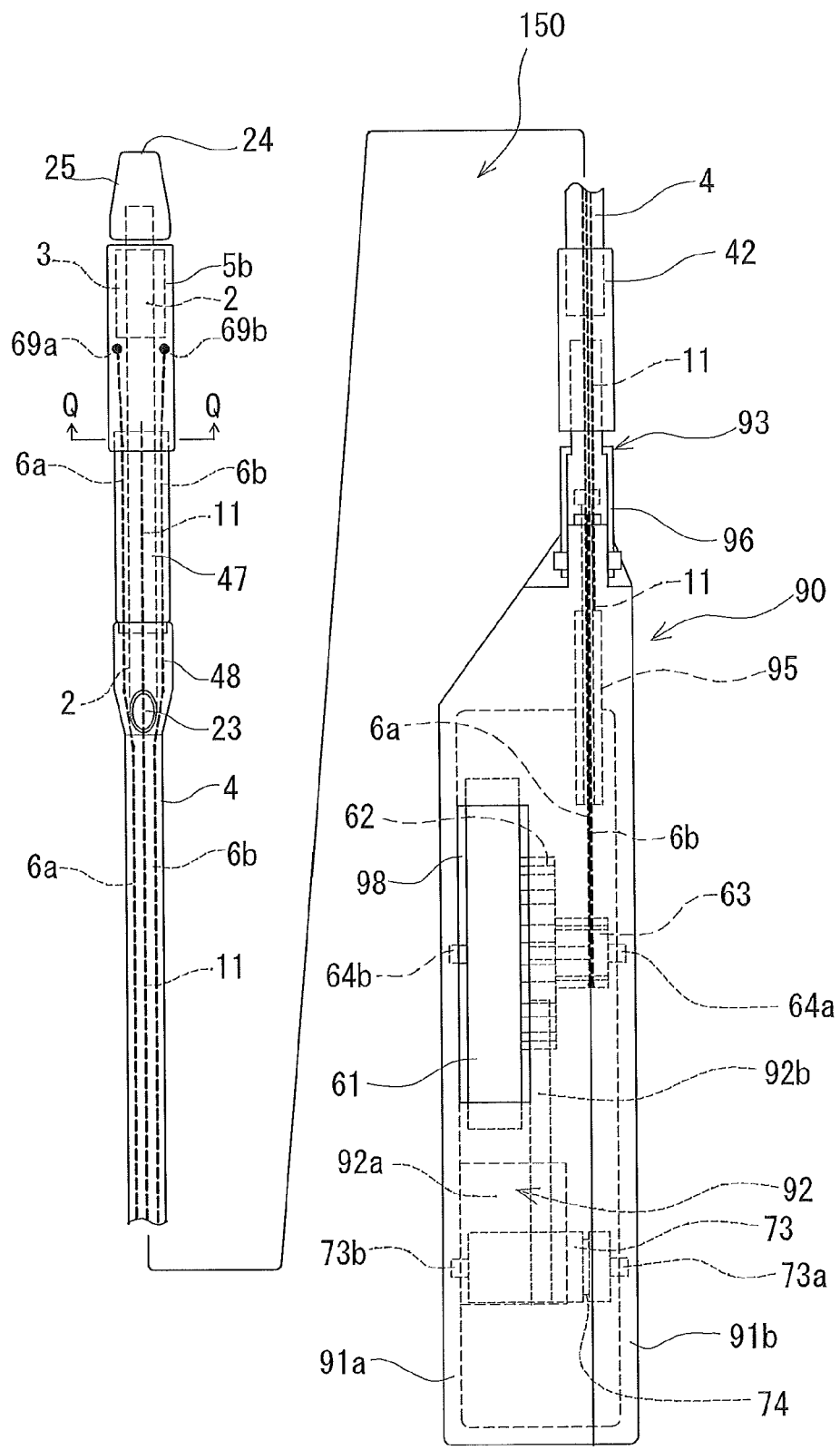
FIG. 59 is a partially schematic enlarged outlook view showing a stent delivery device of another embodiment of the present invention.
Figure 60:
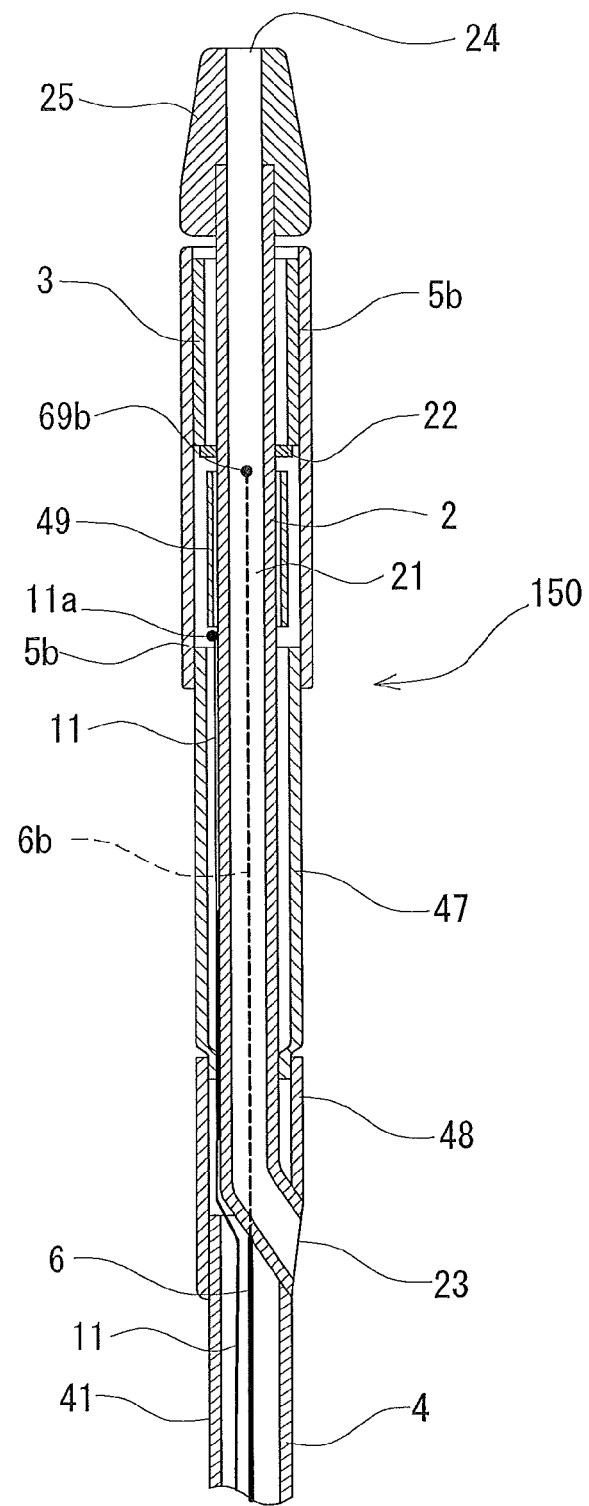
FIG. 60 is an enlarged sectional view showing the neighborhood of a distal portion of the stent delivery device shown in FIG. 59.
Figure 61:
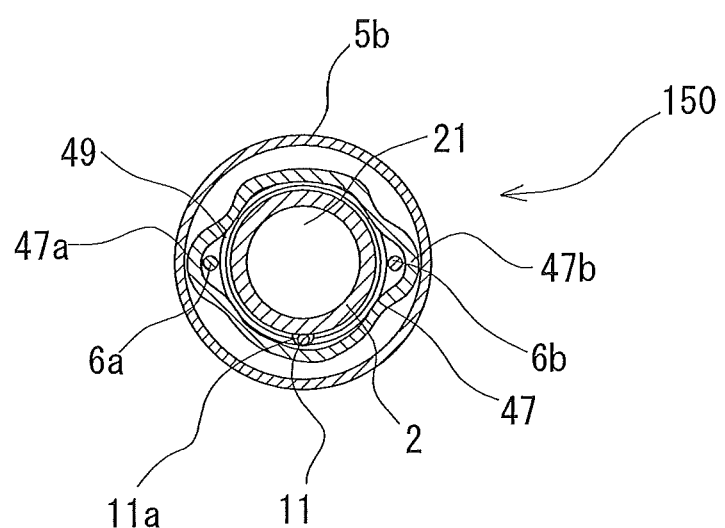
FIG. 61 is an enlarged sectional view taken along a line Q-Q of FIG. 59.

FIG. 59 is a partially schematic enlarged outlook view showing a stent delivery device of another embodiment of the present invention. FIG. 60 is an enlarged sectional view showing the neighborhood of a distal portion of the stent delivery device shown in FIG. 59. FIG. 61 is an enlarged sectional view taken along a line Q-Q of FIG. 59.

The basis constitution of the stent delivery device 150 of this example is substantially same with the stent delivery device 40 shown in FIGS. 19 through 22 and mentioned above.

The stent delivery device 150 of this embodiment has the rigidity-imparting member 11 separately from the above-described pulling wire (pulling member). As shown in FIGS. 59 and 60, the rigidity-imparting member 11 extends from the proximal side of the stent delivery device 150, passes inside the proximal-side tube, and penetrates into the stent accommodation cylindrical member 5b. As shown in FIGS. 59 and 60, the distal end 11a of the rigidity-imparting member 11 is fixed to the outer surface of the distal-side tube 2 by means of a fixing portion 11a. It is particularly preferable that the distal end of the rigidity-imparting member is fixed to the outer surface of the distal-side tube 2 at a position of the distal side from the tip of the position intermediate tube 47. It is preferable that the rigidity-imparting member 11 is fixed to the proximal portion of the proximal-side tube 4 or the operation portion at the proximal portion thereof. The rigidity-imparting member 11 serves as a means for suppressing deformation of the stent delivery device when the pulling member (pulling wire) is pulled. A twisted wire material or a plurality of twisted wire materials can be preferably used as the material for composing the rigidity-imparting member 11. The diameter of the rigidity-imparting member 11 is in the range of favorably 0.01 to 1.5 mm and more favorably 0.1 to 1.0 mm.

As the material for forming the rigidity-imparting member 11, the following substances can be used: stainless steel wire (preferably, high tensile stainless wire for spring); music wire (preferably, nickel-plated or chromium-plated music wire); super-elastic alloy wire; wires made of metal such as Ni—Ti alloy, Cu—Zn alloy, Ni—Al alloy, tungsten, tungsten alloy, titanium, titanium alloy, cobalt alloy, tantalum. It is preferable that the rigidity-imparting member 11 is harder than the pulling member (pulling wire).

The stent delivery device 150 shown in FIGS. 59 through 61 has an intermediate tube 7. A distal end of the intermediate tube 47 enters in the cylindrical member 5b. The intermediate tube 47 is fixed at the proximal portion thereof to the proximal portion of the distal-side tube 2 and the distal portion of the proximal-side tube 4. In the stent delivery device 150 of this embodiment, the intermediate tube 7 encloses the proximal side of the distal-side tube 2 and the proximal side of the stent accommodation cylindrical member 5b without preventing the stent accommodation cylindrical member 5 from moving toward the proximal side of the stent delivery device 1. The intermediate tube 7 is insertable into the cylindrical member 5b. The pulling members 6a, 6b pass the intermediate tube 47. Distal ends of the pulling members 6a, 6b enter into the stent accommodation cylindrical member 5b and are fixed to the inner surface of the accommodation cylindrical member 5b at the middle portion of the member 5b. The pulling member 6 passes between the intermediate tube 47 and the distal-side tube 2 and extends into the proximal-side tube 4. A space forming tube 49 is inserted between the stent accommodation cylindrical member 5b and the distal-side tube 2. The space forming tube 49 is not fixed to the stent accommodation cylindrical member 5b and the distal-side tube 2.

The rigidity-imparting member 11 passes inside the proximal-side tube 4, penetrates into the intermediate tube 47, penetrates into the space between the stent accommodation cylindrical member 5b and the distal-side tube 2 from the read end of the stent accommodation cylindrical member 5b, and extends toward the distal side of the stent accommodation cylindrical member 5.

Similarly to the stent delivery devices 20, 40, 70, and 120 of the above-described embodiments, the stent delivery device 150 of this embodiment has two pulling wires. The construction of the stent delivery device 150 having two pulling wires is the same as that of the stent delivery device 40 of the above-described embodiment.

Two pulling members 6a, 6b are fixed to the middle portion of the stent accommodation cylindrical member 5b at positions opposed to each other. As shown in FIGS. 38 through 40, the pulling wire 6a extends inside the proximal-side tube 4 in penetration through the intermediate tube 47 and fixed to the winding shaft of the operation portion 90 at the proximal portion thereof. Similarly the pulling wire 6b extends inside the proximal-side tube 4 in penetration through the intermediate tube 47 and fixed to the winding shaft of the operation portion 90 at the proximal portion thereof. When the two pulling members 6a, 6b are used, they may be integrated with each other at the proximal portion of the stent accommodation cylindrical member 5. As shown in FIG. 61, the two pulling members 6a, 6b are spaced at a predetermined interval inside the stent accommodation cylindrical member 5b. As shown in FIG. 61, inside the stent accommodation cylindrical member 5b, the rigidity-imparting member 11 is spaced at an equal interval from the pulling wires 6a and 6b.

Figure 62:
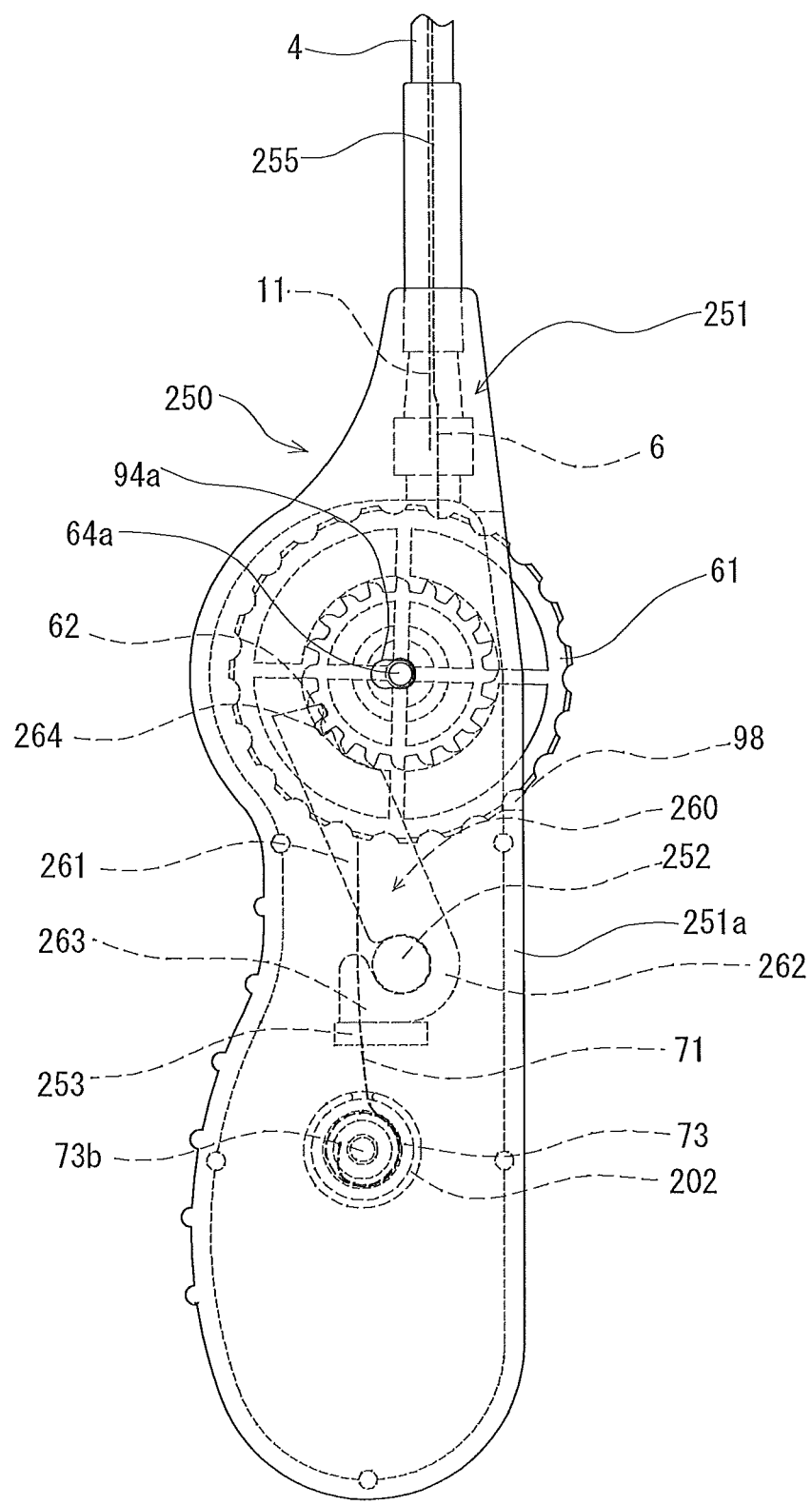
FIG. 62 is an enlarged front view showing the neighborhood of an operation portion of a stent delivery device of another embodiment of the present invention.
Figure 63:
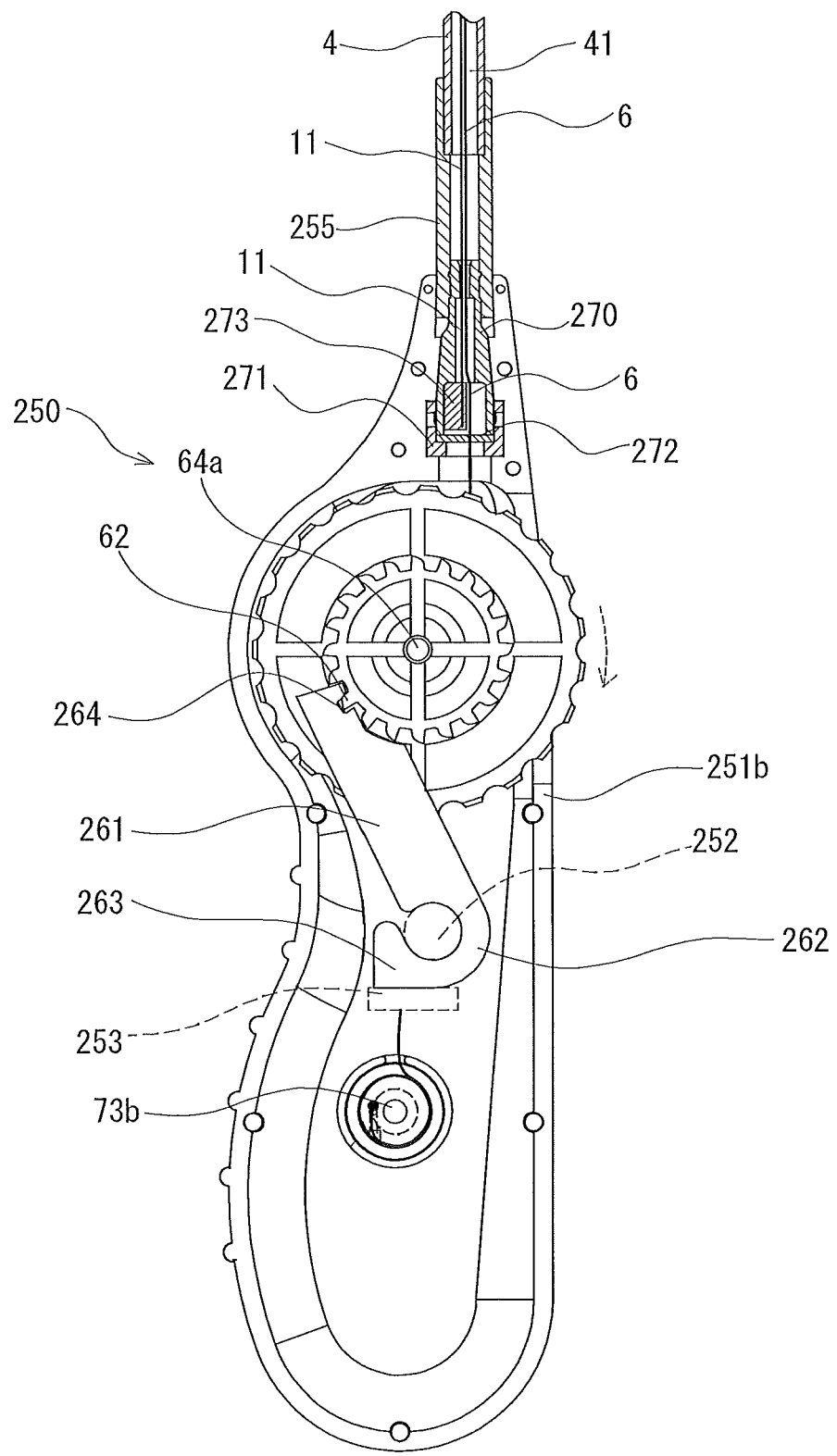
FIG. 63 is an explanatory view for explaining an internal construction of the neighborhood of the operation portion of the stent delivery device shown in FIG. 62.
Figure 64:
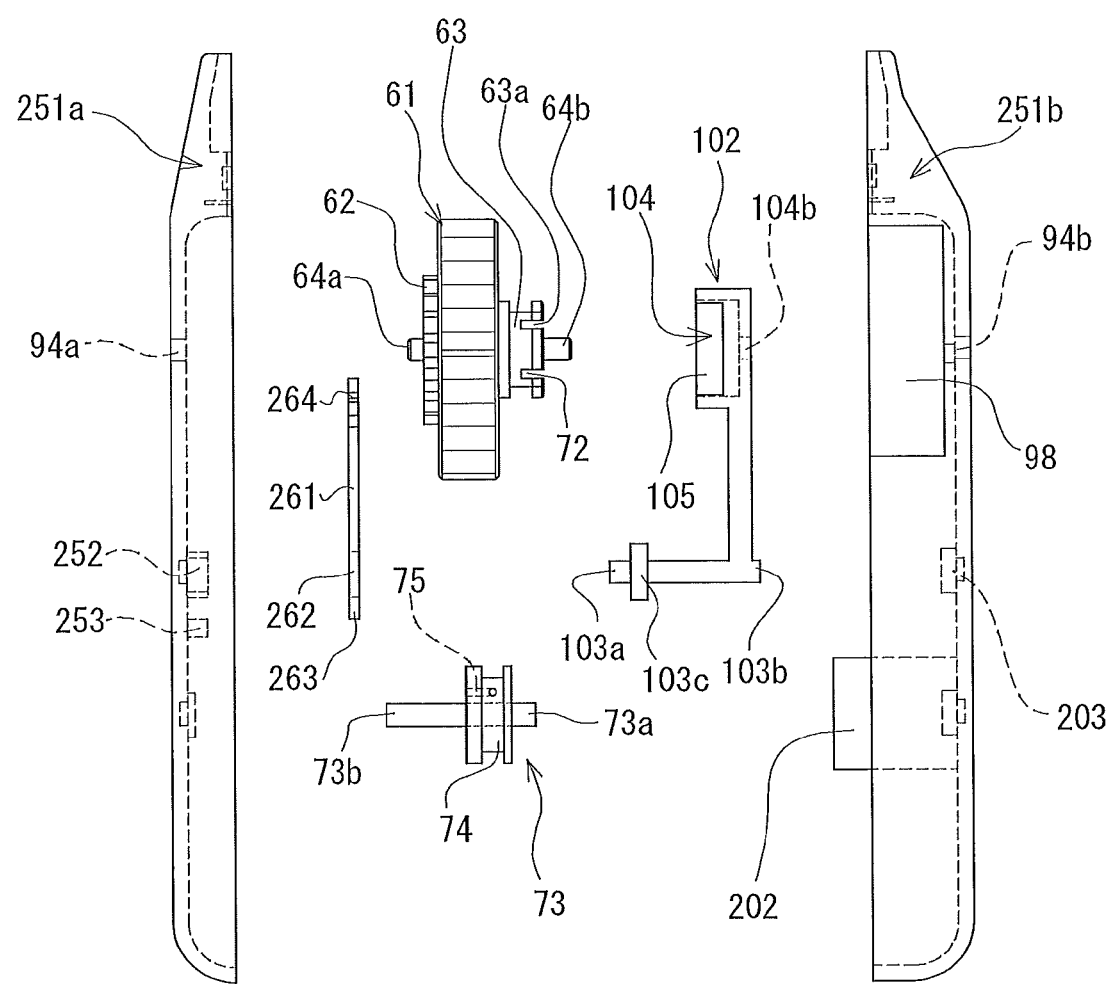
FIG. 64 is an explanatory view for explaining an internal construction of the neighborhood of the operation portion of the stent delivery device shown in FIG. 62.

In all the above-described embodiments, the operation portion may be formed as shown in FIGS. 62 through 64.

FIG. 62 is an enlarged front view showing the neighborhood of an operation portion of a stent delivery device of another embodiment of the present invention. FIG. 63 is an explanatory view for explaining an internal construction of the neighborhood of the operation portion of the stent delivery device shown in FIG. 62. FIG. 64 is an explanatory view for explaining an internal construction of the neighborhood of the operation portion of the stent delivery device shown in FIG. 62. FIG. 63 shows a state in which the first housing of the operation portion is removed from the operation portion of the stent delivery device shown in FIG. 62 and also shows a section of the connector.

The basic construction of the operation portion 250 of this embodiment is the same as that of the operation portion 200 except the construction of the reverse rotation prevention mechanism 260 of the rotational roller 61 and that of a part of the connector. Thus the other constructions of the operation portion 250 are referred to the description of the operation portion 200.

As shown in FIGS. 62 through 64, the operation portion 250 has a housing 251. The proximal side and the central portion of the housing 251 are bent and rounded. This configuration allows the housing 251 to be held easily and the roller to be operated easily. The housing 251 is constructed of a first housing 251a and a second housing 251b.

The distal portion of a cylindrical connector 255 is fixed to the proximal end of the proximal-side tube 4. The housing 251 of the operation portion accommodates a sealing mechanism connected to the proximal portion of the connector 255. The sealing mechanism has a cylindrical body member 270, having a distal portion, which is fixed to the proximal portion of the connector 255, a cap member 271 fixed to the proximal end of the cylindrical body member 270, a sealing member 272 disposed between the cylindrical body member 270 and the cap member 271, and a rigidity-imparting member-fixing member 273. The sealing member 272 has a hole or a slit through which the pulling wire (6a, 6b) is penetrated liquid-tightly and slidably. The proximal portion of the rigidity-imparting member 11 is fixed to the rigidity-imparting member-fixing member 273. The rigidity-imparting member-fixing member 273 is fixed to the inside of the cylindrical body member 270. The above-described materials can be used to compose the connector. The above-described elastic materials are used to compose the sealing member.

As shown in FIGS. 62 and 64, the housing 251 includes the open portion 98 for partly projecting the rotational roller 61, a bearing portion 94a accommodating other end 64a of the rotating shaft of the roller 61, and a bearing portion 94b accommodating one end 64b of the rotating shaft of the roller 61. Although not shown, the housing 251 has a locking rib. The bearing portions 94a and 94b are gourd-shaped and extended in a direction in which they recede from the locking rib.

The reverse rotation prevention mechanism of the operation portion 250 of this embodiment is described below.

As shown in FIGS. 62 through 64, the rotational roller 61 has the gear portion 62 which is coaxial therewith and rotates together therewith. As shown in FIG. 64, the gear portion 62 is provided on a surface opposite to a surface on which the winding shaft portion 63 of the rotational roller 61 is provided. Thus the gear portion 62 and the winding shaft portion 63 are partitioned from each other by a wall constructed of the rotational roller.

As shown in FIGS. 62 and 63, the reverse rotation prevention mechanism 261 is accommodated in the operation portion 250. The reverse rotation prevention mechanism 261 has an engaging portion 264, disposed at a portion opposed to the gear portion 62 of the rotational roller 61, capable of engaging the gear portion, an elastically deformable portion 262, and a portion 263 to be mounted on the housing. The housing 251b has a first projected portion 252 and a second projected portion 253 both formed on the inner surface thereof. The first projected portion 252 penetrates into the elastically deformable portion 262 and has an outer configuration corresponding to the inner configuration of the elastically deformable portion 262. More specifically, the inner surface of the elastically deformable portion 262 is circular arc-shaped. The first projected portion 252 is also circular arc-shaped in correspondence thereto. The portion 263 to be mounted on the housing of the reverse rotation prevention mechanism 261 is so configured as to be mounted between the first projected portion 252 and the second projected portion 253 formed on the inner surface of the housing 251b. Because the accommodation portion 263 of the reverse rotation prevention mechanism 261 is mounted between the first projected portion 252 and the second projected portion 253, the rotational roller 61 is incapable of rotating and urged toward the open portion 58 by the elastic force of the elastically deformable portion 262. The collar member 102 has a disk state rib 103c. The portion 263 to be mounted on the housing of the reverse rotation prevention mechanism 261 is held at a side surface thereof by the disk state rib 103c.

As described above, by pressing the roller 61, the roller can be rotated. The roller 61 is rotatable in the direction (pulling wire-winding direction) shown with the arrow of FIG. 63. If an operation of rotating the roller 61 in the opposite direction is performed, one cog of the gear portion 62 and the engaging portion 264 of the reverse rotation prevention mechanism 261 engage each other. Thereby the rotation of the roller 61 is prevented. Thereby the reverse rotation prevention mechanism prevents the rotation of the roller of the pulling wire winding mechanism in the direction opposite to the pulling wire winding direction. As shown in FIG. 64, in the operation portion 250, the reverse rotation prevention mechanism 261 is disposed between the inner surface of the housing 251b and the side surface of the rotational roller 61. Therefore the movement of the reverse rotation prevention mechanism 261 in a lateral direction (horizontal direction) is prevented by the inner surface of the housing 251b and the side surface of the rotational roller 61.

The construction of the pulling wire winding mechanism is not limited to the above-described one, but any pulling wire winding mechanisms capable of winding a wire can be used. The construction of the locking mechanism is not limited to the above-described one, but any locking mechanisms capable of releasably locking the rotation of the pulling wire winding mechanism can be used. The construction of the reverse rotation prevention mechanism is not limited to the above-described one, but it is possible to use any reverse rotation prevention mechanism s capable of preventing the roller from rotating in a direction opposite to a pulling wire winding direction.

What is claimed is:
1. A stent delivery device comprising:
a distal-side tube having a guide wire lumen;
a proximal-side tube having a distal portion fixed to a proximal portion of said distal-side tube;
a cylindrical member which encloses a distal side of said distal-side tube and is slidable toward a proximal end of said distal-side tube;
a stent housed in said cylindrical member;
an intermediate tube which encloses a proximal side of said distal-side tube and a proximal side of said cylindrical member and is fixed at a proximal portion thereof to the proximal portion of said distal-side tube and the distal portion of said proximal-side tube, and
a pulling member which extends inside said proximal-side tube, with one end portion thereof fixed to said cylindrical member and is pulled toward said proximal side of said proximal-side tube to move said cylindrical member toward a proximal side of said stent delivery device,
wherein said distal-side tube has a proximal-side opening which is open at said proximal side of said distal-side tube and communicates with said guide wire lumen; and
a stent-locking portion which is disposed at said distal side of said distal-side tube and contacts a proximal end of said stent accommodated inside said cylindrical member, thus preventing said stent from moving to said proximal side of said stent delivery device;

said stent is formed approximately cylindrically, and is accommodated in said cylindrical member, with said stent being compressed in an axial direction thereof, and expands outward and returns to a configuration before said stent is compressed, when said stent is implanted in an organism; and an outer diameter of said proximal-side tube is set smaller than an outer diameter of a portion, having a maximum diameter, which is disposed in a region distal from said proximal-side tube;

wherein said cylindrical member thereby defines a stent accommodation cylindrical member configured to slide on an inner side of said intermediate tube when said pulling member is pulled toward said proximal side of said proximal-side tube.

2. A stent delivery device according to claim 1, wherein said distal-side tube has a projected portion, for preventing a movement of said stent, which is provided at a side distal from said distal end of said stent; and a distal side of said projected portion for preventing said movement of said stent is gradually decreased in a diameter thereof toward a distal end thereof.

3. A stent delivery device according to claim 1, further comprising a member, for maintaining a position of said pulling member, which is disposed on an outer surface of said distal-side tube and has a passage through which said pulling member is capable of penetrating.

4. A stent delivery device according to claim 1, further comprising a projected portion provided on an outer surface of said distal-side tube; and said cylindrical member has a slit which extends from a proximal end thereof toward a distal side thereof and into which said projected portion is capable of moving.

5. A stent delivery device according to claim 1, wherein a central longitudinal axis of said proximal-side tube is shifted in a direction away from said proximal-side opening with respect to a central longitudinal axis of said distal-side tube such that the central longitudinal axis of said proximal-side tube is offset relative to the central longitudinal axis of said distal-side tube.

6. A stent delivery device according to claim 1, wherein said pulling member extends from a proximal end of said proximal-side tube and has a member for pulling operation fixed to an extended portion of said pulling member.

7. A stent delivery device according to claim 1, wherein said proximal-side tube has a sealing member through which said pulling member penetrates in a liquid-tight state.

8. A stent delivery device according to claim 1, wherein a hub having a valve holding said pulling member slidably and liquid-tightly is provided at a proximal portion of said proximal-side tube.

9. A stent delivery device according to claim 1, further comprising a movement distance restriction portion for restricting a movement distance of said cylindrical member toward a proximal side of said stent delivery device.

10. A stent delivery device according to claim 1, wherein said intermediate tube encloses said proximal side of said distal-side tube and said proximal side of said cylindrical member without preventing said cylindrical member from moving toward said proximal side of said stent delivery device; one end portion of said pulling member is fixed to said cylindrical member inside said intermediate tube; and said pulling member passes a space between said intermediate tube and said distal-side tube and extends into said proximal-side tube.

11. A stent delivery device according to claim 1, wherein two pulling members are provided.

12. A stent delivery device according to claim 1, wherein said pulling member passes through a space between said intermediate tube and said distal-side tube such that said pulling member is not exposed.

* * * * *